United States Patent
Islam

(10) Patent No.: US 10,820,807 B2
(45) Date of Patent: Nov. 3, 2020

(54) TIME-OF-FLIGHT MEASUREMENT OF SKIN OR BLOOD USING ARRAY OF LASER DIODES WITH BRAGG REFLECTORS

(71) Applicant: OMNI MEDSCI, INC., Ann Arbor, MI (US)

(72) Inventor: Mohammed N. Islam, Ann Arbor, MI (US)

(73) Assignee: OMNI MEDSCI, INC., Ann Arbor, MI (US)

( * ) Notice: Subject to any disclaimer, the term of this patent is extended or adjusted under 35 U.S.C. 154(b) by 0 days.

(21) Appl. No.: 16/722,188

(22) Filed: Dec. 20, 2019

(65) Prior Publication Data

US 2020/0281477 A1  Sep. 10, 2020

Related U.S. Application Data

(60) Continuation of application No. 16/506,885, filed on Jul. 9, 2019, now Pat. No. 10,517,484, which is a
(Continued)

(51) Int. Cl.
*G01J 3/00* (2006.01)
*A61B 5/00* (2006.01)
(Continued)

(52) U.S. Cl.
CPC .......... *A61B 5/0088* (2013.01); *A61B 5/0013* (2013.01); *A61B 5/0022* (2013.01);
(Continued)

(58) Field of Classification Search
CPC ......... G01N 21/31; G01N 21/552; G01J 3/02; G01J 3/28; G01J 3/42
(Continued)

(56) References Cited

U.S. PATENT DOCUMENTS

| 4,063,106 A | 12/1977 | Ashkin et al. |
| 4,158,750 A | 6/1979 | Sakoe et al. |

(Continued)

FOREIGN PATENT DOCUMENTS

| CA | 2458123 | 9/2004 |
| CN | 101849821 A | 10/2010 |

(Continued)

OTHER PUBLICATIONS

Inter Partes Review No. IPR2020-00175; Petition for Inter Partes Review of U.S. Pat. No. 10,188,299; *Apple Inc.* v. *Omni Medsci, Inc.*; pp. 1-91; dated Dec. 11, 2019.
(Continued)

*Primary Examiner* — Md M Rahman
(74) *Attorney, Agent, or Firm* — Brooks Kushman P.C.

(57) ABSTRACT

A blood measurement system comprises an array of laser diodes, to generate light to penetrate tissue comprising skin, having one or more wavelengths, including a near-infrared wavelength, and Bragg reflector(s). At least one of the laser diodes to pulse at a pulse repetition rate between 1-100 megahertz. A detection system to measure blood in veins based at least in part on near-infrared diffuse reflection from the skin, the detection system comprising a photo-detector and a lens system coupled to the photo-detector, wherein the photo-detector is coupled to analog-to-digital converter(s) and a processor, and configured to measure absorption of hemoglobin in the near-infrared wavelength between 700-1300 nanometers, differentiate between regions in the skin with and without distinct veins, and implement pattern matching and a threshold function to correlate detected blood concentrations with a library of known concentrations to determine overlap.

8 Claims, 53 Drawing Sheets

Related U.S. Application Data continuation of application No. 16/284,514, filed on Feb. 25, 2019, now abandoned, and a continuation of application No. 16/272,069, filed on Feb. 11, 2019, now abandoned, and a continuation of application No. 16/241,628, filed on Jan. 7, 2019, now Pat. No. 10,441,176, and a continuation of application No. 16/188,194, filed on Nov. 12, 2018, now Pat. No. 10,386,230, said application No. 16/272,069 is a continuation of application No. 16/029,611, filed on Jul. 8, 2018, now Pat. No. 10,201,283, said application No. 16/284,514 is a continuation of application No. 16/016,649, filed on Jun. 24, 2018, now Pat. No. 10,213,113, said application No. 16/241,628 is a continuation of application No. 16/015,737, filed on Jun. 22, 2018, now Pat. No. 10,172,523, said application No. 16/506,885 is a continuation of application No. 16/004,359, filed on Jun. 9, 2018, said application No. 16/188,194 is a continuation of application No. 16/004,154, filed on Jun. 8, 2018, now Pat. No. 10,126,283, said application No. 16/029,611 is a continuation of application No. 15/888,052, filed on Feb. 4, 2018, now Pat. No. 10,136,819, said application No. 16/016,649 is a continuation of application No. 15/860,065, filed on Jan. 2, 2018, now Pat. No. 10,098,546, said application No. 16/004,154 is a continuation of application No. 15/855,201, filed on Dec. 27, 2017, now Pat. No. 9,995,722, which is a continuation of application No. 15/711,907, filed on Sep. 21, 2017, now Pat. No. 9,897,584, said application No. 15/860,065 is a continuation of application No. 15/686,198, filed on Aug. 25, 2017, now Pat. No. 9,861,286, said application No. 16/015,737 is a continuation of application No. 15/594,053, filed on May 12, 2017, now Pat. No. 10,188,299, said application No. 15/711,907 is a division of application No. 15/357,225, filed on Nov. 21, 2016, now Pat. No. 9,797,876, said application No. 15/686,198 is a continuation of application No. 15/357,136, filed on Nov. 21, 2016, now Pat. No. 9,757,040, said application No. 15/888,052 is a continuation of application No. 15/212,549, filed on Jul. 18, 2016, now Pat. No. 9,885,698, said application No. 15/594,053 is a continuation of application No. 14/875,709, filed on Oct. 6, 2015, now Pat. No. 9,651,533, said application No. 15/357,136 is a continuation of application No. 14/651,367, filed as application No. PCT/US2013/075736 on Dec. 17, 2013, now Pat. No. 9,500,635, said application No. 15/357,225 is a continuation of application No. 14/650,981, filed as application No. PCT/US2013/075767 on Dec. 17, 2013, now Pat. No. 9,500,634, said application No. 15/212,549 is a continuation of application No. 14/650,897, filed as application No. PCT/US2013/075700 on Dec. 17, 2013, now Pat. No. 9,494,567, said application No. 16/004,359 is a continuation of application No. 14/109,007, filed on Dec. 17, 2013, now Pat. No. 9,993,159, said application No. 14/875,709 is a continuation of application No. 14/108,986, filed on Dec. 17, 2013, now Pat. No. 9,164,032.

(60) Provisional application No. 61/754,698, filed on Jan. 21, 2013, provisional application No. 61/747,477, filed on Dec. 31, 2012, provisional application No. 61/747,472, filed on Dec. 31, 2012, provisional application No. 61/747,485, filed on Dec. 31, 2012, provisional application No. 61/747,487, filed on Dec. 31, 2012, provisional application No. 61/747,553, filed on Dec. 31, 2012.

(51) Int. Cl.

| | | |
|---|---|---|
| *G01N 33/49* | (2006.01) | |
| *G01N 33/44* | (2006.01) | |
| *G01N 33/15* | (2006.01) | |
| *G01N 33/02* | (2006.01) | |
| *G01N 21/88* | (2006.01) | |
| *G01N 21/39* | (2006.01) | |
| *G01N 21/3563* | (2014.01) | |
| *G01N 21/359* | (2014.01) | |
| *G01N 21/35* | (2014.01) | |
| *G01J 3/453* | (2006.01) | |
| *G01J 3/42* | (2006.01) | |
| *G01J 3/28* | (2006.01) | |
| *G01J 3/14* | (2006.01) | |
| *G01J 3/10* | (2006.01) | |
| *G01J 3/02* | (2006.01) | |
| *A61B 5/145* | (2006.01) | |
| *A61B 5/1455* | (2006.01) | |
| *H01S 3/30* | (2006.01) | |
| *H01S 3/067* | (2006.01) | |
| *H01S 3/00* | (2006.01) | |
| *G01N 21/95* | (2006.01) | |
| *G01N 21/85* | (2006.01) | |
| *G01M 3/38* | (2006.01) | |
| *G01J 3/12* | (2006.01) | |
| *G01J 3/18* | (2006.01) | |

(52) U.S. Cl.
CPC .......... *A61B 5/0075* (2013.01); *A61B 5/0086* (2013.01); *A61B 5/1455* (2013.01); *A61B 5/14532* (2013.01); *A61B 5/14546* (2013.01); *A61B 5/4547* (2013.01); *A61B 5/6801* (2013.01); *A61B 5/7257* (2013.01); *A61B 5/742* (2013.01); *A61B 5/7405* (2013.01); *G01J 3/0218* (2013.01); *G01J 3/108* (2013.01); *G01J 3/14* (2013.01); *G01J 3/28* (2013.01); *G01J 3/2823* (2013.01); *G01J 3/42* (2013.01); *G01J 3/453* (2013.01); *G01N 21/35* (2013.01); *G01N 21/359* (2013.01); *G01N 21/3563* (2013.01); *G01N 21/39* (2013.01); *G01N 21/88* (2013.01); *G01N 33/02* (2013.01); *G01N 33/025* (2013.01); *G01N 33/15* (2013.01); *G01N 33/442* (2013.01); *G01N 33/49* (2013.01); *A61B 2562/0233* (2013.01); *A61B 2562/0238* (2013.01); *A61B 2562/146* (2013.01); *A61B 2576/02* (2013.01); *G01J 3/1838* (2013.01); *G01J 2003/104* (2013.01); *G01J 2003/1208* (2013.01); *G01J 2003/2826* (2013.01); *G01M 3/38* (2013.01); *G01N 21/85* (2013.01); *G01N 21/9508* (2013.01); *G01N 2021/3595* (2013.01); *G01N 2021/399* (2013.01); *G01N 2201/061* (2013.01); *G01N 2201/062* (2013.01); *G01N 2201/06113* (2013.01); *G01N 2201/08* (2013.01); *G01N 2201/12* (2013.01); *G01N 2201/129* (2013.01); *H01S 3/0092* (2013.01); *H01S 3/06758* (2013.01); *H01S 3/302* (2013.01)

(58) Field of Classification Search
USPC ...................................................... 356/300
See application file for complete search history.

(56) References Cited

U.S. PATENT DOCUMENTS

| | | |
|---|---|---|
| 4,221,997 A | 9/1980 | Flemming |
| 4,275,266 A | 6/1981 | Lasar |
| 4,374,618 A | 2/1983 | Howard |
| 4,403,605 A | 9/1983 | Tanikawa |
| 4,462,080 A | 7/1984 | Johnstone et al. |
| 4,516,207 A | 5/1985 | Moriyama et al. |
| 4,523,884 A | 6/1985 | Clement et al. |
| 4,605,080 A | 8/1986 | Lemelson |
| 4,641,292 A | 2/1987 | Tunnell et al. |
| 4,704,696 A | 11/1987 | Reimer et al. |
| 4,728,974 A | 3/1988 | Nio et al. |
| 4,762,455 A | 8/1988 | Coughlan et al. |
| 4,776,016 A | 10/1988 | Hansen |
| 4,958,910 A | 9/1990 | Taylor et al. |
| 4,989,253 A | 1/1991 | Liang et al. |
| 5,078,140 A | 1/1992 | Kwoh |
| 5,084,880 A | 1/1992 | Esterowitz et al. |
| 5,086,401 A | 2/1992 | Glassman et al. |
| 5,134,620 A | 7/1992 | Huber |
| 5,142,930 A | 9/1992 | Allen et al. |
| 5,180,378 A | 1/1993 | Kung et al. |
| 5,191,628 A | 3/1993 | Byron |
| 5,218,655 A | 6/1993 | Mizrahi |
| 5,230,023 A | 7/1993 | Nakano |
| 5,246,004 A | 9/1993 | Clarke et al. |
| 5,267,152 A | 11/1993 | Yang et al. |
| 5,267,256 A | 11/1993 | Saruwatari et al. |
| 5,267,323 A | 11/1993 | Kimura |
| 5,300,097 A | 4/1994 | Lerner et al. |
| 5,303,148 A | 4/1994 | Mattson et al. |
| 5,305,427 A | 4/1994 | Nagata |
| 5,313,306 A | 5/1994 | Kuban et al. |
| 5,323,404 A | 6/1994 | Grubb |
| 5,345,538 A | 9/1994 | Narayannan et al. |
| 5,368,224 A | 11/1994 | Richardson et al. |
| 5,400,165 A | 3/1995 | Gnauck et al. |
| 5,408,409 A | 4/1995 | Glassman et al. |
| 5,458,122 A | 10/1995 | Hethuin |
| 5,497,769 A | 3/1996 | Gratton et al. |
| 5,544,654 A | 8/1996 | Murphy et al. |
| 5,563,710 A | 10/1996 | Webb et al. |
| 5,572,999 A | 11/1996 | Funda et al. |
| 5,617,871 A | 4/1997 | Burrows |
| 5,631,758 A | 5/1997 | Knox et al. |
| 5,687,734 A | 11/1997 | Dempsey et al. |
| 5,695,493 A | 12/1997 | Nakajima et al. |
| 5,696,778 A | 12/1997 | MacPherson |
| 5,704,351 A | 1/1998 | Mortara et al. |
| 5,718,234 A | 2/1998 | Warden et al. |
| 5,746,206 A | 5/1998 | Mannheimer |
| 5,747,806 A | 5/1998 | Khalil et al. |
| 5,748,103 A | 5/1998 | Flach et al. |
| 5,774,213 A | 6/1998 | Trebino et al. |
| 5,792,204 A | 8/1998 | Snell |
| 5,795,300 A | 8/1998 | Bryars |
| 5,812,978 A | 9/1998 | Nolan |
| 5,855,550 A | 1/1999 | Lai et al. |
| 5,862,803 A | 1/1999 | Besson et al. |
| 5,867,305 A | 2/1999 | Waarts et al. |
| 5,912,749 A | 6/1999 | Harstead et al. |
| 5,919,134 A | 7/1999 | Diab |
| 5,944,659 A | 8/1999 | Flach et al. |
| 5,950,629 A | 9/1999 | Taylor et al. |
| 5,957,854 A | 9/1999 | Besson et al. |
| 5,970,457 A | 10/1999 | Brant et al. |
| 6,014,249 A | 1/2000 | Fermann et al. |
| 6,031,603 A | 2/2000 | Fine et al. |
| 6,043,927 A | 3/2000 | Islam |
| 6,044,283 A | 3/2000 | Fein et al. |
| 6,078,833 A | 6/2000 | Hueber |
| 6,115,673 A | 9/2000 | Malin et al. |
| 6,181,414 B1 | 1/2001 | Raz et al. |
| 6,185,535 B1 | 2/2001 | Hedin et al. |
| 6,200,309 B1 | 3/2001 | Rice et al. |
| 6,212,310 B1 | 4/2001 | Waarts et al. |
| 6,224,542 B1 | 5/2001 | Chang et al. |
| 6,246,707 B1 | 6/2001 | Yin et al. |
| 6,246,896 B1 | 6/2001 | Dumoulin et al. |
| 6,273,858 B1 | 8/2001 | Fox et al. |
| 6,278,975 B1 | 8/2001 | Brant et al. |
| 6,281,471 B1 | 8/2001 | Smart |
| 6,285,897 B1 | 9/2001 | Kilcoyne et al. |
| 6,289,238 B1 | 9/2001 | Besson et al. |
| 6,301,271 B1 | 10/2001 | Sanders et al. |
| 6,301,273 B1 | 10/2001 | Sanders et al. |
| 6,325,978 B1 | 12/2001 | Labuda et al. |
| 6,333,803 B1 | 12/2001 | Kurotori et al. |
| 6,337,462 B1 | 1/2002 | Smart |
| 6,340,806 B1 | 1/2002 | Smart et al. |
| 6,350,261 B1 | 2/2002 | Domankevitz et al. |
| 6,364,834 B1 | 4/2002 | Reuss et al. |
| 6,374,006 B1 | 4/2002 | Islam et al. |
| 6,381,391 B1 | 4/2002 | Islam et al. |
| 6,402,691 B1 | 6/2002 | Peddicord et al. |
| 6,407,853 B1 | 6/2002 | Samson et al. |
| 6,436,107 B1 | 8/2002 | Wang et al. |
| 6,441,747 B1 | 8/2002 | Khair et al. |
| 6,442,430 B1 | 8/2002 | Ferek-Petric |
| 6,443,890 B1 | 9/2002 | Schulze et al. |
| 6,450,172 B1 | 9/2002 | Hartlaub et al. |
| 6,453,201 B1 | 9/2002 | Daum et al. |
| 6,454,705 B1 | 9/2002 | Cosentino et al. |
| 6,458,120 B1 | 10/2002 | Shen et al. |
| 6,462,500 B1 | 10/2002 | L'Hegarat et al. |
| 6,463,361 B1 | 10/2002 | Wang et al. |
| 6,480,656 B1 | 11/2002 | Islam et al. |
| 6,505,133 B1 | 1/2003 | Hanna et al. |
| 6,509,566 B1 | 1/2003 | Wamsley et al. |
| 6,512,936 B1 | 1/2003 | Monfre et al. |
| 6,534,012 B1 | 3/2003 | Hazen et al. |
| 6,549,702 B2 | 4/2003 | Islam et al. |
| 6,567,431 B2 | 5/2003 | Tabirian et al. |
| 6,587,702 B1 | 7/2003 | Ruchti et al. |
| 6,603,910 B2 | 8/2003 | Islam et al. |
| 6,605,080 B1 | 8/2003 | Altshuler et al. |
| 6,611,643 B2 | 8/2003 | Birk et al. |
| 6,619,835 B2 | 9/2003 | Kita |
| 6,625,180 B2 | 9/2003 | Bufetov et al. |
| 6,631,025 B2 | 10/2003 | Islam et al. |
| 6,640,117 B2 | 10/2003 | Makarewicz et al. |
| 6,659,947 B1 | 12/2003 | Carter et al. |
| 6,659,999 B1 | 12/2003 | Anderson et al. |
| 6,701,170 B2 | 3/2004 | Stetson |
| 6,708,048 B1 | 3/2004 | Chance |
| 6,731,967 B1 | 5/2004 | Turcott |
| 6,738,652 B2 | 5/2004 | Mattu et al. |
| 6,760,148 B2 | 7/2004 | Islam |
| 6,773,922 B2 | 8/2004 | Jeng et al. |
| 6,788,965 B2 | 9/2004 | Ruchti et al. |
| 6,802,811 B1 | 10/2004 | Slepian |
| 6,816,241 B2 | 11/2004 | Grubisic |
| 6,847,336 B1 | 1/2005 | Lemelson et al. |
| 6,864,978 B1 | 3/2005 | Hazen et al. |
| 6,885,498 B2 | 4/2005 | Islam |
| 6,885,683 B1 | 4/2005 | Fermann et al. |
| 6,898,451 B2 | 5/2005 | Wuori |
| 6,916,096 B2 | 7/2005 | Eberl et al. |
| 6,943,936 B2 | 9/2005 | Islam et al. |
| 6,990,364 B2 | 1/2006 | Ruchti et al. |
| 7,010,336 B2 | 3/2006 | Lorenz et al. |
| 7,027,467 B2 | 4/2006 | Baev et al. |
| 7,060,061 B2 | 6/2006 | Altshuler et al. |
| 7,105,823 B2 | 9/2006 | Abrahamsson et al. |
| 7,133,710 B2 | 11/2006 | Acosta et al. |
| 7,167,300 B2 | 1/2007 | Fermann et al. |
| 7,184,148 B2 | 2/2007 | Alphonse |
| 7,209,657 B2 | 4/2007 | Islam |
| 7,233,816 B2 | 6/2007 | Blank et al. |
| 7,259,906 B1 | 8/2007 | Islam |
| 7,263,288 B1 | 8/2007 | Islam |
| 7,278,966 B2 | 10/2007 | Hjelt et al. |
| 7,294,105 B1 | 11/2007 | Islam |
| 7,299,080 B2 | 11/2007 | Acosta et al. |
| 7,317,938 B2 | 1/2008 | Lorenz et al. |

(56) References Cited

U.S. PATENT DOCUMENTS

| | | |
|---|---|---|
| 7,318,909 B2 | 1/2008 | Lehmann et al. |
| 7,332,784 B2 | 2/2008 | Mills et al. |
| 7,356,364 B1 | 4/2008 | Bullock et al. |
| 7,395,158 B2 | 7/2008 | Monfre et al. |
| 7,433,116 B1 | 10/2008 | Islam |
| 7,468,036 B1 | 12/2008 | Rulkov et al. |
| 7,519,253 B2 | 4/2009 | Islam |
| 7,519,406 B2 | 4/2009 | Blank et al. |
| 7,620,674 B2 | 11/2009 | Ruchti et al. |
| 7,648,463 B1 | 1/2010 | Elhag et al. |
| 7,697,966 B2 | 4/2010 | Monfre et al. |
| 7,771,320 B2 | 8/2010 | Riley et al. |
| 7,787,503 B2 | 8/2010 | Wadsworth |
| 7,787,924 B2 | 8/2010 | Acosta et al. |
| 7,800,818 B2 | 9/2010 | Mattsson |
| 7,807,718 B2 | 10/2010 | Hashim et al. |
| 7,847,234 B2 | 12/2010 | Meyers et al. |
| 7,848,605 B2 | 12/2010 | Ridder et al. |
| 7,890,158 B2 | 2/2011 | Rowe et al. |
| 8,000,574 B2 | 8/2011 | Buchter et al. |
| 8,145,286 B2 | 3/2012 | Arai et al. |
| 8,157,730 B2 | 4/2012 | LeBoeuf et al. |
| 8,158,175 B2 | 4/2012 | Bourg, Jr. |
| 8,158,493 B2 | 4/2012 | Shah et al. |
| 8,172,761 B1 | 5/2012 | Rulkov et al. |
| 8,180,422 B2 | 5/2012 | Rebec |
| 8,180,591 B2 | 5/2012 | Yuen et al. |
| 8,198,589 B2 | 6/2012 | Tolton et al. |
| 8,213,007 B2 | 7/2012 | Wang et al. |
| 8,310,336 B2 | 11/2012 | Muhsin et al. |
| 8,315,682 B2 | 11/2012 | Such et al. |
| 8,430,310 B1 | 4/2013 | Ho et al. |
| 8,463,576 B2 | 6/2013 | Yuen et al. |
| 8,472,108 B2 | 6/2013 | Islam |
| 8,475,367 B1 | 7/2013 | Yuen et al. |
| 8,509,882 B2 | 8/2013 | Albert et al. |
| 8,649,838 B2 | 2/2014 | Chen et al. |
| RE44,875 E | 4/2014 | Kiani et al. |
| 8,725,226 B2 | 5/2014 | Isaacson |
| 8,755,871 B2 | 6/2014 | Weng et al. |
| 8,767,190 B2 | 7/2014 | Hall |
| 8,788,002 B2 | 7/2014 | LeBoeuf et al. |
| 8,945,017 B2 | 2/2015 | Venkatraman et al. |
| 8,948,832 B2 | 2/2015 | Hong et al. |
| 8,954,135 B2 | 2/2015 | Yuen et al. |
| 9,142,117 B2 | 9/2015 | Muhsin et al. |
| 9,164,032 B2 | 10/2015 | Islam |
| 9,179,876 B2 | 11/2015 | Ochs et al. |
| 9,192,329 B2 | 11/2015 | Al-Ali |
| 9,207,121 B2 | 12/2015 | Adler |
| 9,241,676 B2 | 1/2016 | Lisogurski et al. |
| 9,326,712 B1 | 5/2016 | Kiani |
| 9,596,990 B2 | 3/2017 | Park et al. |
| 9,651,533 B2 | 5/2017 | Islam |
| 9,675,250 B2 | 6/2017 | Tverskoy |
| 9,723,993 B2 | 8/2017 | Vermeulen |
| 9,757,040 B2 | 9/2017 | Islam |
| 9,820,658 B2 | 11/2017 | Tran |
| 9,861,286 B1 | 1/2018 | Islam |
| 9,885,698 B2 | 2/2018 | Islam |
| 10,188,299 B2 | 1/2019 | Islam |
| 10,213,113 B2 | 2/2019 | Islam |
| 2002/0013518 A1 | 1/2002 | West et al. |
| 2002/0019584 A1 | 2/2002 | Schulze et al. |
| 2002/0032468 A1 | 3/2002 | Hill et al. |
| 2002/0082612 A1 | 6/2002 | Moll et al. |
| 2002/0109621 A1 | 8/2002 | Khair et al. |
| 2002/0115914 A1 | 8/2002 | Russ |
| 2002/0128846 A1 | 9/2002 | Miller |
| 2002/0178003 A1 | 11/2002 | Gehrke et al. |
| 2003/0022126 A1 | 1/2003 | Buchalla et al. |
| 2003/0107739 A1 | 6/2003 | Lehmann et al. |
| 2003/0109055 A1 | 6/2003 | Lehmann et al. |
| 2003/0152307 A1 | 8/2003 | Von Drasek et al. |
| 2004/0174914 A1 | 9/2004 | Fukatsu |
| 2004/0240037 A1 | 12/2004 | Harter |
| 2005/0049468 A1 | 3/2005 | Carlson et al. |
| 2005/0111500 A1 | 5/2005 | Harter et al. |
| 2005/0133691 A1 | 6/2005 | Doppke et al. |
| 2005/0209516 A1 | 9/2005 | Fraden |
| 2006/0058683 A1 | 3/2006 | Chance |
| 2006/0198397 A1 | 9/2006 | Korolev et al. |
| 2006/0223032 A1 | 10/2006 | Fried et al. |
| 2006/0245461 A1 | 11/2006 | Islam |
| 2006/0268393 A1 | 11/2006 | Islam |
| 2006/0281982 A1 | 12/2006 | Grata et al. |
| 2006/0283931 A1 | 12/2006 | Polli et al. |
| 2007/0021670 A1 | 1/2007 | Mandelis et al. |
| 2007/0078348 A1 | 4/2007 | Holman |
| 2008/0086318 A1 | 4/2008 | Gilley et al. |
| 2008/0105665 A1 | 5/2008 | Kondo |
| 2008/0240502 A1 | 10/2008 | Freedman et al. |
| 2009/0028193 A1 | 1/2009 | Islam |
| 2009/0105605 A1 | 4/2009 | Abreu |
| 2009/0156932 A1 | 6/2009 | Zharov |
| 2009/0185274 A1 | 7/2009 | Shpunt |
| 2009/0204110 A1 | 8/2009 | Islam |
| 2009/0244288 A1 | 10/2009 | Fujimoto et al. |
| 2009/0287067 A1 | 11/2009 | Dorogusker et al. |
| 2010/0007717 A1 | 1/2010 | Spektor et al. |
| 2010/0046067 A1 | 2/2010 | Fermann et al. |
| 2010/0118123 A1 | 5/2010 | Freedman et al. |
| 2010/0160794 A1 | 6/2010 | Banet et al. |
| 2010/0160798 A1 | 6/2010 | Banet et al. |
| 2010/0217099 A1 | 8/2010 | LeBoeuf et al. |
| 2010/0217102 A1 | 8/2010 | LeBoeuf et al. |
| 2010/0284082 A1 | 11/2010 | Shpunt et al. |
| 2010/0322490 A1 | 12/2010 | Pan et al. |
| 2010/0331637 A1 | 12/2010 | Ting et al. |
| 2011/0040197 A1 | 2/2011 | Welch et al. |
| 2011/0143364 A1 | 6/2011 | Kim et al. |
| 2011/0188054 A1 | 8/2011 | Petronius et al. |
| 2011/0208015 A1 | 8/2011 | Welch et al. |
| 2011/0237911 A1 | 9/2011 | Lamego et al. |
| 2011/0267688 A1 | 11/2011 | Kleppe et al. |
| 2011/0282167 A1 | 11/2011 | Ridder et al. |
| 2011/0292376 A1 | 12/2011 | Kukushkin et al. |
| 2012/0013722 A1 | 1/2012 | Wong et al. |
| 2012/0041767 A1 | 2/2012 | Hoffman et al. |
| 2012/0197093 A1 | 8/2012 | LeBoeuf et al. |
| 2012/0203077 A1 | 8/2012 | He et al. |
| 2012/0239013 A1 | 9/2012 | Islam |
| 2012/0245439 A1 | 9/2012 | Andre et al. |
| 2012/0310062 A1 | 12/2012 | Li et al. |
| 2012/0316455 A1 | 12/2012 | Rahman et al. |
| 2013/0274569 A1 | 10/2013 | Islam |
| 2013/0281795 A1 | 10/2013 | Varadan |
| 2013/0303921 A1 | 11/2013 | Chu et al. |
| 2013/0327966 A1 | 12/2013 | Fidler et al. |
| 2014/0078510 A1 | 3/2014 | Rubio Guivernau et al. |
| 2014/0081100 A1 | 3/2014 | Muhsin et al. |
| 2014/0236021 A1 | 8/2014 | Islam |
| 2014/0249427 A1 | 9/2014 | Liu |
| 2014/0275852 A1 | 9/2014 | Hong et al. |
| 2014/0275854 A1 | 9/2014 | Venkatraman et al. |
| 2015/0011851 A1 | 1/2015 | Mehta et al. |
| 2015/0338509 A1 | 11/2015 | Lange |
| 2016/0045118 A1 | 2/2016 | Kiani |
| 2016/0327476 A1 | 11/2016 | Islam |
| 2018/0231373 A1 | 8/2018 | Pesach et al. |

FOREIGN PATENT DOCUMENTS

| | | |
|---|---|---|
| DE | 102010012987 A1 | 10/2010 |
| EP | 1148666 A2 | 10/2001 |
| JP | 2005270544 A | 10/2005 |
| WO | 1997015240 A1 | 5/1997 |
| WO | 1997049340 A1 | 12/1997 |
| WO | 2001050959 A1 | 7/2001 |
| WO | 2001089362 A2 | 11/2001 |
| WO | 2002027640 A2 | 4/2002 |
| WO | 2002028123 A2 | 4/2002 |
| WO | 2005013843 A2 | 2/2005 |
| WO | 2007061772 A1 | 5/2007 |

(56) References Cited

FOREIGN PATENT DOCUMENTS

| WO | 2009130464 A1 | 10/2009 |
|---|---|---|
| WO | 2012135952 A1 | 10/2012 |
| WO | 2013012938 A1 | 1/2013 |
| WO | 2015084376 A1 | 6/2015 |

OTHER PUBLICATIONS

Inter Partes Review No. IPR2020-00209; Petition for Inter Partes Review of U.S. Pat. No. 10,213,113; *Apple Inc.* v. *Omni Medsci, Inc.*; pp. 1-91; dated Dec. 11, 2019.
File History for U.S. Pat. No. 10,213,113 issued Feb. 26, 2019, 686 pps.
Declaration of Brian W. Anthony, PhD, regarding U.S. Pat. No. 10,213,113 in IPR2020-00209, Dec. 11, 2019, 101 pps.
United States District Court Eastern District of Texas Marshall Division; *Omni Medsci, Inc.* vs. *Apple Inc.*; Civil Action No. 2:18-cv-00429; Second Amended Complaint; Feb. 26, 2019; 274 pps.
United States District Court Northern District of California Oakland Division;*Omni Medsci, Inc.* vs. *Apple Inc.*; Civil Action No. 19-cv-05673-YGR; Order staying the case; Nov. 20, 2019, 5 pps.
File History for U.S. Pat. No. 10,188,299 issued Jan. 29, 2019, 787 pps.
Declaration of Brian W. Anthony, PhD, regarding U.S. Pat. No. 10,188,299 in IPR2020-00175, Dec. 11, 2019, 119 pps.
United States District Court Eastern District of Texas Marshall Division; *Omni Medsci, Inc.* vs. *Apple Inc.*; Civil Action No. 2:18-cv-429; Amended Complaint; Jan. 28, 2019; 169 pps.
Claim Construction Memorandum Opinion and Order. Case No. 2:18-CV-000134-RWS (Jun. 24, 2019).
Claim Construction Memorandum Opinion and Order. Case No. 2:18-CV-000429-RWS (Aug. 14, 2019).
Declaration of Brian W. Anthony, PhD regarding U.S. Pat. No. 10,098,546 filed in IPR2020-00029 (Oct. 17, 2019).
Declaration of Brian W. Anthony, PhD regarding U.S. Pat. No. 9,651,533 filed in IPR2019-00913 (Apr. 10, 2019).
Declaration of Brian W. Anthony, PhD regarding U.S. Pat. No. 9,651,533 filed in IPR2019-00916 (Apr. 10, 2019).
Declaration of Brian W. Anthony, PhD regarding U.S. Pat. No. 9,757,040 filed in IPR2019-00910 (Apr. 10, 2019).
Declaration of Brian W. Anthony, PhD regarding U.S. Pat. No. 9,757,040 filed in IPR2019-00917 (Apr. 10, 2019).
Declaration of Brian W. Anthony, PhD regarding U.S. Pat. No. 9,861,286 filed in IPR2019-00911 (Apr. 10, 2019).
Declaration of Brian W. Anthony, PhD regarding U.S. Pat. No. 9,861,286 filed in IPR2019-00914 (Apr. 10, 2019).
Declaration of Brian W. Anthony, PhD regarding U.S. Pat. No. 9,885,698 filed in IPR2019-00912 (Apr. 10, 2019).
Declaration of Brian W. Anthony, PhD regarding U.S. Pat. No. 9,885,698 filed in IPR2019-00915 (Apr. 10, 2019).
File History for U.S. Pat. No. 10,098,546, issued Oct. 16, 2018.
Inter Partes Review No. IPR2020-00029; Petition for Inter Partes Review of U.S. Pat. No. 10,098,546; *Apple Inc.* v. *Omni Medsci, Inc.*; dated Oct. 17, 2019.
Lister et al., Optical properties of human skin (Journal of Biomedical Optics 2012).
Mark Nelson & Jean-Loup Gailly, The Data Compression Book (Cary Sullivan et al. eds.) (2nd ed. 1996).
Newton, H., Newton's Telecom Dictionary (18th ed. 2002).
Order, *Omni MedSci, Inc.* v. *Apple Inc.*, No. 2:18-cv-134-RWS in the United States District Court for the Eastern District of Texas Marshall Division (Aug. 16, 2019), ECF No. 283.
Proof of Service of Summons in *Omni MedSci, Inc.* v. *Apple Inc.*, No. 2:18-cv-429 (E.D. Tex.).
Aaviksoo, J., et al., "Observation of optical precursors at pulse propagation in GaAs", Physical Review A, vol. 44, No. 9, Nov. 1, 1991, pp. R5353-R5356.
Abeeluck, Akheelesh K., et al., "Continuous-wave pumping in the anomalous- and normal dispersion regimes of nonlinear fibers for supercontinuum generaffon", Optics Letters, vol. 30, No. 1, Jan. 1, 2005, pp. 61-63.
Absorption Coefficient and Penetration Depth, The Science of Solar, available at https://photon.libretexts.org/The_Science_of_Solar/Solar_Basics/C._Semico-nductors_and_Solar_Interactions/III._Absorption_of_Light_and_Generation/1.-_Absorption_Coefficient_and_Penetration_Depth (Last Updated Nov. 3, 2018).
Akbari, H. K. Uto, Y. Kosugi, K. Kojima, N. Tanaka, "Cancer detection using infrared hyperspectral imaging," Cancer Science, vol. 102, No. 4, pp. 852-857 (Apr. 2011).
Amended Joint Claim Construction and Prehearing Statement filed in Case No. 2:18-cv-134-RWS (Dkt. #102) (Jan. 11, 2019).
Analysis of Edible Oils Using FT-NIR Spectroscopy. Bruker Optics, www.azom.com/article.aspx?ArticleID=5981, Mar. 10, 2012.
Andreoli, G. B. Bulgarelli, B. Hosgood, D. Tarchi, "Hyperspectral analysis of oil and oil-impacted soils for remote sensing purposes," Institute for the Protection and Security of the Citizen, European Commission Joint Research Centre, EUR 22739 EN (Mar. 2007).
Apple Inc.'s Preliminary Claim Constructions and Extrinsic Evidence Pursuant to Patent Local Rule 4-2 served in Case No. 2:18-cv-134-RWS (Nov. 1, 2018).
Application Brief the role of infrared microprobe analysis in forensic drug analysis, www.smithsdetection.com, Jun. 27, 2005.
Aris, Ishak Bin, "An Internet-Based Blood Pressure Monitoring System for Patients"; Journal of Telemedicine and Telecare 2001; pp. 51-53.
Arnold, T., M. De Biasio, R. Leitner, "Near-Infrared Imaging Spectroscopy for Counterfeit Drug Detection," Next Generation Spectroscopic Technologies IV, edited by M. A. Druy, R.A. Crocombe, Proceedings of SPIE, vol. 8032, 80320Y-1 to 7, (2011).
Asada et al., Mobile Monitoring with Wearable Photoplethysmographic Biosensors, Technical and Clinical Aspects of a Ring Sensor for Ambulatory, Telemetric, Continuous Health Monitoring in the Field, in the Hospital, and in the Home, IEEE Engineering in Medicine and Biology Magazine, (May/Jun. 2003) 13 pages.
Asada et al., The MIT Ring: History, Technology, and Challenges of Wearable Health Monitoring, MIT Industrial Liaison Program (2010) R&D Conference, MA, 72 pages.
Asada; Charts 1-3: Asada-533; U.S. Pat. No. 9,651,533 vs. Asada; *Omni MedSci, Inc.* v. *Apple Inc.*, pp. 1-188; May 22, 2019.
Asare et al., Analysis of Multi-Spectral Photoplethysmograph Biosensors, Proc. SPIE 8801, Novel Biophotonic Techniques and Applications II, 880106 (Jun. 2013), European Conferences on Biomedical Optics, Munich, Germany, 7 pages.
Asobe, Masaki, "Nonlinear Optical Properties of Chalcogenide Glass Fibers and Their Application to All-Optical Switching", Optical Fiber Technology, vol. 3, Article No. OF970214, 1997, pp. 142-148.
Asobe, Masaki, et al., "Third-order nonlinear spectroscopy in As2S3 chalcogenide glass fibers", J. Appl. Phys. 77 (11), Jun. 1, 1995, pp. 5518-5523.
Avdokhin, A. V. et al, "Continuous-wave, high-power, Raman continuum generation in holey fibers", Optics Letters, vol. 28, No. 15, Aug. 1, 2003, pp. 1353-1355.
Ayvaz, Huseyin, et al. "Application of infrared microspectroscopy and chemometric analysis for screening the acrylamide content in potato chips." Analytical Methods 5.8 (2013): 2020-2027.
B. Rigas, P.T.T. Wong, "Human Colon Adenocarcinoma Cell Lines Display Infrared Spectroscopic Features," Cancer Research, Jan. 1, 1992, pp. 84-88.
Barolet, Daniel, Light-Emitting Diodes (LEDs) in Dermatology, Seminars in Cutaneous Medicine and Surgery 27:227-238 (2008).
Bashkatov, A., et al., Optical properties of human skin, subcutaneous and mucous tissues in the wavelength range from 400 to 2000 nm, Journal of Physics D: Applied Physics 38 (2005) 2543-2555.
Baum P., et al., Strategic Intelligence Monitor on Personal Health Systems, Phase 2: Market Developments—Remote Patient Monitoring and Treatment, Telecare, Fitness/Wellness and mHealth, JRC Scientific and Policy Reports of European Commission (2013).

(56) References Cited

OTHER PUBLICATIONS

Beck, Mattias, et al., "Continuous Wave Operation of a Mid-Infrared Semiconductor Laser at Room Temperature," Science vol. 295, www.sciencemag.org, Jan. 11, 2002, pp. 301-305.

Belikov, A.V., A.V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).

Bellisola, G. C. Sorio, "Infrared spectroscopy and microscopy in cancer research and diagnosis," American Journal of Cancer Research, vol. 2, No. 1, pp. 1-21 (2012).

Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.

Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A.V. Priezzhev and G.L. Cote, Editors, Proceedings of SPIE, vol. 4624, pp. 1019 (2002).

Boppart, Stephen A., et al., "Imaging developing neural morphology using optical coherence tomography", Journal of Neuroscience Methods 70, 1996, pp. 65-72.

Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.

Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).

Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).

Borlinghaus, R.T., L. Kuschel, "White Light Laser: The Ultimate Source for Confocal Microscopy," http://www.leica-microsystems.com/science-lab/white-light-laser (Jun. 27, 2012).

Borrelli, N. F., et al., "Resonant and non-resonant effects in photonic glasses", Journal of Non-Crystalline Solids 185, 1995, pp. 109-122.

Boult, Maggi, et aL, "Percutaneous Endoscopic Laser Discectomy", Systematic Review, Aust. N.Z.J. Surg., vol. 70, Apr. 7, 2000, pp. 475-479.

Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.

Branche et al., Signal Quality and Power Consumption of a New Prototype Reflectance Pulse Oximeter Sensor, Proceedings of the IEEE 31st Annual Northeast Bioengineering Conference (2005), Hoboken, NJ, 2 pages.

Bronzino, Joseph D.; "The Biomedical Engineering Handbook", (1995).

Büning-Pfaue, Hans. "Analysis of water in food by near infrared spectroscopy." Food Chemistry 82.1 (2003): 107-115.

Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).

Busse, Lynda E., et al., "Design Parameters for Fluoride Multimode Fibers", Journal of Lightwave Technology, vol. 9, No. 7, Jul. 1991, pp. 828-831.

Buttussi, F., et al., MOPET: A context-aware and user-adaptive wearable system for fitness training, Artificial Intelligence in Medicine (2008) 42, 153-163.

Cai et al., Implementation of a Wireless Pulse Oximeter Based on Wrist Band Sensor, College of Biological Science and Medical Engineering Southeast University, (2010) 3rd International Conference on Biomedical Engineering and Informatics, Nanjing, China, 4 pages.

Camacho, Nancy P., et al., "FTIR Microscopic Imaging of Collagen and Proteoglycan in Bovine Cartilage," Biopolymers (Biospectroscopy), vol. 62, 2001, pp. 1-8.

Cardinal, T., et al., "Non-linear optical properties of chalcogenide glasses in the system As—S—Se", Journal of Non-Crystalline Solids 256 & 257, 1999, pp. 353-360.

Champert, Pierre-Alain, et al., "White-light supercontinuum generation in normally dispersive optical fiber using original multi-wavelength pumping system", Optics Express, vol. 12, No. 19, Sep. 20, 2004, pp. 4366-4371.

Choi, Joon Y., et al, "Thermal, Mechanical, Optical, and Morphologic Changes in Bovine Nucleus Pulposus Induced by Nd:YAG ($\lambda$=1.32 um) Laser Irradiation", Lasers in Surgery and Medicine, vol. 28, 2001, pp. 248-254.

Choi, Seung-Ho, et al., "Observation of Optical Precursors in Water", Physical Review Letters, vol. 92, No. 19, May 14, 2004, pp. 193903-1-193903-.3.

Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).

Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).

Clark, R.N., J.M. Curchin, T. M. Hoefen, G.A. Swayze, "Reflectance Spectroscopy of organic compounds: 1. Alkanes," Journal of Geophysical Research, vol. 114, pp. E03001 1 to E03001 19, (2009).

Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.

Compendium of Chemical Terminology Gold Book, International Union of Pure and Applied Chemistry, Version 2.3.3 (Feb. 24, 2014).

Computer Motion, Inc. "HERMES™ O.R. Control Center-510(k) Summary of Safety and Effectiveness," Oct. 11, 2002, 5 pages.

Computer Motion, Inc., "501(k) Summary-ZEUS® MicroWrist™ Surgical System and Accessories," Sep. 24, 2002, 6 pages.

Curriculum Vitae of Brian W. Anthony, PhD (Nov. 18, 2018).

D'Amico, Anthony V., et al., "Optical Coherence Tomography as a Method for Identifying Benign and Malignant Microscopic Structures in the Prostate Gland", Basic Science, Urology 55 (5), 2000, pp. 783-787.

De Boer, Johannes F., et al., "Determination of the depth-resolved Stokes parameters of light backscattered from turbid media by use of polarization-sensitive optical coherence omography", Optics Letters, vol. 24, No. 5; Mar. 1, 1999, pp. 300-302.

De Boer, Johannes F., et al., "Imaging thermally damaged tissue by polarization sensitive optical coherence tomography", Optics Express 212, vol. 3, No. 6, Sep. 14, 1998, pp. 212-218.

Demircan, Ayhan, et al., "Supercontinuum generation by the modulation instability", Optics Communications 244, 2005, pp. 181-185.

Desthieux, B., et al., "111 ?W (0. 5 mJ) pulse amplification at 1.5 um using a gated cascade of three erbium-doped fiber amplifiers," Appl. Phys. Lett. vol. 63, Aug. 2, 1993, pp. 586-588.

District Court Preliminary Claim Constructions in Case No. 2:18-cv-134-RWS from Court at Markman hearing.

Dr. Mohammed Islam, Faculty Profile, University of Michigan, College of Engineering (available at https://islam.engin.umich.edu) (2019 The Regents of the University of Michigan).

Drexler, C., Hirmer, M., Danilov, S., Giglberger, S., Putzger, J., Niklas, A., Jager, A., Hiller, K., Loffler, S., Schmalz, G., Redlich, B., Schulz, I., Monkman, G., Ganichev, S. "Infrared spectroscopy for clinical diagnosis of dental pulp vitality." Infrared, Millimeter, and Terahertz Waves (IRMMW-THz), 2012 37th International Conference on. IEEE (2012).

(56) References Cited

OTHER PUBLICATIONS

Drexler, Wolfgang, "Ultrahigh-resolution optical coherence tomography", Journal of Biomedical Optics, vol. 9, No. 1, Jan./Feb. 2004, pp. 47-74.

Dubois, A., et al., "Three-dimensional cellular-level imaging using full-field optical coherence tomography", Physics in Medicine and Biology, Phys. Med. Biol. 49, 2004, pp. 1227-1234.

Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.

Edwards, Glenn S., et al., "Advantage of the Mark-III FEL for biophysical research and biomedical applications", J. Synchrotron Rad. vol. 10, 2003, pp. 354-357.

Edwards, Glenn, et al., Tissue ablation by a free-electron laser tuned to the amide II band, Nature, vol. 371, Sep. 29, 1994, pp. 416-419.

Embedded-Lab, Introducing Easy Pulse: A DIY Photoplethysmographic Sensor for Measuring Hearth Rate, posted on www.Embedded-Lab.com Sep. 12, 2012, by R-B, 10 pages.

Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).

Evers, D.J., B.H.W. Hendriks, G.W. Lucassen, T.J.M. Ruers, "Optical spectroscopy: current advances and future applications in cancer diagnosis and therapy," Future Oncology, vol. 8, No. 3, pp. 307-320 (2012).

Evers, D.J., R. Nachabe, H.M. Klomp, J.W. van Sandick, M.W. Wouters, G.W. Lucassen, B.H.W. Hendriks, J. Wesseling, T.J.M. Ruers, "Diffuse reflectance spectroscopy: a new guidance tool for improvement of biopsy procedures in lung malignancies," Clinical Lung Cancer, article identifier 10.1016/j.clc.2012.02.001, 8 pages, (2012).

Excerpt from Claim Construction Markman Hearing Transcript filed in Case No. 2:18-cv-134-RWS (Feb. 6, 2019) vol. 1, pp. 1, 2, 21, 22.

Excerpts from Merriam-Webster's Collegiate Dictionary Eleventh Edition (2011).

Excerpts from the American Heritage Dictionary, 5th Edition (Jul. 2012).

Extended European Search Report for European Application No. 13867874.3 dated Jul. 15, 2016.

Extended European Search Report for European Application No. 13867892.5 dated Jul. 22, 2016.

Extended European Search Report for European Application No. 17155541.0 dated May 24, 2017.

Extended European Search Report for European Application No. 17156625.0 dated Mar. 20, 2017.

F. Kuhn, K. Oppermann, B. Horig, "Hydrocarbon Index-and algorithm for hyperspectral detection of hydrocarbons," International Journal of Remote Sensing, vol. 25, No. 12, pp. 2467-2473 (Jun. 20, 2004).

Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.

Fantini, S. A. Sassaroli, "Near-infrared optical mammography for breast cancer detection with intrinsic contrast," Annals of Biomedical Engineering, vol. 40, No. 2, pp. 398-407 (Feb. 2012).

Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.

Fedotova, O., et al., "Supercontinuum generation in planar rib waveguides enabled by anomalous dispersion", Optics Express, vol. 14, No. 4, Feb. 20, 2006, pp. 1512-1517.

File History for U.S. Pat. No. 9,651,533 issued May 16, 2017.

File History for U.S. Pat. No. 9,757,040 issued Sep. 12, 2017.

File History for U.S. Pat. No. 9,861,286 issued Jan. 9, 2018.

File History for U.S. Pat. No. 9,885,698 issued Feb. 6, 2018.

Final Office Action dated Oct. 21, 2016 for U.S. Appl. No. 14/875,709.

Fried, D. M. Staninec, C.L. Darling, "Near-infrared imaging of dental decay at 1310nm," Journal of Laser Dentistry, vol. 18, No. 1, pp. 8-16 (2010).

G. Edwards, et al., "Comparison of OPA and Mark-III FEL for Tissue Ablation at 6.45 Microns," Department of Physics and Free Electron Laser Laboratory, Duke University, 2002, 7 pages.

G.S. Edwards et al., "Free-electron-laser-based biophysical and biomedical instrumentation," American Institute of Physics, vol. 74, No. 7, Jul. 2003, pp. 3207-3245.

Galvis-Sánchez, Andrea C., et al. "Fourier transform near-infrared spectroscopy application for sea salt quality evaluation." Journal of agricultural and food chemistry 59.20 (2011): 11109-11116.

GE Healthcare, GE Ohmeda TufSat Oximeter for Clinicians on the go, (2012), A General Electric Co., www.gehealthcare.com, GE, Finland, 4 pages.

GE Healthcare, TuffSat User's Guide and Service Manual Electromagnetic Compatibility (EMC), (Mar. 2005) Helsinki, Finland, 43 pages.

Genty, G., et al., "Enhanced bandwidth of supercontinuum generated m microstructured fibers", Optics Express, vol. 12, No. 15, Jul. 26, 2004, pp. 3471-3480.

Genty, G., et al., "Supercontinuum generation in large mode-area microstructured fibers", Optics Express, vol. 13, No. 21, Oct. 17, 2005, pp. 8625-8633.

Glenn Edwards, "Biomedical and potential clinical applications for pulsed lasers operating near 6.45 um," Society of Photo-Optical Instrumentation Engineers, 1995, 2 pages.

H. Harry Asada et al.; Mobile Monitoring With Wearable Photoplethysmographic Biosensors; IEEE Engineering in Medicine and Biology Magazine, Jun. 2003; 13 pps.

Haase, Norbert U. "Prediction of potato processing quality by near infrared reflectance spectroscopy of ground raw tubers" Journal of Near Infrared Spectroscopy 19.1 (2011): 37-45.

Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, 2001, pp. 33-37.

Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.

Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.

Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.

Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pp. 216-235.

Harbold, J. M., et al., "Highly nonlinear As—S—Se glasses for all-optical switching", Optics Letters, vol. 27, No. 2, Jan. 15, 2002, pp. 119-121.

Harbold, Jeffrey M., et al., "Highly Nonlinear Ge—As—Se and Ge—As—S—Se Glasses for All-Optical Switching", IEEE Photonics Technology Letters, vol. 14, No. 6, Jun. 2002, pp. 822-824.

Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).

Harrington, James A., "Infrared Fiber Optics", OSA Handbook, vol. III, white paper, to be published by McGraw Hill, Undated, 13 pages.

Hartmann, R., and H. Büning-Pfaue. "NIR determination of potato constituents." Potato research 41.4 (1998): 327-334.

Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).

(56) References Cited

OTHER PUBLICATIONS

Herranz, M., A. Ruibal, "Optical imaging in breast cancer diagnosis: the next evolution," Journal of Oncology, vol. 2012, article ID 863747, 10 pages, (2012).
Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.
Hirmer, Marion, Danilov, Sergey, Giglberger, Stephan, Putzger, Jurgen, Niklas, Andreas, Jager, Andreas, Hiller, Karl-Anton, Loffler, Susanne, Schmalz, Gottfried, Redlich, Britta, Schulz, Irene, Monkman, Gareth, Ganichev, Sergey. "Spectroscopic Study of Human Teeth and Blood from Visible to Terahertz Frequencies for Clinical Diagnosis of Dental Pulp Vitality." Journal of Infrared, Millimeter, and Terahertz Waves 33.3 (2012): 366-375.
Hirosawa, N. Y. Sakamoto, H. Katayama, S. Tonooka, K. Yano, "In vivo investigation of progressive alternations in rat mammary gland tumors by near-infrared spectroscopy," Analytical Biochemistry, vol. 305, pp. 156-165 (2002).
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.
Hori, Takashi, et al., "Flatly broadened, wideband and low noise supercontinuum generation in highly nonlinear hybrid fiber", Optics Express, vol. 12, No. 2, Jan. 26, 2004, pp. 317-324.
Humphreys et al., Noncontact Simultaneous Dual Wavelength Photoplethysmography: A Further Step Toward Noncontact Pulse Oximetry, (2007) Review of Scientific Instruments 78, 044304, American Institute of Physics, 6 pages.
Husakou, Anton V., et al, "Supercontinuum generation, four-wave mixing, and fission of higher-order solitons in photonic-crystal fibers", J. Opt. Soc. Am. B, vol. 19, No. 9, Sep. 2002, pp. 2171-2182.
I.B. Ads, A.A.E. Wagie, N.B. Mariun, A.B.E. Jammal, "An Internet-based blood pressure monitoring system for patients," Journal of Telemedicine and Telecare, 2001, pp. 51-53.
Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.
Inoue, H., et al., "Computer simulation of the vibrational spectra and properties of fluoride glasses based on ZrF4", Journal of Non-Crystalline Solids, vol. 161, 1993, pp. 118-122.
Inter Partes Review No. IPR2019-00910; Petition for Inter Partes Review of U.S. Pat. No. 9,757,040; *Apple Inc.* v. *Omni Medsci, Inc.*; pp. 1-96; dated Apr. 10, 2019.
Inter Partes Review No. IPR2019-00911; Petition for Inter Partes Review of U.S. Pat. No. 9,861,286; *Apple Inc.* v. *Omni Medsci, Inc.*; pp. 1-83; dated Apr. 10, 2019.
Inter Partes Review No. IPR2019-00912; Petition for Inter Partes Review of U.S. Pat. No. 9,885,698; *Apple Inc.* v. *Omni Medsci, Inc.*; pp. 1-94; dated Apr. 10, 2019.
Inter Partes Review No. IPR2019-00913; Petition for Inter Partes Review of U.S. Pat. No. 9,651,533; *Apple Inc.* v. *Omni Medsci, Inc.*; pp. 1-96; dated Apr. 10, 2019.
Inter Partes Review No. IPR2019-00914; Petition for Inter Partes Review of U.S. Pat. No. 9,861,286; *Apple Inc.* v. *Omni Medsci, Inc.*; pp. 1-90; dated Apr. 10, 2019.
Inter Partes Review No. IPR2019-00915; Petition for Inter Partes Review of U.S. Pat. No. 9,885,698; *Apple Inc.* v. *Omni Medsci, Inc.*; pp. 1-91; dated Apr. 10, 2019.
Inter Partes Review No. IPR2019-00916; Petition for Inter Partes Review of U.S. Pat. No. 9,651,533; *Apple Inc.* v. *Omni Medsci, Inc.*; pp. 1-90; dated Apr. 10, 2019.
Inter Partes Review No. IPR2019-00917; Petition for Inter Partes Review of U.S. Pat. No. 9,757,040; *Apple Inc.* v. *Omni Medsci, Inc.*; pp. 1-93; dated Apr. 10, 2019.
International Preliminary Report on Patentability for International Application No. PCT/US2013/07567 dated Jul. 9, 2015.
International Preliminary Report on Patentability for International Application No. PCT/US2013/075700 dated Jul. 9, 2015.
International Preliminary Report on Patentability for International Application No. PCT/US2013/075736 dated Jul. 9, 2015.
International Search Report and Written Opinion for International Application No. PCT/US2013/075700 dated Apr. 24, 2014.
International Search Report and Written Opinion for International Application No. PCT/US2013/075736 dated Apr. 7, 2014.
International Search Report and Written Opinion for International Application No. PCT/US2013/075767 dated Oct. 14, 2014.
Islam, M. N., et al., "Broad bandwidths from frequency-shifting solitons in fibers", Optics Letters, vol. 14, No. 7, Apr. 1, 1989, pp. 370-372.
Islam, M. N., et al., "Femtosecond distributed soliton spectrum in fibers", J. Opt. Soc. Am. B, vol. 6, No. 6, Jun. 1989, pp. 1149-1158.
Istepanian, Robert H., "The Comparative Performance of Mobile Telemedical Systems based on the IS-54 and GSM Cellular Telephone Standards"; Journal of Telemedicine and Telecare 1999; pp. 97-104.
J. Sanghera, I. Aggarwal, "IR Fiber Optics at NRL," undated, 10 pages.
J. Sanghera, L.B. Shaw, I.D. Aggarwal, "Applications of chalcogenide glass optical fibers," Academic of Science, 2003, pp. 1-11.
J.G. Webster; Design of Pulse Oximeters; Medical Science Series; Taylor & Francis Group; CRC Press; Oct. 23, 1997; 260 pps.
Jackson, Stuart D., et al., "Theory and numerical simulation of nth-order cascaded Raman fiber lasers", J. Opt. Soc. Am. B, vol. 18, No. 9, Sep. 2001, pp. 1297-1306.
Jarman, Richard H., "Novel optical fiber lasers", Current Opinion in Solid State and Materials Science, 1996, pp. 199-203.
Jasco Application Note No. 200DR0188-E, "Rapid Identification of illegal drug using NIR (identification of MDMA tablet)", Sep. 4, 2008.
Jung et al., Design of a Low-Power Consumption Wearable Reflectance Pulse Oximetry for Ubiquitous Healthcare System, International Conference on Control, Automation and Systems (Oct. 2008), in COEX, Seoul, Korea, 4 pages.
K.M. Joos, et al. "Optic Nerve Sheath Fenestration with a Novel Wavelength Produced by the Free Electron Laser (FEL)," Lasers in Surgery and Medicine, 27: 2000,191-205.
Karlsson, L. "Caries detection methods based on changes in optical properties between healthy and carious tissue," International Journal of Dentistry, vol. 2010, Article ID 270729, 9 pages (2010).
Kays, Sandra E., William R Windham, and Franklin E Barton. "Prediction of total dietary fiber in cereal products using near-infrared reflectance spectroscopy." Journal of Agricultural and food chemistry 44.8 (1996): 2266-2271.
Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).
Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.
Konderpati, V.R., H.M. Heise, J. Backhaus, "Recent applications of near-infrared spectroscopy in cancer diagnosis and therapy," Annals of Bioanalytic Chemistry, vol. 390, pp. 125-139 (2008).
Kowalevicz, Andrew M., et al., "Ultrahigh resolution optical coherence tomography using a superluminescent light source" Optics Express 349, vol. 10, No. 7, Apr. 8, 2002, pp. 349-353.
Krantz, M., et al., The mobile fitness coach: Towards individualized skill assessment using personalized mobile devices, Pervasive and Mobile Computing (Jun. 2012).
Kumar, V.V. Ravi Kanth, et al, "Extruded soft glass photonic crystal fiber for ultrabroad supercontinuum generation", Optics Express, vol. 10, No. 25, Dec. 16, 2002, pp. 1520-1525.
Kurylyak et al., Smartphone-Based Photoplethysmogram Measurement, Department of Electronics, Computer and System Sciences, (2012) River Publishers, University of Calabria, Italy, 30 pages.
Kutz, J. Nathan, et al., Enhanced Supercontinuum Generation through Dispersion-Management, Optics Express, vol. 13, No. 11, May 30, 2005, pp. 3989-3998.

(56) References Cited

OTHER PUBLICATIONS

Lee, Ju Han, et al., "Continuous-wave supercontinuum laser based on an erbium-doped fiber ring cavity incorporating a highly nonlinear optical fiber", Optics Letters, vol. 30, No. 19, Oct. 1, 2005, pp. 2599-2601.

Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.

Leff, D.R., O.J. Warren, L.C. Enfield, A. Gibson, T. Athanasion, D.K. Patten, J. Hebden, G.Z. Yang, A. Darzi, "Diffuse optical imaging of the healthy and diseased breast: a systematic review," Breast Cancer Research Treatment, vol. 108, pp. 9-22 (2008).

Leon-Saval, S. G., et al., "Supercontinuum generation in submicron fibre waveguides", Optics Express, vol. 12, No. 13, Jun. 28, 2004, pp. 2864-2869.

Li et al, A Wireless Reflective Pulse Oximeter with Digital Baseline Control for Unfiltered Photoplethysmograms, (Jun. 2012) IEEE Transactions on Biomedical Circuits and Systems, vol. 6, No. 3, 10 pages.

Li Xingde, et al., "Imaging needle for optical coherence tomography", Optics Letters, vol. 25, No. 20, Oct. 15, 2000, pp. 1520-1522.

Lisogurski; Charts 1-3: Lisogurski-533; U.S. Pat. No. 9,651,533 vs. Lisogurski; *Omni MedSci, Inc.* v. *Apple Inc.*, pp. 1-84; May 22, 2019.

Lucas, Jacques, "Infrared glasses", Current Opinion in Solid State & Materials Science 4, 1999. pp. 181-187.

Luo et al., A Non-Invasive Dual-Channel Oximeter Based on Near-Infrared Spectroscopy (NIRS), Biophotonics Lab, Center of Advanced Research in Photonics (2007), The Chinese University of Hong Kong, China, 2 pages.

Lussi, A., R. Hibst, R. Paulus, "Diagnodent: An optical method for caries detection," Journal of Dental Research, vol. 83, special issue C, pp. C80-C83 (2004).

M. Kumar, M.N. Islam, F.L. Terry, M.J. Freeman, A. Chan, M. Neelakandan, T. Manzur, "Stand-off detection of solid targets with diffuse reflection spectroscopy using a high-power mid-infrared supercontinuum source," Applied Optics, vol. 51, No. 15, pp. 2794-2807 (May 20, 2012).

Maia, A., L. Karlsson, W. Margulis, A. Gomes, "Evaluation of two imaging techniques: near-infrared transillumination and dental radiographs for the detection of early approximal enamel canes," Dentomaxillofacial Radiology, vol. 40, pp. 429-433 (2011).

Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).

Marbach, R., T. Koschinsky, F.A. Gries, H.M. Heise, "Noninvasive blood glucose assay by near-infrared diffuse reflectance spectroscopy of the human inner lip," Applied Spectroscopy, vol. 47, No. 7, pp. 875-881 (1993).

McCoy, R.M., J.G. Blake, K.L. Andrews, "Detecting hydrocarbon microseepage," Oil and Gas Journal, pp. 40-45 (May 28, 2001).

Mehrotra, R. A. Gupta, A. Kaushik, N. Prakash, H. Kandpal, "Infrared spectroscopic analysis of tumor pathology," Indian Journal of Experimental Biology, vol. 45, pp. 71-76 (Jan. 2007).

Mendelson et al., A Wearable Reflectance Pulse Oximeter for Remote Physiological Monitoring, (Aug./Sep. 2006) Proceedings of the 28th IEEE EMBS Annual International Conference New York City, Ny, 4 pages.

Michaels, C.A., T. Masiello, P.M. Chu, "Fourier transform spectrometry with a near-infrared supercontinuum source," Applied Spectroscopy, vol. 63, No. 5, pp. 538-543 (2009).

Mizunami, Toru, et al., "Gain saturation characteristics of Raman amplification in silica and fluoride glass optical fibers", Optics Communications 97, 1993, pp. 74-78.

Moon, Sucbei, et al., "Generation of octave-spanning supercontinuum with 1550-nm amplified diode-laser pulses and a dispersion-shifted fiber", Optics Express, vol. 14, No. 1, Jan. 9, 2006, pp. 270-278.

Morón et al, A Wireless Monitoring System for Pulse-Oximetry Sensors, (2005) Electronic Technology Department, University of Malaga, Spain, 6 pages.

Moros, J. N. Gallpienso, R. Vilches, S. Garrigues, M. DeLa Guardia, "Nondestructive direct determination of heroin in seized illicit street drugs by diffuse reflectance near-infrared spectroscopy," Analytical Chemistry, vol. 80, No. 19, pp. 7257-7265 (Oct. 1, 2008).

Moros,J., J. Kuligowski, G. Quintas, S. Garrigues, M. DeLa Guardia, "New cut-off criterion for uninformative variable elimination in multivariate calibration of near-infrared spectra for the determination of heroin in illicit street drugs," Analytica Chimica Acta, vol. 630, pp. 150-160 (2008).

Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.

Na, J, J.H. Baek, S.Y. Ryu, C. Lee, B.H. Lee, "Tomographic imaging of incipient dental-caries using optical coherence tomography and comparison with various modalities," Optical Review, vol. 16, No. 4, pp. 426-431 (2009).

Nachabe, R., D.J. Evers, B.H.W. Hendriks, G.W. Lucassen, M.van der Voort, E.J. Rutgers, M.J.V. Peeters, J.A. Van der Hage, H.S. Oldenburg, J. Wesseling, T.J.M. Ruers, "Diagnosis of breast cancer using diffuse optical spectroscopy from 500 to 1600nm: comparison of classification methods," Journal of Biomedical Optics, vol. 16, No. 8, article 087010, 12 pages (Aug. 2011).

Nang, Yimin, et al., "Ultrahigh-resolution optical coherence tomography by broadband continuum generation from a photonic crystal fiber", Optics Letters, vol. 28, No. 3, Feb. 1, 2003, pp. 182-184.

Nassif, N. A., et al., "In vivo high-resolution video-rate spectral-domain optical coherence tomography of the human retina and optic nerve", Optics Express, vol. 12, No. 3, Feb. 9, 2004, pp. 367-375.

Nellcor; Charts 1-3: Nellcor-533; U.S. Pat. No. 9,651,533 vs. Nellcor; *Omni MedSci, Inc.* v. *Apple Inc.*, pp. 1-155; May 22, 2019.

New and Emerging Techniques—Surgical, Rapid Review, Laser Discectomy, Australian Safety and Efficacy Register of New Interventional Procedures—Surgical, Jun. 2003, 12 pages.

Ng, Choo Lum, Randy L. Wehling, and Susan L Cuppett. "Method for determining frying oil degradation by near-infrared spectroscopy." Journal of agricultural and food chemistry 55.3 (2007): 593-597.

Ni, Yongnian, Minghua Mei, and Serge Kokot. "Analysis of complex, processed substances with the use of NIR spectroscopy and chemometrics: Classification and prediction of properties—The potato crisps example." Chemometrics and Intelligent Laboratory Systems 105.2 (2011): 147-156.

Nicholson, J. W., "Supercontinuum generation in ultraviolet-irradiated fibers", Optics Letters, vol. 29, No. 20, Oct. 15, 2004, pp. 2363-2365.

Nicholson, J. W., et al., "All-fiber, octave-spanning supercontinuum", Optics Letters, vol. 28, No. 8, Apr. 15, 2003, pp. 643-645.

Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.

Nicholson, J. W., et al., "Pulsed and continuous-wave supercontinuum generation in highly nonlinear, dispersion-shifted fibers", Applied Physics B 77, 2003, pp. 211-218.

Nishida, Yoshiki, et al., "Reliability of Fluoride Fiber Module for Optical Amplifier Use", IEEE Photonics Technology Letters, vol. 11, No. 12, Dec. 1999, pp. 1596-1598.

Nishizawa, N., "Generation and application of high-quality supercontinuum sources," Optical Fiber Technology, vol. 18, pp. 394-402 (2012).

Non-Final Office Action for U.S. Appl. No. 14/875,709 dated May 26, 2016.

Noreen, R., C.C. Chien, M. Delugin, S. Yao, R. Pineau, Y. Hwu, M. Moenner, C. Petibois, "Detection of collagens in brain tumors based on FTIR imaging and chemometrics," Annals of Bioanalytic Chemistry, vol. 401, pp. 845-852 (2011).

Notice of Allowance for U.S. Appl. No. 14/875,709 dated Jan. 10, 2017.

(56) References Cited

OTHER PUBLICATIONS

Nowak, G. A., et al., "Low-power high-efficiency wavelength conversion based on modulational instability in high-nonlinearity fiber," Optics Letters, vol. 23, No. 12, Jun. 15, 1998, pp. 936-938.
Nowak, George A., et al., "Stable supercontinuum generation in short lengths of conventional dispersion-shifted fiber", Applied Optics, vol. 38, No. 36, Dec. 20, 1999, pp. 7364-7369.
Nunnally, W.C., S.K. Holland, G. Laufer, "Wide field of view solar occultation gas filter correlation radiometer for stratospheric methane measurements from a sounding rocket," Thermosense XXV, K.E. Elliot, X.P. Maldague, Editors, Proceedings of SPIE, vol. 5073, pp. 122-130 (2003).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Olsen, B.A., M.W. Borer, F.M. Perry, R.A. Forbes, "Screening for counterfeit drugs using near-infrared spectroscopy," Pharmaceutical Technology, pp. 62-71 (Jun. 2002).
Omni MedSci Inc.'s Opening Claim Construction Brief filed in Case No. 2:18-cv-134-RWS (Dkt. #85) (Dec. 20, 2018).
*Omni Medsci, Inc. v. Apple Inc.*; Case No. 2:18-cv-134-RWS (E.D. Tex.); Defendant's Invalidity Contentions, Aug. 28, 2018 (Exhibit A), 66 pps.
*Omni Medsci, Inc. v. Apple Inc.*; Case No. 2:18-cv-134-RWS (E.D. Tex.); Defendants Invalidity Contentions, Aug. 28, 2018 (Exhibit AA), 75 pps.
*Omni Medsci, Inc. v. Apple Inc.*; Case No. 2:18-cv-134-RWS (E.D. Tex.); Defendant's Invalidity Contentions, Aug. 28, 2018 (Exhibit B), 73 pps.
*Omni Medsci, Inc. v. Apple Inc.*; Case No. 2:18-cv-134-RWS (E.D. Tex.); Defendants Invalidity Contentions, Aug. 28, 2018 (Exhibit BB), 65 pps.
*Omni Medsci, Inc. v. Apple Inc.*; Case No. 2:18-cv-134-RWS (E.D. Tex.); Defendant's Invalidity Contentions, Aug. 28, 2018 (Exhibit C), 85 pps.
*Omni Medsci, Inc. V. Apple Inc.*; Case No. 2:18-cv-134-RWS (E.D. Tex.); Defendant's Invalidity Contentions, Aug. 28, 2018 (Exhibit CC), 320 pps.
*Omni Medsci, Inc. V. Apple Inc.*; Case No. 2:18-cv-134-RWS (E.D. Tex.); Defendant's Invalidity Contentions, Aug. 28, 2018 (Exhibit D), 38 pps.
*Omni Medsci, Inc. V. Apple Inc.*; Case No. 2:18-cv-134-RWS (E.D. Tex.); Defendants Invalidity Contentions, Aug. 28, 2018 (Exhibit DD), 240 pps.
*Omni Medsci, Inc. V. Apple Inc.*; Case No. 2:18-cv-134-RWS (E.D. Tex.); Defendants Invalidity Contentions, Aug. 28, 2018 (Exhibit E), 120 pps.
*Omni Medsci, Inc. V. Apple Inc.*; Case No. 2:18-cv-134-RWS (E.D. Tex.); Defendants Invalidity Contentions, Aug. 28, 2018 (Exhibit F), 40 pps.
*Omni Medsci, Inc. V. Apple Inc.*; Case No. 2:18-cv-134-RWS (E.D. Tex.); Defendants Invalidity Contentions, Aug. 28, 2018 (Exhibit G), 66 pps.
*Omni Medsci, Inc. V. Apple Inc.*; Case No. 2:18-cv-134-RWS (E.D. Tex.); Defendants Invalidity Contentions, Aug. 28, 2018 (Exhibit H), 74 pps.
*Omni Medsci, Inc. V. Apple Inc.*; Case No. 2:18-cv-134-RWS (E.D. Tex.); Defendants Invalidity Contentions, Aug. 28, 2018 (Exhibit I), 102 pps.
*Omni Medsci, Inc. V. Apple Inc.*; Case No. 2:18-cv-134-RWS (E.D. Tex.); Defendants Invalidity Contentions, Aug. 28, 2018 (Exhibit J), 64 pps.
*Omni Medsci, Inc. V. Apple Inc.*; Case No. 2:18-cv-134-RWS (E.D. Tex.); Defendants Invalidity Contentions, Aug. 28, 2018 (Exhibit K), 77 pps.
*Omni Medsci, Inc. V. Apple Inc.*; Case No. 2:18-cv-134-RWS (E.D. Tex.); Defendants Invalidity Contentions, Aug. 28, 2018 (Exhibit L), 64 pps.
*Omni Medsci, Inc. V. Apple Inc.*; Case No. 2:18-cv-134-RWS (E.D. Tex.); Defendants Invalidity Contentions, Aug. 28, 2018 (Exhibit M), 119 pps.
*Omni Medsci, Inc. V. Apple Inc.*; Case No. 2:18-cv-134-RWS (E.D. Tex.); Defendants Invalidity Contentions, Aug. 28, 2018 (Exhibit N), 50 pps.
*Omni Medsci, Inc. V. Apple Inc.*; Case No. 2:18-cv-134-RWS (E.D. Tex.); Defendants Invalidity Contentions, Aug. 28, 2018 (Exhibit O), 63 pps.
*Omni Medsci, Inc. V. Apple Inc.*; Case No. 2:18-cv-134-RWS (E.D. Tex.); Defendants Invalidity Contentions, Aug. 28, 2018 (Exhibit P), 78 pps.
*Omni Medsci, Inc. V. Apple Inc.*; Case No. 2:18-cv-134-RWS (E.D. Tex.); Defendants Invalidity Contentions, Aug. 28, 2018 (Exhibit Q), 69 pps.
*Omni Medsci, Inc. V. Apple Inc.*; Case No. 2:18-cv-134-RWS (E.D. Tex.); Defendants Invalidity Contentions, Aug. 28, 2018 (Exhibit R), 61 pps.
*Omni Medsci, Inc. V. Apple Inc.*; Case No. 2:18-cv-134-RWS (E.D. Tex.); Defendants Invalidity Contentions, Aug. 28, 2018 (Exhibit S), 50 pps.
*Omni Medsci, Inc. V. Apple Inc.*; Case No. 2:18-cv-134-RWS (E.D. Tex.); Defendants Invalidity Contentions, Aug. 28, 2018 (Exhibit T), 174 pps.
*Omni Medsci, Inc. V. Apple Inc.*; Case No. 2:18-cv-134-RWS (E.D. Tex.); Defendants Invalidity Contentions, Aug. 28, 2018 (Exhibit U), 334 pps.
*Omni Medsci, Inc. V. Apple Inc.*; Case No. 2:18-cv-134-RWS (E.D. Tex.); Defendants Invalidity Contentions, Aug. 28, 2018 (Exhibit V), 137 pps.
*Omni Medsci, Inc. V. Apple Inc.*; Case No. 2:18-cv-134-RWS (E.D. Tex.); Defendants Invalidity Contentions, Aug. 28, 2018 (Exhibit W), 384 pps.
*Omni Medsci, Inc. V. Apple Inc.*; Case No. 2:18-cv-134-RWS (E.D. Tex.); Defendants Invalidity Contentions, Aug. 28, 2018 (Exhibit X), 291 pps.
*Omni Medsci, Inc. V. Apple Inc.*; Case No. 2:18-cv-134-RWS (E.D. Tex.); Defendants Invalidity Contentions, Aug. 28, 2018 (Exhibit Y), 120 pps.
*Omni Medsci, Inc. V. Apple Inc.*; Case No. 2:18-cv-134-RWS (E.D. Tex.); Defendants Invalidity Contentions, Aug. 28, 2018 (Exhibit Z), 53 pps.
Omre, A., Bluetooth Low Energy: Wireless Connectivity for Medical Monitoring, Journal of Diabetes Science & Technology, vol. 4, Issue 2 (Mar. 2010).
Ooen, Stephane, et al., "Supercontinuum generation by stimulated Raman scattering and Darametric four-wave mixing in photonic crystal fibers", J. Opt. Soc. Am. B, vol. 19, No. 4, Apr. 2002, pp. 753-764.
Ooi ET, Zhang XQ, Chen JH, Soh PH, Ng K, Yeo JH, "Noninvasive glucose measurement using multiple laser diodes," Optical Diagnostic and Sensing VII, edited by Gerard L. Cote, Alexander V. Priezzhev, Proc. of SPIE vol. 6445, 64450K , (2007).
Oughstun, Kurt E., "Influence of precursor fields on ultrashort pulse autocorrelation measurements and pulse width evolution", Optics Express, vol. 8, No. 8, Apr. 9, 2001, pp. 481-491.
P.A. Thielen and L.B. Shaw, et al., "Small-core As—Se fiber for Raman amplification," Optics Leti-ers, vol. 28, No. 16, Aug. 15, 2003, 3 pages.
Palou, A. J. Cruz, M. Blanco, J. Tomas, J. De Los Rios, M. Alcala, "Determination of drug, excipients and coating distribution in pharmaceutical tablets using NIR-CI," Journal of Pharmaceutical Analysis, vol. 2, No. 2, pp. 90-97 (2012).
Pan, Yingtian, et al., "Hand-held arthroscopic optical coherence tomography for in vivo high-resolution imaging of articular cartilage", Journal of Biomedical Optics 8(4), Oct. 2003, pp. 648-654.
Papemyi, S. B., et al., "Sixth-Order Cascaded Raman Amplification", OFC/NFOEC, 2005, 3 pages.
Parawira, S. "Classification of hyperspectral breast images for cancer detection," Dec. 4, 2009, downloaded from WWW, 5 pages.

(56) References Cited

OTHER PUBLICATIONS

Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.

Park; Charts 1-3: Park-533; U.S. Pat. No. 9,651,533 vs. Park; *Omni MedSci, Inc.* v. *Apple Inc.*, pp. 1-171; May 22, 2019.

Passat, "Solid-State Lasers and Optical Components," Jul. 14, 2003, 5 pages.

Patel, S., et al., A review of wearable sensors and systems with application rehabilitation, Journal of Neuroengineering & Rehabilitation 2012 9:21.

Patterson et al., Ratiometric Artifact Reduction in Low Power Reflective Photoplethysmography, (Aug. 2011) IEEE Transactions on Biomedical Circuits and Systems, vol. 5, No. 4, 9 pages.

PCT/US06/44451, Notification of Transmittal of the International Search Report and the Written Opinion of the International Searching Authority, or the Declaration, dated Nov. 29, 2007, 12 pages.

Pedreschi, F., V. H. Segtnan, and S. H. Knutsen. "On-line monitoring of fat, dry matter and acrylamide contents in potato chips using near infrared interactance and visual reflectance imaging." Food Chemistry 121.2 (2010): 616-620.

Peláez, LED Power Reduction Trade-Offs for Ambulatory Pulse Oximetry, Conference Proceedings of the 29th Annual International Conference of the IEEE EMBS (Aug. 2007) Lyon, France, 4 pages.

U.S. Appl. No. 12/206,432, "System and Method for Voice Control of Medical Devices," by Mohammed N. Islam, filed Sep. 8, 2008.

Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).

Pierce, Mark C., et al., "Advances in Optical Coherence Tomography imaging for Dermatology", Optical Coherence Tomography Advances, The Journal of Investigative Dermatology, Sep. 3, 2004, pp. 458-463.

Pojic, M. J. Mastilovic, N. Majcen, "The application of near infrared spectroscopy in wheat quality control," Infrared Spectroscopy—Life and Biomedical Sciences, pp. 167-184 (2012).

Povazay, B., et al., "Submicrometer axial resolution optical coherence tomography", Optical Letters, vol. 27, No. 20, Oct. 15, 2002, pp. 1800-1802.

Proof of Service of Summons in *Omni MedSci, Inc.* v. *Apple Inc.*, No. 2:18-cv-134 (E.D. Tex.) (Dkt. #12) (Apr. 13, 2018).

R.H. Istepanian, B. Woodward, P.A. Bales, S. Chen, B. Luk, "The comparative performance of mobile telemediCal systems based on the IS-54 and GSM cellular telephone standards," Journal of Telemedicine and Telecare, 1999, pp. 97-104.

R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.

Rambla, F.J., S. Garrigues, M. DeLa Guardia, "PLS-NIR determination of total sugar, glucose, fructose and sucrose in aqueous solutions of fruit juices," Analytica Chimica Acta, vol. 344, pp. 41-53 (1997).

Ranka, Jinendra K., et al., "Visible continuum generation in air-silica microstructure optical fibers with anomalous dispersion at 800 nm", Optics Letters, vol. 25, No. 1, Jan. 1, 2000, pp. 25-27.

Rauf Adil, "The Usage of Tablets in the HealthCare Industry," available at https://www.healthcareitnews.com/blog/usage-tablets-healthcare-industry (Aug. 2, 2012).

Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).

Reich, G. "Near-infrared spectroscopy and imaging: basic principles and pharmaceutical applications," Advanced Drug Delivery Reviews, vol. 57, pp. 1109-1143 (2005).

Rein, Alan, and Luis Rodriguez-Saona. "Measurement of Acrylamide in Potato Chips by Portable FTIR Analyzers." (2013).

Rhee et al., Artifact-Resistant Power-Efficient Design of Finger-Ring Plethysmographic Sensors, IEEE Transactions on Biomedical Engineering (Jul. 2001), vol. 48, No. 7, Cambridge, MA, 11 pages.

Robert S. Jones et al.; Near-Infrared Transillumination at 1310-nm for the Imaging of Early Dental Decay; vol. 11; No. 18; Optics Express 2259; Sep. 8, 2003.

Rodionova, O.Y., L.P. Houmoller, A.L. Pomerantsev, P. Geladi, J. Burger, V.L. Dorofeyev, A.P. Arzamastsev, "NIR spectrometry for counterfeit drug detection: a feasibility study," Analytica Chimica Acta, vol. 549, pp. 151-158 (2005).

Roggan, Andre, et al., "Optical Properties of Circulating Human Blood in the Wavelength Range 400-2500 NM", Journal of Biomedical Optics, vol. 4, No. 1, Jan. 1999, pp. 36-46.

Roggo, Y. P. Chalus, L. Maurer, C. Lema-Martinez, A. Edmond, N. Jent, "A review of near infrared spectroscopy and chemometrics in pharmaceutical technologies," Journal of Pharmaceutical and Biomedical Analysis, vol. 44, pp. 683-700 (2007).

Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.

S.D. Khan, S. Jacobson, "Remote sensing and geochemistry for detecting hydrocarbon microseepages," GSA Bulletin, vol. 120, No. 1/2, pp. 96-105 (Jan./Feb. 2008).

Saliminia, A., et al., "Ultra-broad and coherent white light generation in silica glass by focused femtosecond pulses at 1.5pm", Optics Express, vol. 13, No. 15, Jul. 25, 2005, pp. 5731-5738.

Sanghera, J. S., et al., Active and passive chalcogenide glass optical fibers for IR applications: a review, Journal of Non-Crystalline Solids 256 & 257, 1999, pp. 6-16.

Scafi, S.H.F., C. Pasquini, "Identification of counterfeit drugs using near-infrared spectroscopy," Analyst, vol. 126, pp. 2218-2224 (2001).

Schmitt, Joseph, et al., "Intravascular Optical Coherence Tomography Opens a Window Onto Coronary Artery Disease", Optics & Photonics News, Feb. 2004, pp. 20-25.

Schneider, R.C., K.A. Kovar, "Analysis of ecstasy tablets: comparison of reflectance and transmittance near infrared spectroscopy," Forensic Science International, vol. 134, pp. 187-195 (2003).

Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.

Schreiner et al., Blood Oxygen Level Measurement with a Chest-Based Pulse Oximetry Prototype System, Computing in Cardiology (2010) NIBEC, University of Ulster, Newtownabbey, Northern Ireland, 4 pages.

Schubert, E.F., Light-Emitting Diodes (Cambridge Univ. Press, 2nd ed. Reprinted 2014).

Schulz, I., J. Putzger, A. Niklas, M. Brandt, A. Jager, A. Hardt, S. Knorzer, K.A. Hiller, S. Loffler, G. Schmalz, S.N. Danilov, S. Giglberger, M. Hirmer, S.D. Ganichev, G. Monkman, "PPG signal acquisition and analysis on in vitro tooth model for dental pulp vitality assessment," ARC Submission 16, (2012).

Seefeldt, Michael, et al., "Compact white-light source with an average output power of 2.4 Wand 900 nm spectral bandwidth", Optics Communications 216, pp. 199-202.

Segtnan, Vegard H., et al. "Screening of acrylamide contents in potato crisps using process variable settings and near-infrared spectroscopy." Molecular nutrition & food research 50.9 (2006): 811-817.

September, Danwille Jacqwin Franco. Detection and quantification of spice adulteration by near infrared hyperspectral imaging. Diss. Stellenbosch: University of Stellenbosch, 2011.

Shaw, et al, IR Supercontinuum Generation in As—Se Photonic Crystal Fiber, Optical Society of America, Copyright 2005, 3 pages.

Shiroma, Cecilia, and Luis Rodriguez-Saona. "Application of NIR and MIR spectroscopy in quality control of potato chips." Journal of Food Composition and Analysis 22.6 (2009): 596-605.

Shiroma, Cecilia. "Rapid quality control of potato chips using near and mid-infrared spectroscopy." (2007).

Shu-Fang, T. C. Jian-Ping, Z. Mi, "The information of oil and gas micro-seepage in Dongsheng Region of Inner Mongolia extraction based on the airborne hyperspectral remote sensing image," Remote

(56) References Cited

OTHER PUBLICATIONS

Sensing of the Environment, 16th National Symposium on Remote Sensing of China, edited by Q. Tong, Proceedings of SPIE, vol. 7123, 71230K-1 to 8, (2008).
Slusher, Richard, et al., "Highly nonlinear composite chalcogenide/polymer fibers", OSA 2004, 1 page.
Slusher, Richart E., et al., "Large Raman gain and nonlinear phase shills in high-purity As2So3 chalcogenide fibers", J. Opt. Soc. Am. B, vol. 21, No. 6, Jun. 2004, pp. 1146-1155.
Smektala, F., et al., "Chalcogenide glasses with large non-linear refractive indices", Journal of Non-Crystalline Solids 239, 1998, pp. 139-142.
Smith, J.L., "The Pursuit of Noninvasive Glucose: Hunting the Deceitful Turkey," 2nd Edition, pp. 1-141 (2011).
Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.
Sondermann, N., K.A. Kovar, "Identification of ecstasy in complex matrices using near-infrared spectroscopy," Forensic Science International, vol. 102, pp. 133-147 (1999).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
State-Specific Trends in Chronic Kidney Failure-United States, 1990-2001, Morbidity and Mortality Weekly Report, Department of Health and Human Services Centers for Disease Control and Prevention, vol. 53, No. 39, copied from internet: file://C:\Documents and Settings\eturlo\Desktop\State-Specific Trends in Chronic Kidney . . . Feb. 12, 2010, Oct. 8, 2004, pp. 918-920.
Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).
Swan, M., Sensor Mania! The Internet of Things, Wearable Computing, Objective Metrics, and the Quantified Self 2.0, Journal of Sensor and Actuator Networks (2012).
Takushima, Yuichi, High average power, depolarized supercontinuum generation using a 1.55-um ASE noise source, Optics Express, vol. 13, No. 15, Jul. 25, 2005, pp. 5871-5877.
Tanaka, Keiji, "Optical nonlinearity in photonic glasses", Journal of Materials Science: Materials in Electronics 16, 2005, pp. 633-643.
Taos, Inc., Infrared Light-to-Voltage Optical Sensors, (2006) Texas Advanced Optoelectronic Solutions Inc., The Lumenology Company, TX, 14 pages.
Taroni, P. D. Cornelli, A. Giusto, A. Pifferi, N. Shah, L. Spinelli, A. Torricelli, R. Cubeddu, "Assessment of collagen absorption and related potential diagnostic applications," Diffuse Optical Imaging of Tissue, edited by B.W. Pogue, R. Cubeddu, Proceedings of SPIE-OSA Biomedical Optics, SPIE vol. 6629, paper 66290D, 5 pages, (2007).
Taroni, P., "Diffuse optical imaging and spectroscopy of the breast: a brief outline of history and perspectives," Photochemical Photobiological Science, vol. 11, pp. 241-250 (2012).
Tearney, Guillermo J., et al., "In vivo Endoscopic Optical Biopsy with Optical Coherence Tomography", Science, New Series, vol. 276, Jun. 27, 1997, pp. 2037-2039.
Technology Transfer Policy, Office of Technology Transfer—University of Michigan (available at https://techtransfer.umich.edu/for-inventors/policies/technology-transfer--policy/) (revision effective Jun. 1, 2009).
The Bylaws of the University of Michigan Board of Regents, (available at http://www.regents.umich.edu/bylaws/bylawsrevised_09-18.pdf) (last updated Sep. 20, 2018).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Thongtrangan, Issada, et al., "Minimally invasive spinal surgery: a historical perspective", Neurosurg. Focus, vol. 16, Article 13, Jan. 2004, pp. 1-10.
Thybo, Anette Kistrup, et al. "Prediction of sensory texture of cooked potatoes using uniaxial compression, near infrared spectroscopy and low field1H NMR spectroscopy." LWT—Food Science and Technology 33.2 (2000): 103-111.
Tolton, B.T., "A concept for a gas-filter correlation radiometer to remotely sense the atmospheric carbon dioxide column from space," Notes and Correspondence, Journal of Atmospheric and Oceanic Technology, vol. 21, pp. 837-852, (May 2004).
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.
Travers, J. C., et al., "Extended blue supercontinuum generation in cascaded holey fibers", Optics Letters, vol. 30, No. 23, Dec. 1, 2005, pp. 3132-3134.
Travers, J. C., et al., "Extended continuous-wave supercontinuum generation in a low-water-loss holey fiber", Optics Letters, vol. 30, No. 15, Aug. 1, 2005, pp. 1938-1940.
Troy, T.L., S.N. Thennadil, "Optical properties of human skin in the near infrared wavelength range of 1000 to 2200nm," Journal of Biomedical Optics, vol. 6, No. 2, pp. 167-176, (2001).
U.S. Appl. No. 10/652,276, "System and Method for Voice Control of Medical devices," by Mohammed N. Islam, abandoned filed Aug. 29, 2003.
U.S. Appl. No. 10/757,341, "System and Method for Voice Control of Medical devices," by Mohammed N. Islam, filed Jan. 13, 2004.
U.S. Appl. No. 12/206,432, "System and Method for Voice Control of Medical Devices," by Mohammed N. Islam, pending filed Sep. 8, 2008.
U.S. Appl. No. 61/350,673; titled: Opticoustic Sensor; Inventor: Massi Joe E. Kiani; filed Jun. 2, 2010.
U.S. Appl. No. 61/747,472, filed Dec. 31, 2012.
U.S. Appl. No. 61/747,477, filed Dec. 31, 2012.
U.S. Appl. No. 61/747,487, filed Dec. 31, 2012.
U.S. Appl. No. 61/754,698, filed Jan. 21, 2013.
U.S. Patent and Trademark Office, Notice of Allowance and Fee(s) Due for U.S. Appl. No. 12/206,432, filed Sep. 8, 2008, Mohammed N. Islam, Date filed: Aug. 28, 2009.
U.S. Patent and Trademark Office, Office Action for U.S. Appl. No. 12/206,432, filed Sep. 8, 2008, Mohammed N, Islam, Date Filed: Mar. 12, 2009.
United States District Court Eastern District of Texas Marshall Division; Defendant and Counter Claimant Apple Inc.'s Amended Answer, Affirmative Defenses, and Counterclaims to Complaint of Plaintiff and Counter Defendant Omni Medsci, Inc.; Document 38; Jul. 19, 2018; 32 pps.
United States District Court Eastern District of Texas Marshall Division; *Omni Medsci, Inc.* vs. *Apple Inc.*; Civil Action No. 2:18-cv-00134 Jury Trial Demanded; Defendant's Invalidity Contentions; Aug. 28, 2018; 33 pps.
Unterhuber, A., et al., "Advances in broad bandwidth light sources for ultrahigh resolution optical coherence tomography", Physics in Medicine and Biology, Phys. Med. Biol. 49, 2004, pp. 1235-1246.
Urban, J. P. G., et al., "The Nucleus of the Intervertebral Disc from Development to Degeneration" Amer. Zool., vol. 40, 2000, pp. 53-61.
Urbas, A., M.W. Manning, A. Daugherty, L.A. Cassis, R.A. Lodder, "Near-infrared spectrometry of abdominal aortic aneurysm in the ApoE Mouse," Analytical Chemistry, vol. 75, No. 15, pp. 3650-3655 (Jul. 15, 2003).
Valencell; Charts 1-3: Valencell-533; U.S. Pat. No. 9,651,533 vs. Valencell; *Omni MedSci, Inc.* v. *Apple Inc.*, pp. 1-122; May 22, 2019.
Van Der Meer, F. P. Van Dijk, H. Van Der Werff, H. Yang, "Remote sensing and petroleum seepage: a review and case study," Terra Nova, vol. 14, No. 1, pp. 1-17 (2002).
Van Der Meer, F., P. Van Dijk, S. Kroonenberg, Y. Hong, H. Lang, "Hyperspectral hydrocarbon microseepage detection and monitor-

(56) References Cited

OTHER PUBLICATIONS ing: potentials and limitations," Second EARSEI workshop on imaging spectroscopy, pp. 1-9 (2000).

Venugopalan, V., "Optical Society of America BIOMED Topical Meeting Tutorial on Tissue Optics", Apr. 27, 2004, pp. 1-32.

Vinay V. Alexander et al; Modulation Instability High Power All-Fiber Supercontinuum Lasers and Their Applications; Optical Fiber Technology 18; 2012; pp. 349-374.

Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.

Wadsworth, William J., et al., "Supercontinuum generation in photonic crystal fibers and Optical fiber tapers: a novel light source", J. Opt. Soc. Am. B, vol. 19, No. 9, Sep. 2002, pp. 2148-2155.

Walsh, M.J., R.K. Reddy, R. Bhargava, "Label-free biomedical imaging with mid-IR spectroscopy," IEEE Journal of Selected Topics in Quantum Electronics, article identifier 10.1109/JSTQE.2011.2182635, 12 pages, (2011).

Wang et al., Multichannel Reflective PPG Earpiece Sensor with Passive Motion Cancellation, (Dec. 2007) IEEE Transactions on Biomedical Circuits and Systems, vol. 1, No. 4, 7 pages.

Wang, Lihong V., Multiscale photoacoustic microscopy and computed tomography, Sep. 2009, Nature Photonics, vol. 3, pp. 503-509.

Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.

Watari, M., H. Migashiyama, N. Mitsui, M. Tomo, Y. Ozaki, "On-line monitoring of the density of linear low-density polyethylene in a real plant by near-infrared spectroscopy and chemometrics," Applied Spectroscopy, vol. 58, No. 2, pp. 248-255 (2004).

Webster, Design of Pulse Oximeters, Medical Science Series (1997), Department of Electrical and Computer Engineering, University of Wisconsin-Madison, Institute of Physics Publishing, Bristol and Philadelphia, 267 pages.

Wedding, B.B., C. Wright, S. Grauf, R.D. White, "The application of near infrared spectroscopy for the assessment of avocado quality attributes," Infrared Spectroscopy—Life and Biomedical Sciences, pp. 211-230 (2011).

Werle, Peter, et al., "Near- and mid-infrared laser-optical sensors for gas analysis", Optics and Lasers in Engineering 37, 2002, pp. 101-114.

Westbrook, Paul S., "Improved Supercontinuum Generation Through UV Processing of Highly Nonlinear Fibers", Journal of Lightwave Technology, vol. 23, No. 1, Jan. 2005, pp. 13-18.

Williams, Phil. "Near-Infrared Spectroscopy of Cereals." Handbook of vibrational spectroscopy (2006).

Wuthrich, Stefan, et al., "Optical damage thresholds at 2.94 um in fluoride glass fibers", Applied Optics, vol. 31, No. 27, Sep. 20, 1992, pp. 5833-5837.

Xiao, J. Q. Tian, Y. Lu, L. Wang, X. Qi, B. Wen, "Extraction of hydrocarbon content information by using hyperspectral image at Liaodong Bay, China," downloaded from world wide web on Apr. 6, 2012.

Xie, T.-Q., et al., "Detection of tumorigenesis in urinary bladder with optical coherence tomography: optical characterization of morphological changes", Optics Express, vol. 10, No. 24, Dec. 2, 2002, 2003, pp. 1431-1443.

Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.

Xu, D., G. Ni, T. Jiang, L. Jiang, M. Chi, "Integration of field work and hyperspectral data for oil and gas exploration," IEEE 1-4244-1212-9/07, pp. 3194-3197 (2007).

Xu, D-Q, G-Q Ni, L-L Jiang, Y-T Shen, T. Li, S-L Ge, X-B Shu, "Exploring for natural gas using reflectance spectra of surface soils," Advances in Space Research, vol. 41, pp. 1800-1817 (2008).

Yamaha, BODiBEAT, Body, Music, in Sync., BF-1 Quick Guide, Player/Heart Rate Monitor: Quick Manual, 120 pages.

Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).

Zakian, C. I. Pretty, R. Ellwood, "Near-infrared hyperspectral imaging of teeth for dental canes detection," Journal of Biomedical Optics, vol. 16, No. 6, 064047 (2009).

Ziegler, U., A.G. Bittermann, M. Hoechli, "Introduction to Confocal Laser Scanning Microscopy (LEICA)," www.zmb.unizh.ch, May 29, 2013.

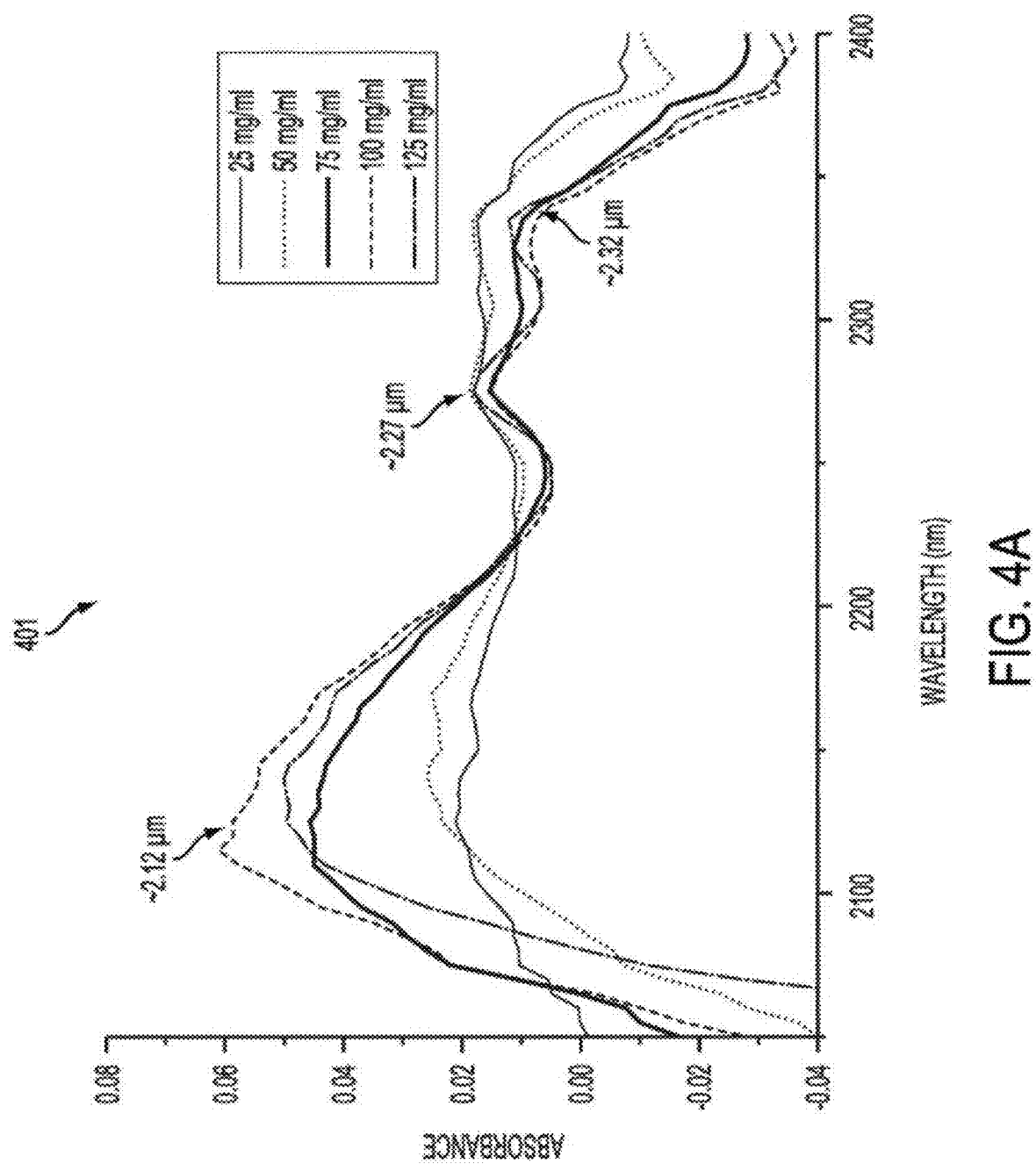

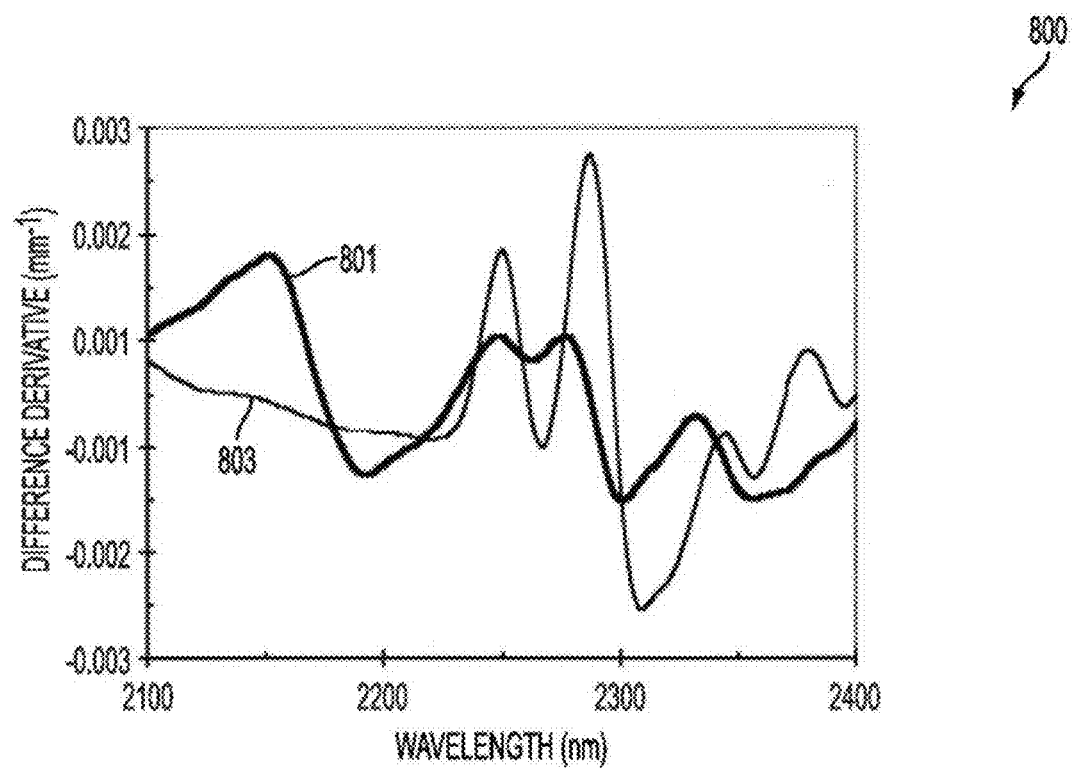
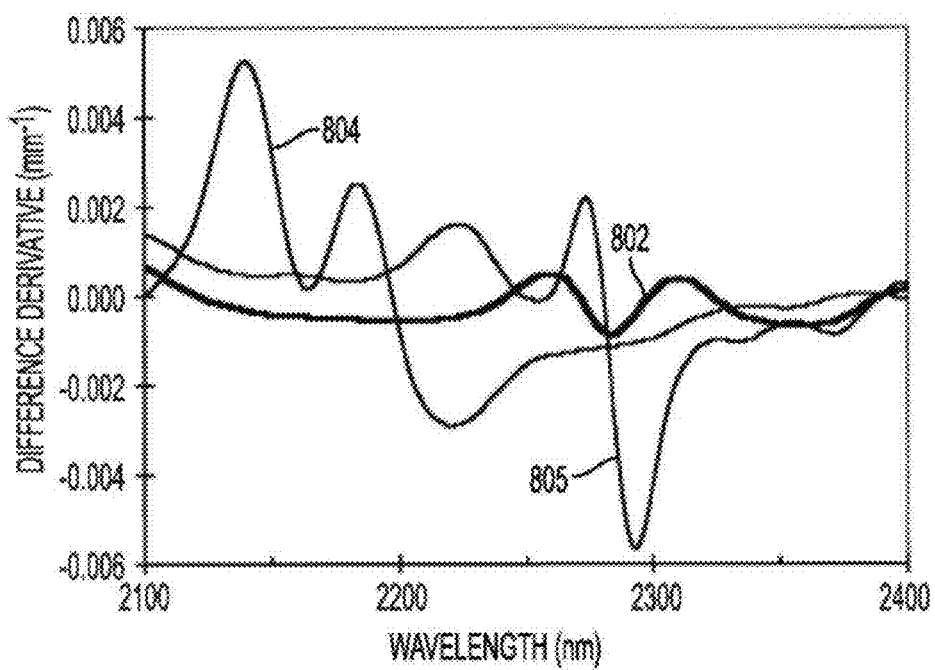
FIG. 8A

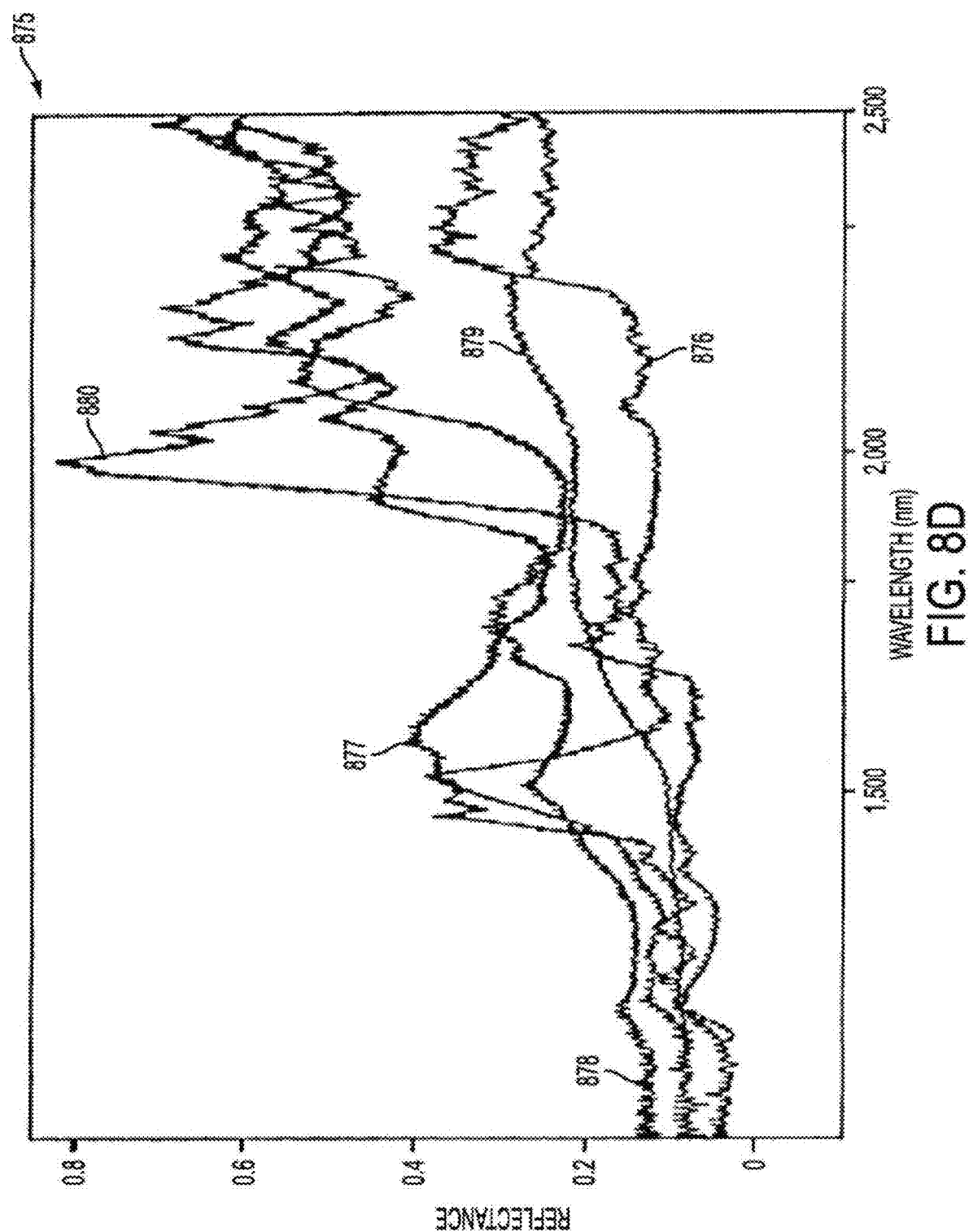

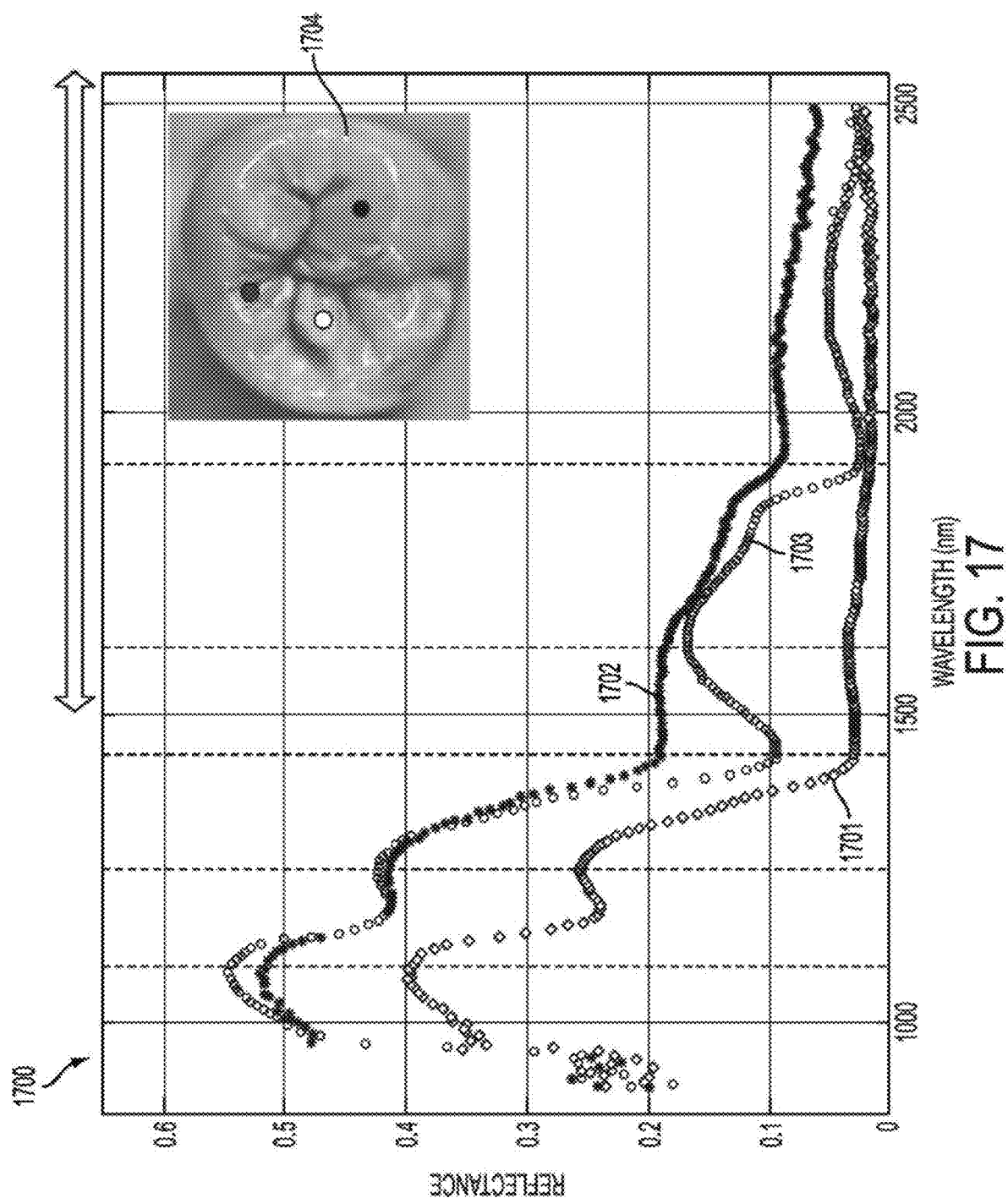

TIME-OF-FLIGHT MEASUREMENT OF SKIN OR BLOOD USING ARRAY OF LASER DIODES WITH BRAGG REFLECTORS

CROSS-REFERENCE TO RELATED APPLICATIONS

This application is a continuation of U.S. application Ser. No. 16/506,885 filed Jul. 9, 2019, now U.S. Pat. No. 10,517,484, which is a continuation of U.S. application Ser. No. 16/272,069 filed Feb. 11, 2019, which is a continuation of U.S. application Ser. No. 16/029,611 filed Jul. 8, 2018, now U.S. Pat. No. 10,201,283, which is a continuation of U.S. application Ser. No. 15/888,052 filed Feb. 4, 2018, now U.S. Pat. No. 10,136,819, which is a continuation of U.S. application Ser. No. 15/212,549 filed Jul. 18, 2016, now U.S. Pat. No. 9,885,698, which is a continuation of U.S. application Ser. No. 14/650,897 filed Jun. 10, 2015, now U.S. Pat. No. 9,494,567, which is a U.S. National Phase of PCT/US2013/075700 filed Dec. 17, 2013, which claims the benefit of U.S. provisional application Ser. No. 61/747,472 filed Dec. 31, 2012, the disclosures of all of which are hereby incorporated in their entirety by reference herein.

U.S. application Ser. No. 16/506,885 is also a continuation of U.S. application Ser. No. 16/004,359 filed Jun. 9, 2018, which is a continuation of U.S. application Ser. No. 14/109,007 filed Dec. 17, 2013 (now U.S. Pat. No. 9,993,159), which claims the benefit of U.S. provisional application Ser. No. 61/747,553 filed Dec. 31, 2012, the disclosures of all of which are hereby incorporated in their entirety by reference herein.

U.S. application Ser. No. 16/506,885 is also a continuation of U.S. application Ser. No. 16/188,194 filed Nov. 12, 2018, now U.S. Pat. No. 10,386,230, which is a continuation of U.S. application Ser. No. 16/004,154 filed Jun. 8, 2018 (now U.S. Pat. No. 10,126,283), which is a continuation of U.S. application Ser. No. 15/855,201 filed Dec. 27, 2017 (now U.S. Pat. No. 9,995,722), which is a continuation of U.S. application Ser. No. 15/711,907 filed Sep. 21, 2017 (now U.S. Pat. No. 9,897,584), which is a divisional of U.S. application Ser. No. 15/357,225 filed Nov. 21, 2016 (now U.S. Pat. No. 9,797,876), which is a continuation of U.S. application Ser. No. 14/650,981 filed Jun. 10, 2015 (now U.S. Pat. No. 9,500,634), which is the U.S. national phase of PCT Application No. PCT/US2013/075767 filed Dec. 17, 2013, which claims the benefit of U.S. provisional application Ser. No. 61/747,485 filed Dec. 31, 2012, the disclosures of all of which are hereby incorporated by reference in their entirety.

U.S. application Ser. No. 16/506,885 is also a continuation of U.S. application Ser. No. 16/241,628 filed Jan. 7, 2019, now U.S. Pat. No. 10,441,176, which is a continuation of U.S. Ser. No. 16/015,737 filed Jun. 22, 2018 (now U.S. Pat. No. 10,172,523), which is a continuation of U.S. Ser. No. 15/594,053 filed May 12, 2017 (now U.S. Pat. No. 10,188,299), which is a continuation of U.S. application Ser. No. 14/875,709 filed Oct. 6, 2015 (now U.S. Pat. No. 9,651,533), which is a continuation of U.S. application Ser. No. 14/108,986 filed Dec. 17, 2013 (now U.S. Pat. No. 9,164,032), which claims the benefit of U.S. provisional application Ser. No. 61/747,487 filed Dec. 31, 2012, the disclosures of all of which are hereby incorporated in their entirety by reference herein.

U.S. application Ser. No. 16/506,885 is also a continuation of U.S. application Ser. No. 16/284,514 filed Feb. 25, 2019, which is a continuation of U.S. application Ser. No. 16/016,649 filed Jun. 24, 2018 (now U.S. Pat. No. 10,213,113), which is a continuation of U.S. application Ser. No. 15/860,065 filed Jan. 2, 2018 (now U.S. Pat. No. 10,098,546), which is a Continuation of U.S. application Ser. No. 15/686,198 filed Aug. 25, 2017 (now U.S. Pat. No. 9,861,286), which is a continuation of U.S. application Ser. No. 15/357,136 filed Nov. 21, 2016 (now U.S. Pat. No. 9,757,040), which is a continuation of U.S. application Ser. No. 14/651,367 filed Jun. 11, 2015 (now U.S. Pat. No. 9,500,635), which is the U.S. national phase of PCT Application No. PCT/US2013/075736 filed Dec. 17, 2013, which claims the benefit of U.S. provisional application Ser. No. 61/747,477 filed Dec. 31, 2012 and U.S. provisional application Ser. No. 61/754,698 filed Jan. 21, 2013, the disclosures of all of which are hereby incorporated by reference in their entirety.

This application is related to U.S. provisional application Ser. No. 61/747,477 filed Dec. 31, 2012; Ser. No. 61/747,481 filed Dec. 31, 2012; Ser. No. 61/747,485 filed Dec. 31, 2012; Ser. No. 61/747,487 filed Dec. 31, 2012; Ser. No. 61/747,492 filed Dec. 31, 2012; Ser. No. 61/747,553 filed Dec. 31, 2012; and Ser. No. 61/754,698 filed Jan. 21, 2013, the disclosures of all of which are hereby incorporated in their entirety by reference herein.

This application is also related to International Application PCT/US2013/075736 entitled Short-Wave Infrared Super-Continuum Lasers For Early Detection Of Dental Caries; U.S. application Ser. No. 14/108,995 filed Dec. 17, 2013 entitled Focused Near-Infrared Lasers For Non-Invasive Vasectomy And Other Thermal Coagulation Or Occlusion Procedures (U.S. Pat. App. Pub. No. US2014/0188092A1); International Application PCT/US2013/075767 entitled Short-Wave Infrared Super-Continuum Lasers For Natural Gas Leak Detection, Exploration, And Other Active Remote Sensing Applications; U.S. application Ser. No. 14/108,986 filed Dec. 17, 2013 entitled Short-Wave Infrared Super-Continuum Lasers For Detecting Counterfeit Or Illicit Drugs And Pharmaceutical Process Control (now U.S. Pat. No. 9,164,032); U.S. application Ser. No. 14/108,974 filed Dec. 17, 2013 entitled Non-Invasive Treatment Of Varicose Veins (U.S. Pat. App. Pub. No. US2014/018894A1); and U.S. application Ser. No. 14/109,007 filed Dec. 17, 2013 entitled Near-Infrared Super-Continuum Lasers For Early Detection Of Breast And Other Cancers (now U.S. Pat. No. 9,993,159), the disclosures of all of which are hereby incorporated in their entirety by reference herein.

BACKGROUND

With the growing obesity epidemic, the number of individuals with diabetes is also increasing dramatically. For example, there are over 200 million people who have diabetes. Diabetes control requires monitoring of the glucose level, and most glucose measuring systems available commercially require drawing of blood. Depending on the severity of the diabetes, a patient may have to draw blood and measure glucose four to six times a day. This may be extremely painful and inconvenient for many people. In addition, for some groups, such as soldiers in the battlefield, it may be dangerous to have to measure periodically their glucose level with finger pricks.

Thus, there is an unmet need for non-invasive glucose monitoring (e.g., monitoring glucose without drawing blood). The challenge has been that a non-invasive system requires adequate sensitivity and selectivity, along with repeatability of the results. Yet, this is a very large market, with an estimated annual market of over $10B in 2011 for self-monitoring of glucose levels.

One approach to non-invasive monitoring of blood constituents or blood analytes is to use near-infrared spectroscopy, such as absorption spectroscopy or near-infrared diffuse reflection or transmission spectroscopy. Some attempts have been made to use broadband light sources, such as tungsten lamps, to perform the spectroscopy. However, several challenges have arisen in these efforts. First, many other constituents in the blood also have signatures in the near-infrared, so spectroscopy and pattern matching, often called spectral fingerprinting, is required to distinguish the glucose with sufficient confidence. Second, the non-invasive procedures have often transmitted or reflected light through the skin, but skin has many spectral artifacts in the near-infrared that may mask the glucose signatures. Moreover, the skin may have significant water and blood content. These difficulties become particularly complicated when a weak light source is used, such as a lamp. More light intensity can help to increase the signal levels, and, hence, the signal-to-noise ratio.

As described in this disclosure, by using brighter light sources, such as fiber-based supercontinuum lasers, superluminescent laser diodes, light-emitting diodes or a number of laser diodes, the near-infrared signal level from blood constituents may be increased. By shining light through the teeth, which have fewer spectral artifacts than skin in the near-infrared, the blood constituents may be measured with less interfering artifacts. Also, by using pattern matching in spectral fingerprinting and various software techniques, the signatures from different constituents in the blood may be identified. Moreover, value-add services may be provided by wirelessly communicating the monitored data to a handheld device such as a smart phone, and then wirelessly communicating the processed data to the cloud for storing, processing, and transmitting to several locations.

SUMMARY OF EXAMPLE EMBODIMENTS

In one embodiment, a smart phone or tablet comprises one or more laser diodes configured to be pulsed and to generate light having one or more optical wavelengths, wherein at least a portion of the one or more optical wavelengths is a near-infrared wavelength between 700 nanometers and 2500 nanometers. A first one or more lenses is configured to receive a portion of the light from the one or more laser diodes and to direct at least some portion of the received light to tissue. An array of laser diodes is configured to be pulsed and to generate light having one or more optical wavelengths, wherein at least a portion of the one or more optical wavelengths is a near-infrared wavelength between 700 nanometers and 2500 nanometers. A second one or more lenses is configured to receive a portion of the light from the array of laser diodes, the array of laser diodes and the second one or more lenses configured to form the light into a plurality of spots and to direct at least some of the spots to tissue. An infrared camera is configured to be synchronized to the at least one of the one or more laser diodes to receive at least a portion of light reflected from the tissue from at least one of the one or more laser diodes, wherein the infrared camera generates data based at least in part on the received light. The infrared camera is further configured to be synchronized to the array of laser diodes to receive light from at least a portion of the plurality of spots reflected from the tissue, and wherein the infrared camera generates additional data based at least in part on the received light. The infrared camera is further configured to: receive light while the one or more laser diodes and the array of laser diodes are off and convert the received light into a first signal; and receive light while at least some of the one or more laser diodes or some of the array of laser diodes are on, and convert the received light into a second signal, the received light including at least a part of the portion of the light from the at least one of the one or more laser diodes reflected from the tissue, or at least a part of the portion of the light from the array of laser diodes reflected from the tissue. The smart phone or tablet is configured to generate a two-dimensional or three-dimensional image using a difference between the first signal and the second signal, and using at least part of the data or at least part of the additional data from the infrared camera. The smart phone or tablet further comprises a wireless receiver, a wireless transmitter, a display, a voice input module, and a speaker.

Embodiments may include a smart phone or tablet comprising one or more laser diodes configured to be pulsed and to generate light having one or more optical wavelengths, wherein at least a portion of the one or more optical wavelengths is a near-infrared wavelength between 700 nanometers and 2500 nanometers. A first one or more lenses is configured to receive a portion of the light from the one or more laser diodes and to direct at least some portion of the received light to tissue. An array of laser diodes is configured to be pulsed and to generate light having one or more optical wavelengths, wherein at least a portion of the one or more optical wavelengths is a near-infrared wavelength between 700 nanometers and 2500 nanometers. A second one or more lenses is configured to receive a portion of the light from the array of laser diodes, the array of laser diodes and the second one or more lenses configured to form the light into a plurality of spots and to direct at least some of the spots to tissue. An infrared camera is configured to be synchronized to the at least one of the one or more laser diodes to receive at least a portion of light reflected from the tissue from at least one of the one or more laser diodes, and wherein the infrared camera generates data based at least in part on the received light. The infrared camera is further configured to be synchronized to the array of laser diodes to receive light from at least a portion of the plurality of spots reflected from the tissue, wherein the infrared camera generates additional data based at least in part on the received light. The smart phone or tablet is configured to generate a two-dimensional or three-dimensional image using at least part of the data or part of the additional data from the infrared camera. The smart phone or tablet further comprises a wireless receiver, a wireless transmitter, a display, a voice input module, and a speaker.

In one embodiment, a smart phone or tablet comprises one or more laser diodes configured to be pulsed and to generate light having one or more optical wavelengths, wherein at least a portion of the one or more optical wavelengths is a near-infrared wavelength between 700 nanometers and 2500 nanometers. A first one or more lenses is configured to receive a portion of the light from the one or more laser diodes and to direct at least some portion of the received light to tissue. An array of laser diodes is configured to be pulsed and to generate light having one or more optical wavelengths, wherein at least a portion of the one or more optical wavelengths is a near-infrared wavelength between 700 nanometers and 2500 nanometers. A second one or more lenses is configured to receive a portion of the light from the array of laser diodes, the array of laser diodes and the second one or more lenses configured to form the light into a plurality of spots and to direct at least some of the spots to tissue, wherein the plurality of spots are also formed at least in part by using an assembly in front of the array of laser diodes. An infrared camera is configured to be synchronized to the at least one of the one or more laser diodes to receive at least a portion of light reflected from the tissue from at least one of the one or more laser diodes, wherein the infrared camera generates data based at least in part on the received light. The infrared camera is further configured to be synchronized to the array of laser diodes to receive light from at least a portion of the plurality of spots reflected from the tissue, wherein the infrared camera generates additional data based at least in part on the received light. The smart phone or tablet is configured to generate a two-dimensional or three-dimensional image using at least part of the data or part of the additional data from the infrared camera. The smart phone or tablet further comprises a wireless receiver, a wireless transmitter, a display, a voice input module, and a speaker.

In one embodiment, an optical tomography system comprises an array of laser diodes to generate light having one or more optical wavelengths that includes at least one near-infrared wavelength between 600 nanometers and 1000 nanometers, at least one laser diode of the array comprises one or more Bragg reflectors. At least one of the laser diodes to pulse at a modulation frequency between 10 Megahertz and 1 Gigahertz and to have a phase associated with the modulation frequency, wherein at least a portion of the light generated by the array is configured to penetrate tissue comprising skin. A detection system comprises at least one photo-detector, a lens at an input to the at least one photo-detector, and a processor to process digitized signals received from the at least one photo-detector, the detection system configured to (i) measure a phase shift of at least a portion of the light from the array of laser diodes reflected from the tissue relative to the portion of the light generated by the array to penetrate the tissue, (ii) measure time-of-flight of at least a portion of the light from the array of laser diodes reflected from the tissue relative to the portion of the light generated by the array to penetrate the tissue, (iii) generate one or more images of the tissue based at least in part on an amplitude of at least a portion of the light from the array of laser diodes reflected from the tissue, and (iv) detect oxy- or deoxy-hemoglobin in the tissue.

In another embodiment, a blood measurement system comprises an array of laser diodes to generate light having one or more optical wavelengths that includes at least one near-infrared wavelength, the array of laser diodes comprising one or more Bragg reflectors, wherein at least a portion of the light generated by the array is configured to penetrate tissue comprising skin. At least one of the laser diodes to pulse at a pulse repetition rate between one (1) kilohertz and about 100 megahertz. A detection system to non-invasively measure blood in veins based at least in part on near-infrared diffuse reflection from the skin, the detection system comprising at least one photo-detector and a lens system coupled to the at least one photo-detector, wherein the at least one photo-detector is coupled to one or more analog-to-digital converters and a processor. The detection system is configured to measure absorption of hemoglobin in the near-infrared wavelength between 700 nanometers and 1300 nanometers. The detection system processor is configured to: differentiate between a region in the skin having a vein and a region in the skin without distinct veins, and implement pattern matching and a threshold function to correlate detected blood concentrations with a library of known concentrations to determine overlap between the detected blood concentrations and known concentrations in the library.

In yet another embodiment an optical identification system comprises an array of laser diodes to generate light having one or more optical wavelengths that includes at least one near-infrared wavelength between 600 nanometers and 1000 nanometers, at least one laser diode of the array comprises one or more Bragg reflectors, wherein at least a portion of the light generated by the array of laser diodes is configured to be directed to tissue comprising skin. At least one of the laser diodes to pulse at a modulation frequency between 10 Megahertz and 1 Gigahertz and to have a phase associated with the modulation frequency. A detection system comprises at least one photo-detector, a lens at an input to the at least one photo-detector, and a processor to process digitized signals received from the at least one photo-detector, the detection system configured to (i) measure a phase shift of at least a portion of the light from the array of laser diodes reflected from the tissue, (ii) measure time-of-flight of at least a portion of the light from the array of laser diodes reflected from the tissue, (iii) generate one or more images of the tissue based at least in part on an amplitude of at least a portion of the light from the array of laser diodes reflected from the tissue, and (iv) generate a depth image from a temporal distribution of light relative to a reference signal.

BRIEF DESCRIPTION OF THE DRAWINGS

For a more complete understanding of the present disclosure, and for further features and advantages thereof, reference is now made to the following description taken in conjunction with the accompanying drawings, in which:

FIG. 4A shows measured absorbance in different concentrations of glucose solution over the wavelength range of about 2000 to 2400 nm. This data is collected using a SWIR super-continuum laser with the sample path length of about 1.1 mm.

FIG. 8A shows the first derivative spectra of ketone and protein at concentrations of 10 g/L (left). In addition, the first derivative spectra of urea, creatinine, and glucose are shown on the right at concentrations of 10 g/L.

FIG. 8D illustrates the near-infrared reflectance versus wavelength for various blood constituents, including cholesterol, glucose, albumin, uric acid, and urea.

FIG. 17 shows the near infrared spectral reflectance over the wavelength range of approximately 800 nm to 2500 nm from an occlusal tooth surface. The black diamonds correspond to the reflectance from a sound, intact tooth section. The asterisks correspond to a tooth section with an enamel lesion. The circles correspond to a tooth section with a dentine lesion.

FIG. 33A illustrates logarithm of the inverse of reflection spectra; and FIG. 33B illustrates second derivative spectra.

FIG. 42A illustrates renal arteries with no laser exposure. FIG. 42B illustrates renal arteries after focused laser exposure, with the laser light near 1708 nm.

DETAILED DESCRIPTION

Figure 1:
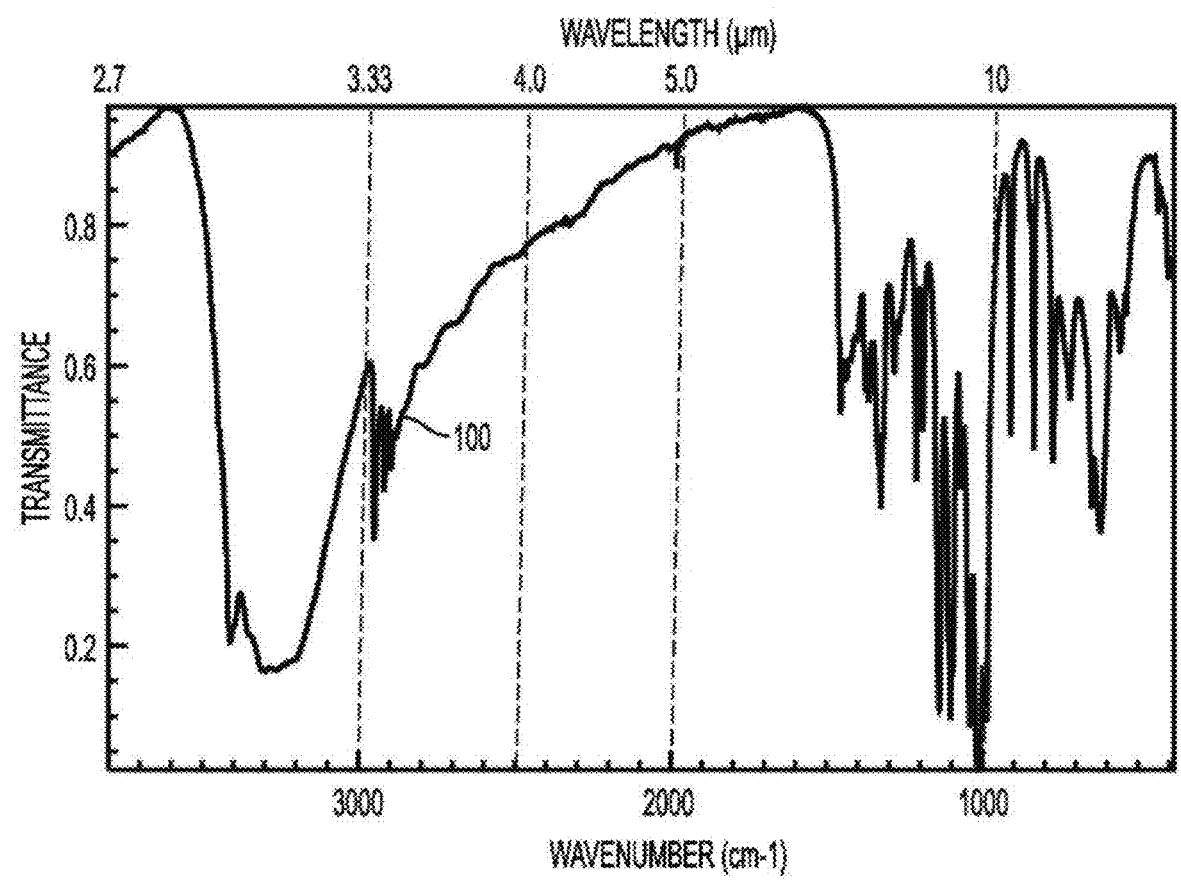
FIG. 1 plots the transmittance versus wavenumber for glucose in the mid-wave and long-wave infrared wavelengths between approximately 2.7 to 12 microns.

As required, detailed embodiments of the present disclosure are disclosed herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Various ailments or diseases may require measurement of the concentration of one or more blood constituents. For example, diabetes may require measurement of the blood glucose and HbA1c levels. On the other hand, diseases or disorders characterized by impaired glucose metabolism may require the measurement of ketone bodies in the blood. Examples of impaired glucose metabolism diseases include Alzheimer's, Parkinson's, Huntington's, and Lou Gehrig's or amyotrophic lateral sclerosis (ALS). Techniques related to near-infrared spectroscopy or hyper-spectral imaging may be particularly advantageous for non-invasive monitoring of some of these blood constituents.

Hyper-spectral images may provide spectral information to identify and distinguish between spectrally similar materials, providing the ability to make proper distinctions among materials with only subtle signature differences. In the SWIR wavelength range, numerous gases, liquids and solids have unique chemical signatures, particularly materials comprising hydro-carbon bonds, O—H bonds, N—H bonds, etc. Therefore, spectroscopy in the SWIR may be attractive for stand-off or remote sensing of materials based on their chemical signature, which may complement other imaging information.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging the sun may be used as the illumination source, and the daytime illumination may comprise direct solar illumination as well as scattered solar (skylight), which is caused by the presence of the atmosphere. However, the sun illumination changes with time of day, clouds or inclement weather may block the sun light, and the sun light is not accessible in the night time. Therefore, it would be advantageous to have a broadband light source covering the SWIR that may be used in place of the sun to identify or classify materials in remote sensing or stand-off detection applications.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

In some instances, it may be desirable to create multiple locations of focused light on the varicose vein. For example, the speed of the treatment may be increased by causing thermal coagulation or occlusion at multiple locations. Multiple collimated or focused light beams may be created in one assembly. In this embodiment, optionally a surface cooling apparatus may be used, where a cooling fluid may be flowed either touching or in close proximity to the skin. Also, in this particular embodiment a cylindrical assembly may optionally be used, where the cylindrical length may be several millimeters in length and defined by a clamp or mount placed on or near the leg. In one embodiment, a window and/or lenslet array is also shown on the cylindrical surface for permitting the light to be incident on the skin and varicose vein at multiple spots. The lenslet array may comprise circular, spherical or cylindrical lenses, depending on the type of spots desired. As before, one advantage of placing the lenslet array in close proximity to the skin and varicose vein may be that a high NA, lens may be used. Also, the input from the lens and/or mirror assembly to the lenslet array may be single large beam, or a plurality of smaller beams. In one embodiment, a plurality of spots may be created by the lenslet array to cause a plurality of locations of thermal coagulation in the varicose vein. Any number of spots may be used and are intended to be covered by this disclosure.

In a non-limiting example, a plurality of spots may be used, or what might be called a fractionated beam. The fractionated laser beam may be added to the laser delivery assembly or delivery head in a number of ways. In one embodiment, a screen-like spatial filter may be placed in the pathway of the beam to be delivered to the biological tissue. The screen-like spatial filter can have opaque regions to block the light and holes or transparent regions, through which the laser beam may pass to the tissue sample. The ratio of opaque to transparent regions may be varied, depending on the application of the laser. In another embodiment, a lenslet array can be used at or near the output interface where the light emerges. In yet another embodiment, at least a part of the delivery fiber from the infrared laser system to the delivery head may be a bundle of fibers, which may comprise a plurality of fiber cores surrounded by cladding regions. The fiber cores can then correspond to the exposed regions, and the cladding areas can approximate the opaque areas not to be exposed to the laser light. As an example, a bundle of fibers may be excited by at least a part of the laser system output, and then the fiber bundle can be fused together and perhaps pulled down to a desired diameter to expose to the tissue sample near the delivery head. In yet another embodiment, a photonic crystal fiber may be used to create the fractionated laser beam. In one non-limiting example, the photonic crystal fiber can be coupled to at least a part of the laser system output at one end, and the other end can be coupled to the delivery head. In a further example, the fractionated laser beam may be generated by a heavily multi-mode fiber, where the speckle pattern at the output may create the high intensity and low intensity spatial pattern at the output. Although several exemplary techniques are provided for creating a fractionated laser beam, other techniques that can be compatible with optical fibers are also intended to be included by this disclosure.

Although the output from a fiber laser may be from a single or multi-mode fiber, different spatial spot sizes or spatial profiles may be beneficial for different applications. For example, in some instances it may be desirable to have a series of spots or a fractionated beam with a grid of spots. In one embodiment, a bundle of fibers or a light pipe with a plurality of guiding cores may be used. In another embodiment, one or more fiber cores may be followed by a lenslet array to create a plurality of collimated or focused beams. In yet another embodiment, a delivery light pipe may be followed by a grid-like structure to divide up the beam into a plurality of spots. These are specific examples of beam shaping, and other apparatuses and methods may also be used and are consistent with this disclosure.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated. In one embodiment, the "optical light" and or "optical beam" and or "light beam" may originate from a fiber, a fiber laser, a laser, a light emitting diode, a lamp, a pump laser, or a light source. In general, the "near-infrared (NIR)" region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye-safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

In this disclosure, the term "damage" refers to affecting a tissue or sample so as to render the tissue or sample inoperable. For instance, if a particular tissue normally emits certain signaling chemicals, then by "damaging" the tissue is meant that the tissue reduces or no longer emits that certain signaling chemical. The term "damage" and or "damaged" may include ablation, melting, charring, killing, or simply incapacitating the chemical emissions from the particular tissue or sample. In one embodiment, histology or histochemical analysis may be used to determine whether a tissue or sample has been damaged.

As used throughout this document, the terms "near" or "about" or the symbol "~" refer to one or more wavelengths of light with wavelengths around the stated wavelength to accomplish the function described. For example, "near 1720 nm" may include wavelengths of between about 1680 nm and 1760 nm. In one embodiment, the term "near 1720 nm" refers to one or more wavelengths of light with a wavelength value anywhere between approximately 1700 nm and 1740 nm. Similarly, as used throughout this document, the term "near 1210 nm" refers to one or wavelengths of light with a wavelength value anywhere between approximately 1170 nm and 1250 nm. In one embodiment, the term "near 1210 nm" refers to one or more wavelengths of light with a wavelength value anywhere between approximately 1190 nm and 1230 nm.

Spectrum for Glucose

One molecule of interest is glucose. The glucose molecule has the chemical formula $C_6H_{12}O_6$, so it has a number of hydro-carbon bonds. An example of the infrared transmittance of glucose 100 is illustrated in FIG. 1. The vibrational spectroscopy shows that the strongest lines for bending and stretching modes of C—H and O—H bonds lie in the wavelength range of approximately 6-12 microns. However, light sources and detectors are more difficult in the mid-wave infrared and long-wave infrared, and there is also strongly increasing water absorption in the human body beyond about 2.5 microns. Although weaker, there are also non-linear combinations of stretching and bending modes between about 2 to 2.5 microns, and first overtone of C—H stretching modes between approximately 1.5-1.8 microns. These signatures may fall in valleys of water absorption, permitting non-invasive detection through the body. In addition, there are yet weaker features from the second overtones and higher-order combinations between about 0.8-1.2 microns; in addition to being weaker, these features may also be masked by absorption in the hemoglobin. Hence, the short-wave infrared (SWIR) wavelength range of approximately 1.4 to 2.5 microns may be an attractive window for near-infrared spectroscopy of blood constituents.

Figure 2:
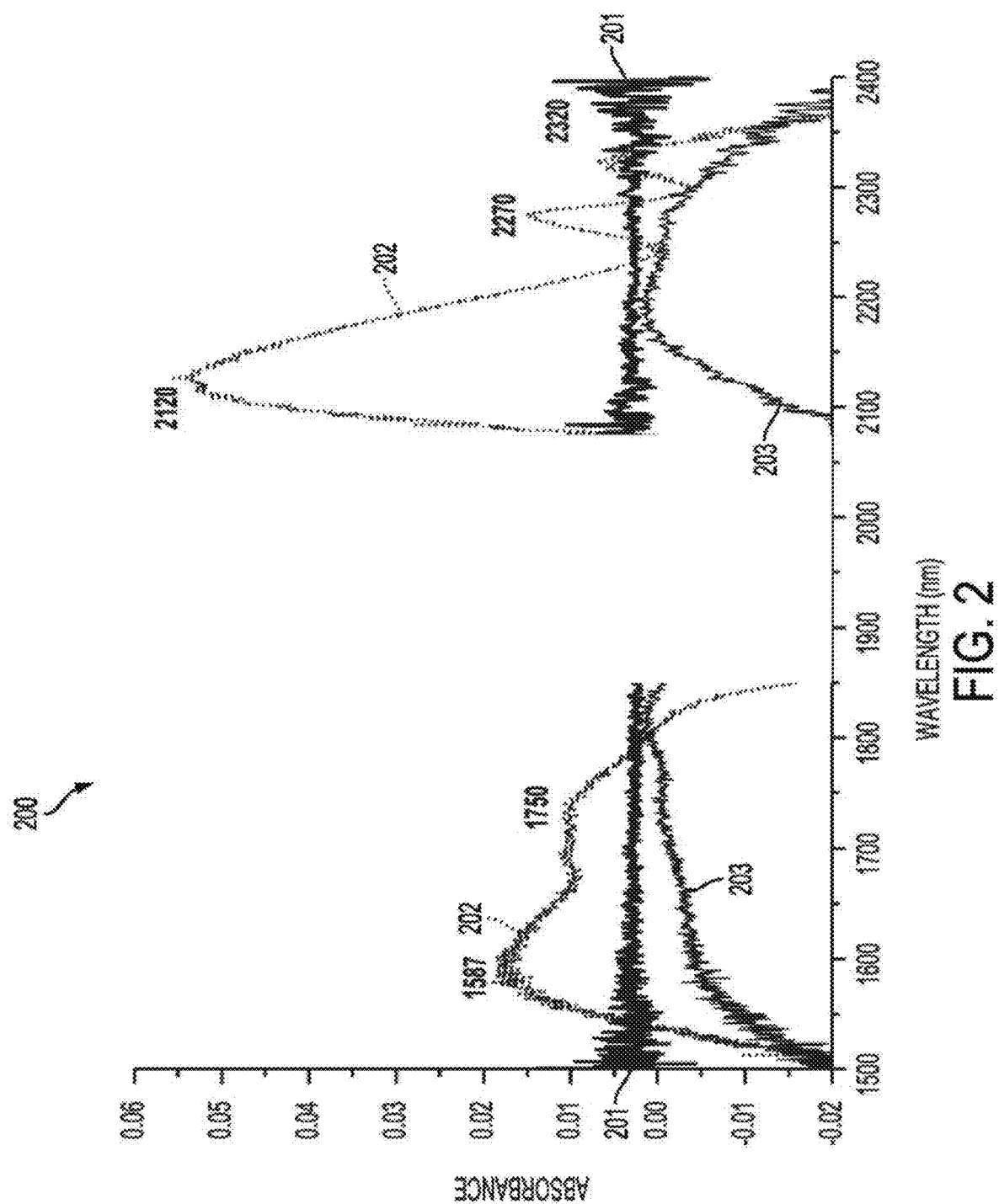
FIG. 2 illustrates measurements of the absorbance of different blood constituents, such as glucose, hemoglobin, and hemoglobin A1c. The measurements are done using an FTIR spectrometer in samples with a 1 mm path length.

As an example, measurements of the optical absorbance 200 of hemoglobin, glucose and HbA1c have been performed using a Fourier-Transform Infrared Spectrometer—FTIR. As FIG. 2 shows, in the SWIR wavelength range hemoglobin is nearly flat in spectrum 201 (the noise at the edges is due to the weaker light signal in the measurements). On the other hand, the glucose absorbance 202 has at least five distinct peaks near 1587 nm, 1750 nm, 2120 nm, 2270 nm and 2320 nm.

Figure 3A:
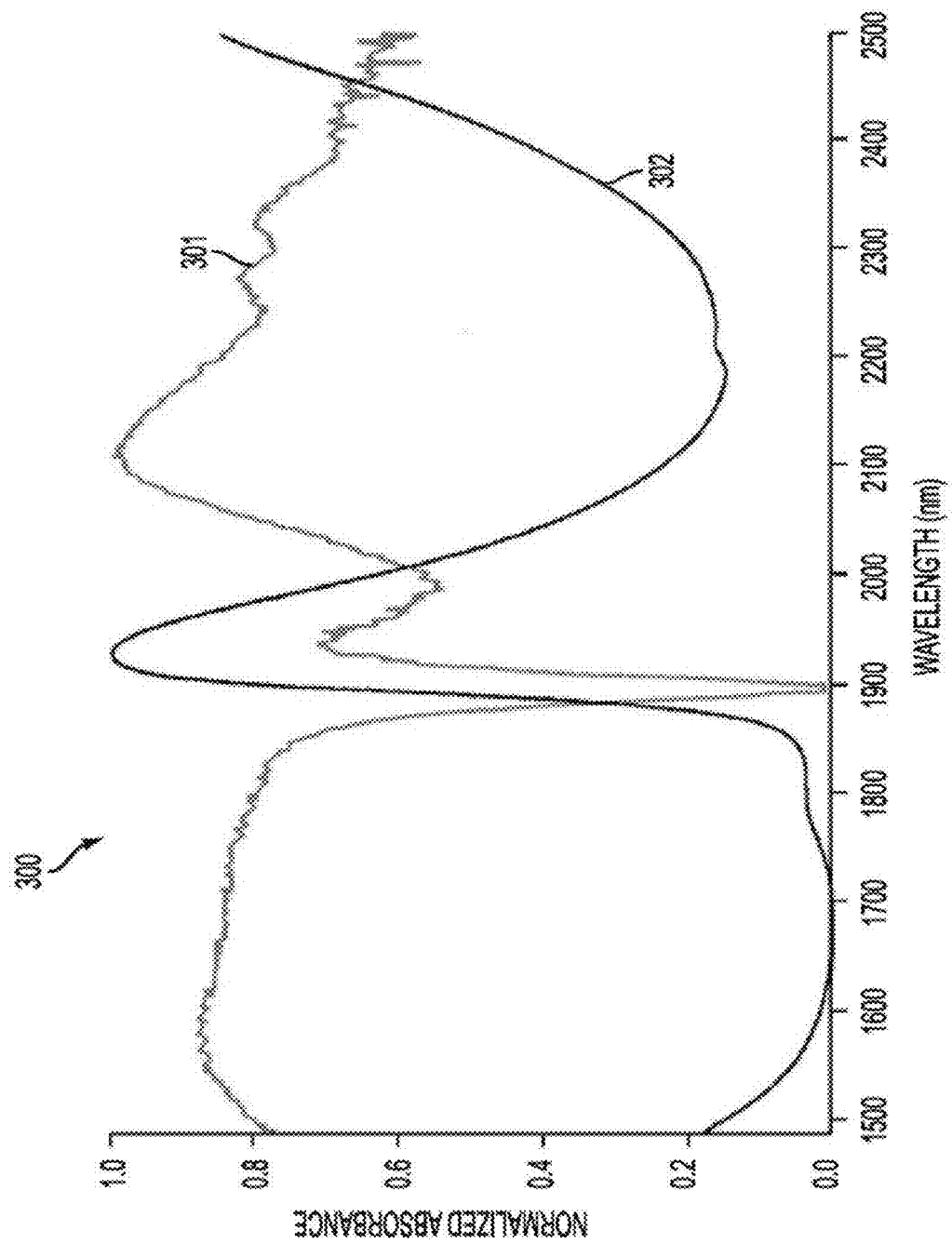
FIG. 3A shows the normalized absorbance of water and glucose (not drawn to scale). Water shows transmission windows between about 1500-1850 nm and 2050-2500 nm.
Figure 3B:
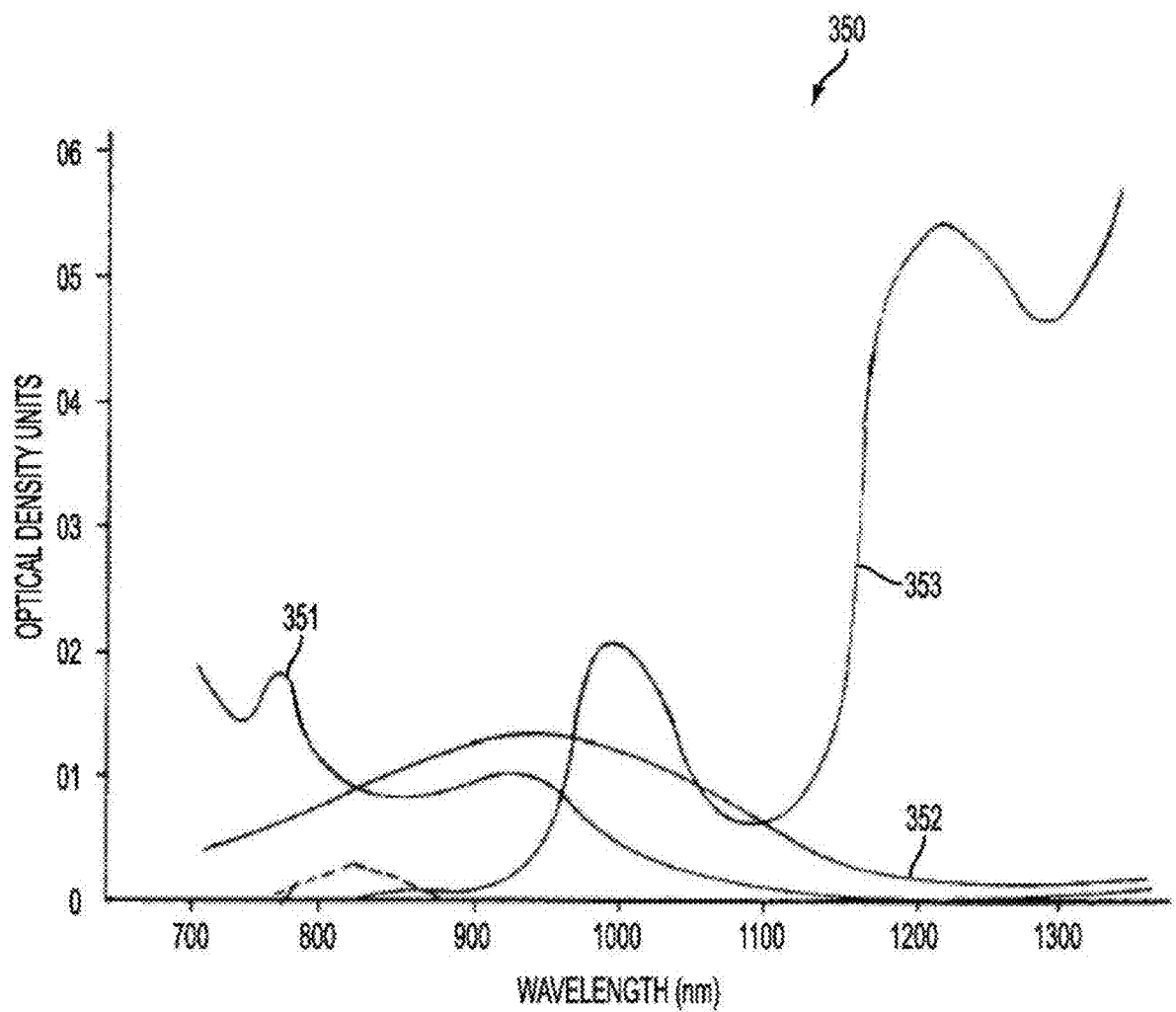
FIG. 3B illustrates the absorbance of hemoglobin and oxygenated hemoglobin overlapped with water.

FIG. 3A overlaps 300 the normalized absorbance of glucose 301 with the absorbance of water 302 (not drawn to scale). It may be seen that water has an absorbance feature between approximately 1850 nm and 2050 nm, but water 302 also has a nice transmission window between approximately 1500-1850 nm and 2050 to 2500 nm. For wavelengths less than about 1100 nm, the absorption of hemoglobin 351 and oxygenated hemoglobin 352 in FIG. 3B has a number of features 350, which may make it more difficult to measure blood constituents. Also, beyond 2500 nm the water absorption becomes considerably stronger over a wide wavelength range. Therefore, an advantageous window for measuring glucose and other blood constituents may be in the SWIR between 1500 and 1850 nm and 2050 to 2500 nm. These are exemplary wavelength ranges, and other ranges can be used that would still fall within the scope of this disclosure.

One further consideration in choosing the laser wavelength is known as the "eye safe" window for wavelengths longer than about 1400 nm. In particular, wavelengths in the eye safe window may not transmit down to the retina of the eye, and therefore, these wavelengths may be less likely to create permanent eye damage. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 4B:
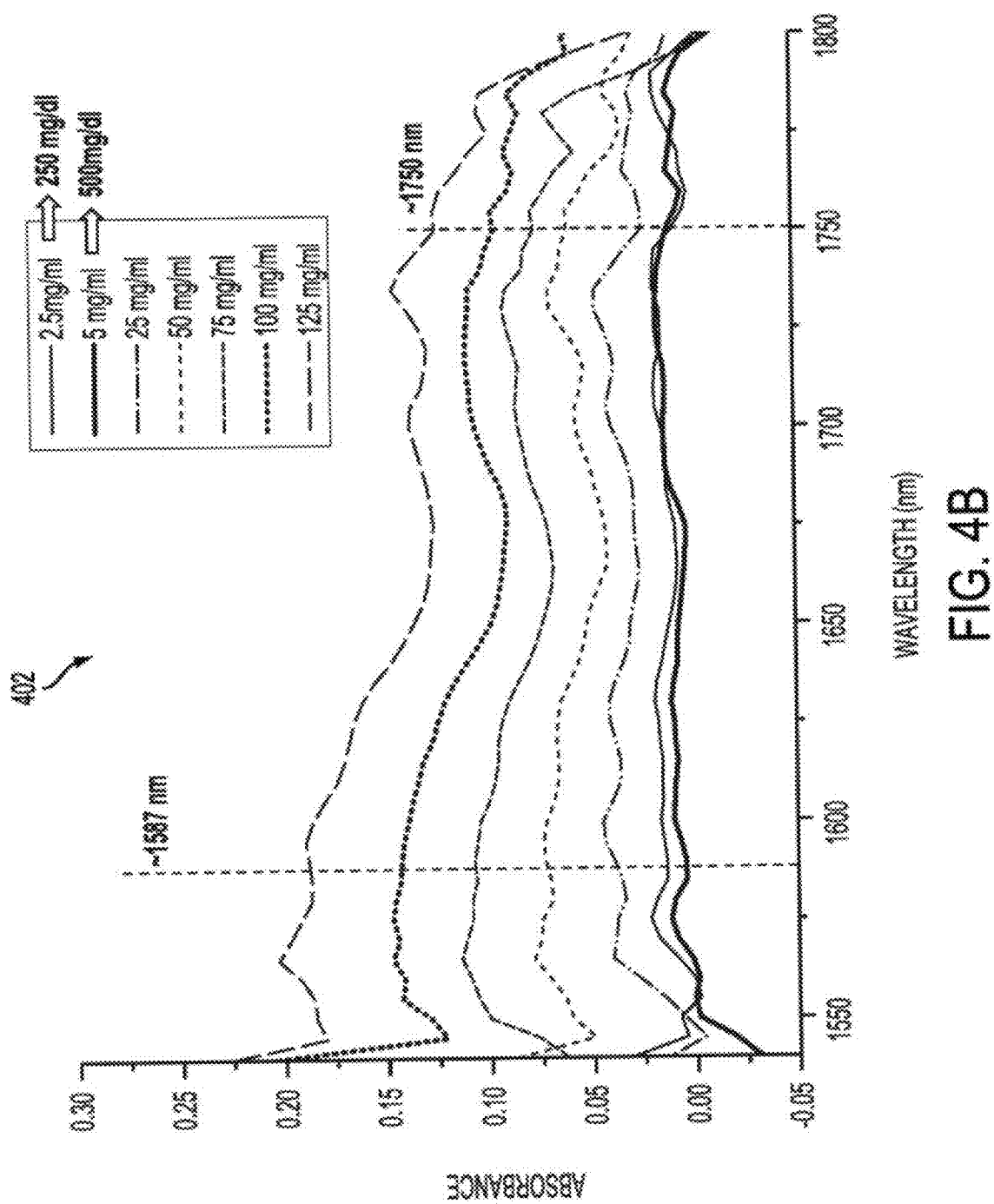
FIG. 4B illustrates measured absorbance in different concentrations of glucose solution over the wavelength range of about 1550 to 1800 nm. The data is collected using a SWIR super-continuum laser with a sample path length of about 10 mm.

Beyond measuring blood constituents such as glucose using FTIR spectrometers, measurements have also been conducted in another embodiment using super-continuum lasers, which will be described later in this disclosure. In this particular embodiment, some of the exemplary preliminary data for glucose absorbance are illustrated in FIGS. 4A and 4B. The optical spectra 401 in FIG. 4A for different levels of glucose concentration in the wavelength range between 2000 and 2400 nm show the three absorption peaks near 2120 nm (2.12 µm), 2270 nm (2.27 µm) and 2320 nm (2.32 µm). Moreover, the optical spectra 402 in FIG. 4B for different levels of glucose concentration in the wavelength range between 1500 and 1800 nm show the two broader absorption peaks near 1587 nm and 1750 nm. It should be appreciated that although data measured with FTIR spectrometers or super-continuum lasers have been illustrated, other light sources can also be used to obtain the data, such as super-luminescent laser diodes, light emitting diodes, a plurality of laser diodes, or even bright lamp sources that generate adequate light in the SWIR.

Figure 5:
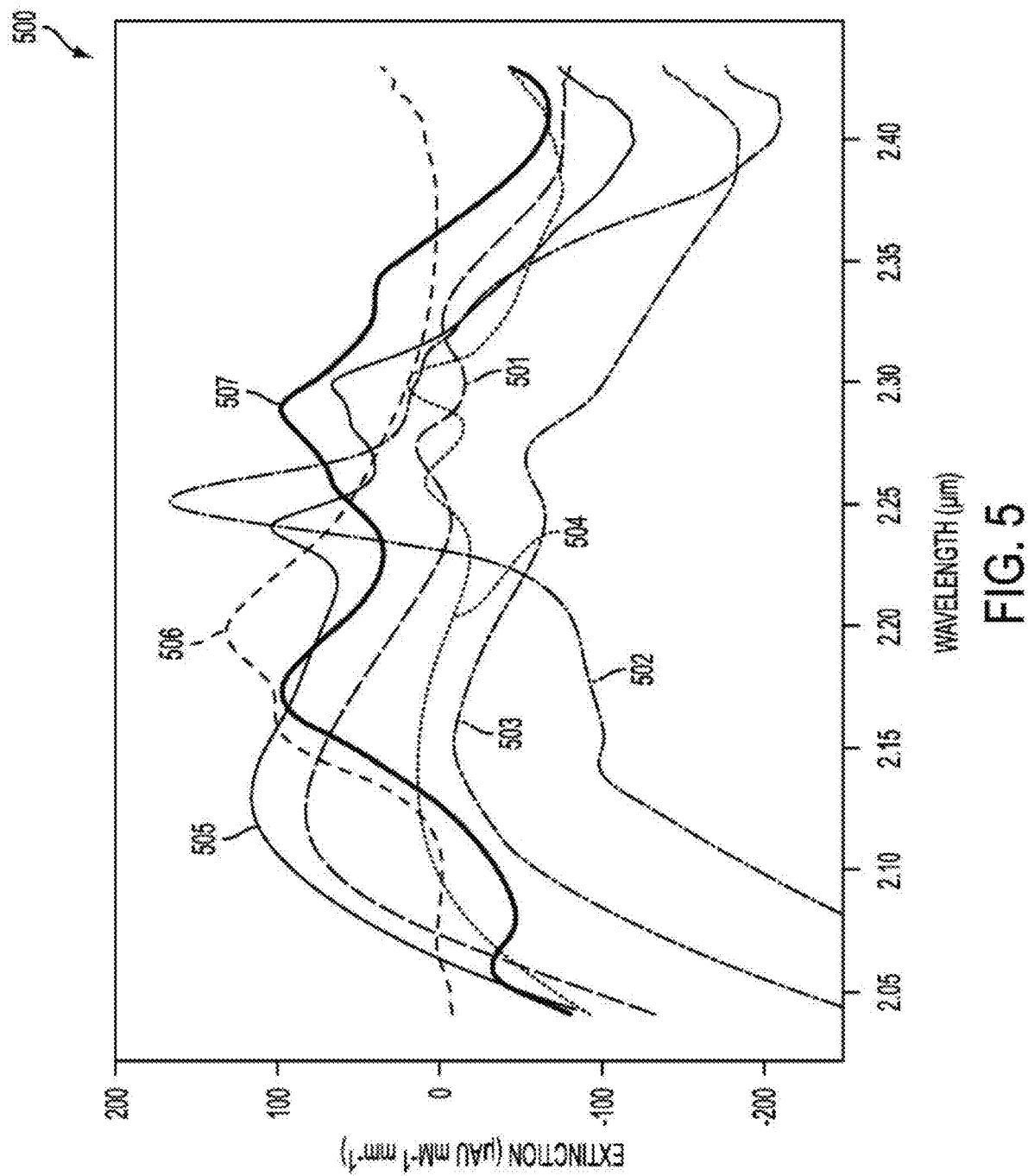
FIG. 5 illustrates the spectrum for different blood constituents in the wavelength range of about 2 to 2.45 microns (2000 to 2450 nm).

Although glucose has a distinctive signature in the SWIR wavelength range, one problem of non-invasive glucose monitoring is that many other blood constituents also have hydro-carbon bonds. Consequently, there can be interfering signals from other constituents in the blood. As an example, FIG. 5 illustrates the spectrum 500 for different blood constituents in the wavelength range of 2 to 2.45 microns. The glucose absorption spectrum 501 can be unique with its three peaks in this wavelength range. However, other blood constituents such as triacetin 502, ascorbate 503, lactate 504, alanine 505, urea 506, and BSA 507 also have spectral features in this wavelength range. To distinguish the glucose 501 from these overlapping spectra, it may be advantageous to have information at multiple wavelengths. In addition, it may be advantageous to use pattern matching algorithms and other software and mathematical methods to identify the blood constituents of interest. In one embodiment, the spectrum may be correlated with a library of known spectra to determine the overlap integrals, and a threshold function may be used to quantify the concentration of different constituents. This is just one way to perform the signal processing, and many other techniques, algorithms, and software may be used and would fall within the scope of this disclosure.

Ketone Bodies Monitoring

Beyond glucose, there are many other blood constituents that may also be of interest for health or disease monitoring. In another embodiment, it may be desirous to monitor the level of ketone bodies in the blood stream. Ketone bodies are three water-soluble compounds that are produced as by-products when fatty acids are broken down for energy in the liver. Two of the three are used as a source of energy in the heart and brain, while the third is a waste product excreted from the body. In particular, the three endogenous ketone bodies are acetone, acetoacetic acid, and beta-hydroxybutyrate or 3-hydroxybutyrate, and the waste product ketone body is acetone.

Ketone bodies may be used for energy, where they are transported from the liver to other tissues. The brain may utilize ketone bodies when sufficient glucose is not available for energy. For instance, this may occur during fasting, strenuous exercise, low carbohydrate, ketogenic diet and in neonates. Unlike most other tissues that have additional energy sources such as fatty acids during periods of low blood glucose, the brain cannot break down fatty acids and relies instead on ketones. In one embodiment, these ketone bodies are detected.

Ketone bodies may also be used for reducing or eliminating symptoms of diseases or disorders characterized by impaired glucose metabolism. For example, diseases associated with reduced neuronal metabolism of glucose include Parkinson's disease, Alzheimer's disease, amyotrophic lateral sclerosis (ALS, also called Lou Gehrig's disease), Huntington's disease and epilepsy. In one embodiment, monitoring of alternate sources of ketone bodies that may be administered orally as a dietary supplement or in a nutritional composition to counteract some of the glucose metabolism impairments is performed. However, if ketone bodies supplements are provided, there is also a need to monitor the ketone level in the blood stream. For instance, if elevated levels of ketone bodies are present in the body, this may lead to ketosis; hyperketonemia is also an elevated level of ketone bodies in the blood. In addition, both acetoacetic acid and beta-hydroxybutyric acid are acidic, and, if levels of these ketone bodies are too high, the pH of the blood may drop, resulting in ketoacidosis.

The general formula for ketones is $C_nH_{2n}O$. In organic chemistry, a ketone is an organic compound with the structure RC(=O)R', where R and R' can be a variety of carbon-containing substituents. It features a carbonyl group (C=O) bonded to two other carbon atoms. Because the ketones contain the hydrocarbon bonds, there might be expected to be features in the SWIR, similar in structure to those found for glucose.

Figure 6:
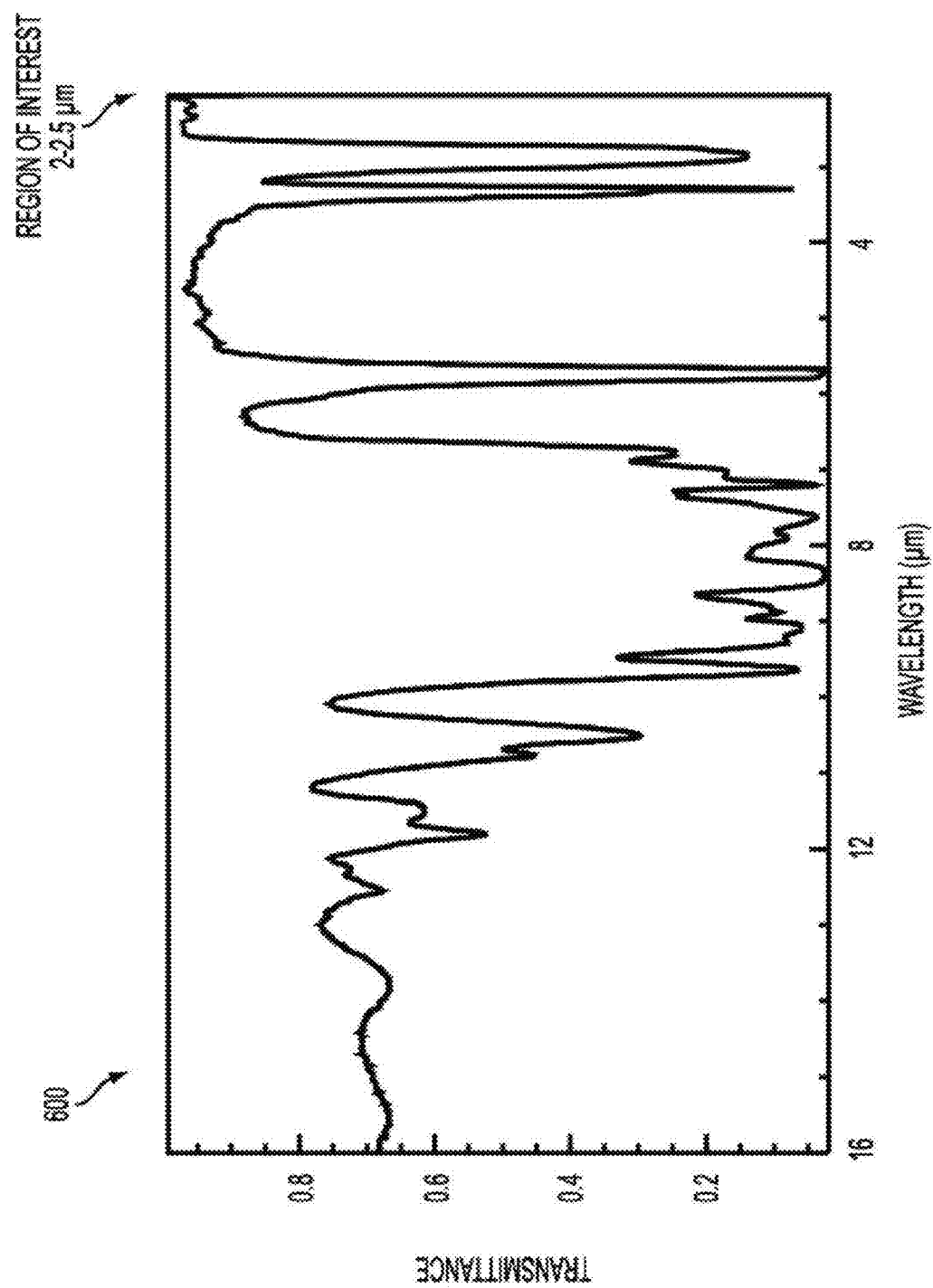
FIG. 6 shows the transmittance versus wavelength in microns for the ketone 3-hydroxybutyrate. The wavelength range is approximately 2 to 16 microns.

The infrared spectrum 600 for the ketone 3-hydroxybutyrate is illustrated in FIG. 6. Just as in glucose, there are significant features in the mid- and long-wave infrared between 6 to 12 microns, but these may be difficult to observe non-invasively. On the other hand, there are some features in the SWIR that may be weaker, but they could potentially be observed non-invasively, perhaps through blood and water.

Figure 7:
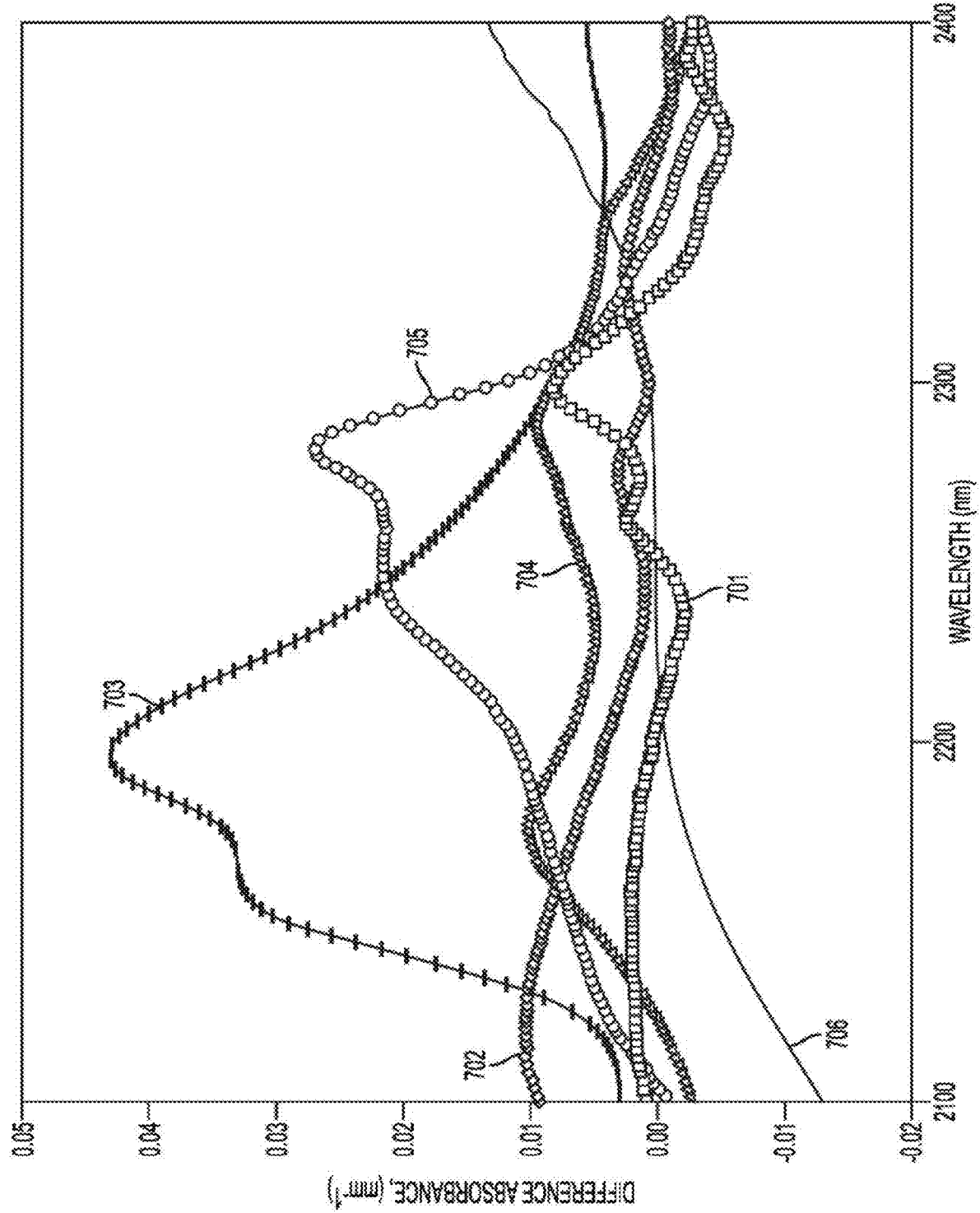
FIG. 7 illustrates the optical absorbance for ketones as well as some other blood constituents in the wavelength range of about 2100 to 2400 nm.

The optical spectra 700 for ketones as well as some other blood constituents are exemplified in FIG. 7 in the wavelength range of 2100 nm to 2400 nm. In this embodiment, the absorbance for ketones is 701, while the absorbance for glucose is 702. However, there are also features in this wavelength range for other blood constituents, such as urea 703, albumin or blood protein 704, creatinine 705, and nitrite 706. In this wavelength range of 2100 to 2400 nm, the features for ketone 701 seem more spectrally pronounced than even glucose.

Different signal processing techniques can be used to enhance the spectral differences between different constituents. In one embodiment, the first or second derivatives of the spectra may enable better discrimination between substances. The first derivative may help remove any flat offset or background, while the second derivative may help to remove any sloped offset or background. In some instances, the first or second derivative may be applied after curve fitting or smoothing the reflectance, transmittance, or absorbance. For example, FIG. 8A illustrates the derivative spectra for ketone 801 and glucose 802, which can be distinguished from the derivative spectra for protein 803, urea 804 and creatinine 805. Based on FIG. 8A, it appears that ketones 801 may have a more pronounced difference than even glucose 802 in the wavelength range between 2100 and 2400 nm. Therefore, ketone bodies should also be capable of being monitored using a non-invasive optical technique in the SWIR, and a different pattern matching library could be used for glucose and ketones.

Hemoglobin A1c Monitoring

Another blood constituent that may be of interest for monitoring of health or diseases is hemoglobin A1c, also known as HbA1c or glycated hemoglobin (glycol-hemoglobin or glycosylated hemoglobin). HbA1c is a form of hemoglobin that is measured primarily to identify the average plasma glucose concentration over prolonged periods of time. Thus, HbA1c may serve as a marker for average blood glucose levels over the previous months prior to the measurements.

In one embodiment, when a physician suspects that a patient may be diabetic, the measurement of HbA1c may be one of the first tests that are conducted. An HbA1c level less than approximately 6% may be considered normal. On the other hand, an HbA1c level greater than approximately 6.5% may be considered to be diabetic. In diabetes mellitus, higher amounts of HbA1c indicate poorer control of blood glucose levels. Thus, monitoring the HbA1c in diabetic patients may improve treatment. Current techniques for measuring HbA1c require drawing blood, which may be inconvenient and painful. The point-of-care devices use immunoassay or boronate affinity chromatography, as an example. Thus, there is also an unmet need for non-invasive monitoring of HbA1c.

FIG. 2 illustrates the FTIR measurements of HbA1c absorbance 203 over the wavelength range between 1500 and 2400 nm for a concentration of approximately 1 mg/ml. Whereas the absorbance of hemoglobin 201 over this wavelength range is approximately flat, the HbA1c absorbance 203 shows broad features and distinct curvature. Although the HbA1c absorbance 203 does not appear to exhibit as pronounced features as glucose 202, the non-invasive SWIR measurement should be able to detect HbA1c with appropriate pattern matching algorithms. Moreover, the spectrum for HbA1c may be further enhanced by using first or second derivative data, as seen for ketones in FIG. 8A. Beyond absorption, reflectance, or transmission spectroscopy, it may also be possible to detect blood constituents such as HbA1c using Raman spectroscopy or surface-enhanced Raman spectroscopy. In general, Raman spectroscopy may require higher optical power levels.

As an illustration, non-invasive measurement of blood constituents such as glucose, ketone bodies, and HbA1c has been discussed thus far. However, other blood constituents can also be measured using similar techniques, and these are also intended to be covered by this disclosure. In other embodiments, blood constituents such as proteins, albumin, urea, creatinine or nitrites could also be measured. For instance, the same type of SWIR optical techniques might be used, but the pattern matching algorithms and software could use different library features or functions for the different constituents.

Figure 8B:
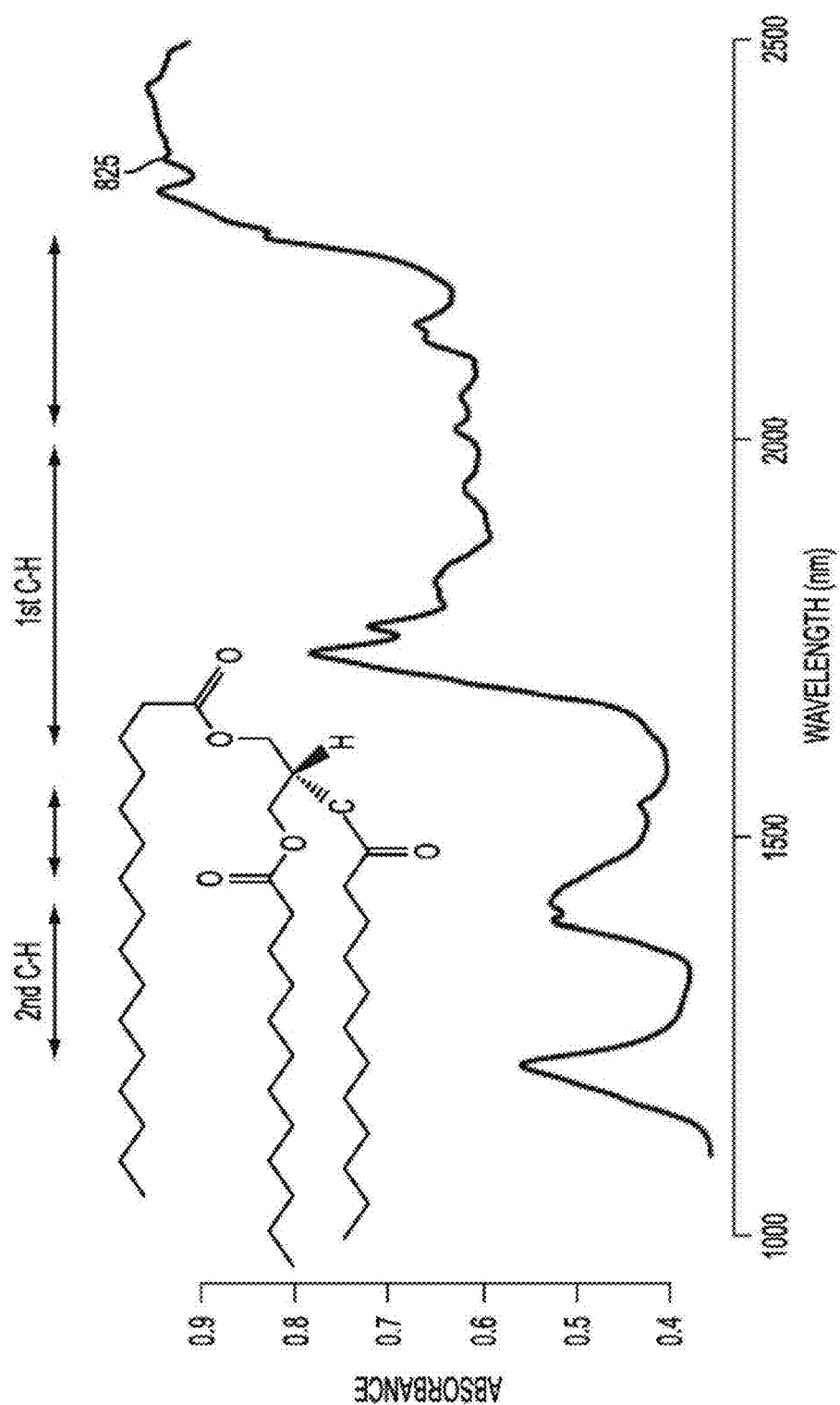
FIG. 8B illustrates the near infrared absorbance for triglyceride.

In yet another embodiment, the optical techniques described in this disclosure could also be used to measure levels of triglycerides. Triglycerides are bundles of fats that may be found in the blood stream, particularly after ingesting meals. The body manufactures triglycerides from carbohydrates and fatty foods that are eaten. In other words, triglycerides are the body's storage form of fat. Triglycerides are comprised of three fatty acids attached to a glycerol molecule, and measuring the level of triglycerides may be important for diabetics. The triglyceride levels or concentrations in blood may be rated as follows: desirable or normal may be less than 150 mg/dl; borderline high may be 150-199 mg/dl; high may be 200-499 mg/dl; and very high may be 500 mg/dl or greater. FIG. 8B illustrates one example of the near-infrared absorbance 825 for triglycerides. There are distinct absorbance peaks in the spectrum that should be measurable. The characteristic absorption bands may be assigned as follows: (a) the first overtones of C—H stretching vibrations (1600-1900 nm); (b) the region of second overtones of C—H stretching vibrations (1100-1250 nm); and, (c) two regions (2000-2200 nm and 1350-1500 nm) that comprise bands due to combinations of C—H stretching vibrations and other vibrational modes.

Figure 8C:
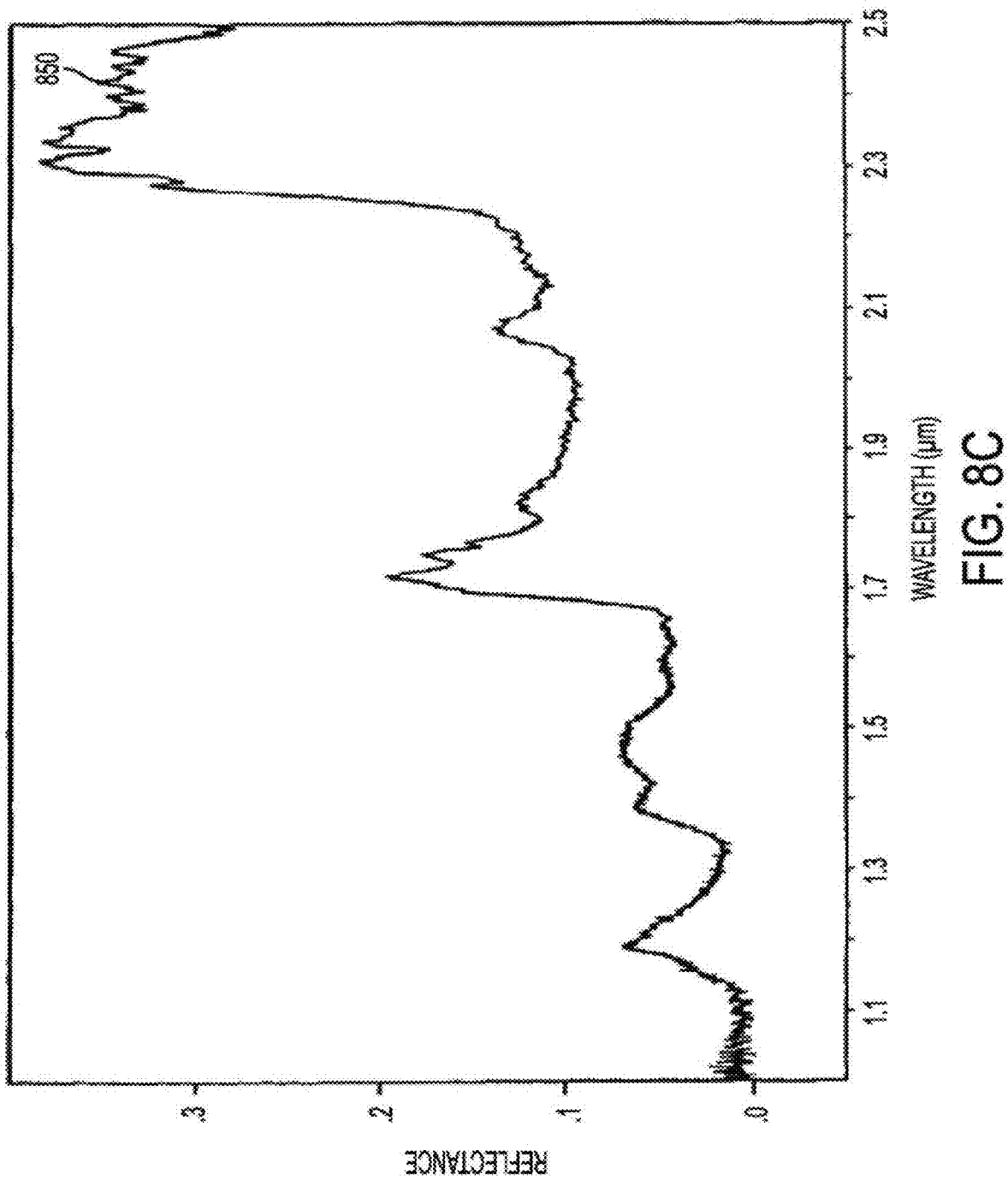
FIG. 8C shows the near-infrared reflectance spectrum for cholesterol.

A further example of blood compositions that can be detected or measured using near-infrared light includes cholesterol monitoring. For example, FIG. 8C shows the near-infrared reflectance spectrum for cholesterol 850 with wavelength in microns (μm). Distinct absorption peaks are observable near 1210 nm (1.21 μm), 1720 nm (1.72 μm), and between 2300-2500 nm (2.3-2.5 μm). Also, there are other features near 1450 nm (1.45 μm) and 2050 nm (2.05 μm). In FIG. 8D the near-infrared reflectances 875 are displayed versus wavelength (nm) for various blood constituents. The spectrum for cholesterol 876 is overlaid with glucose 877, albumin 878, uric acid 879, and urea 880. As may be noted from FIG. 8D, at about 1720 nm and 2300 nm, cholesterol 876 reaches approximate reflectance peaks, while some of the other analytes are in a more gradual mode. Various signal processing methods may be used to identify and quantify the concentration of cholesterol 876 and/or glucose 877, or some of the other blood constituents.

As illustrated by FIGS. 5 and 7, one of the issues in measuring a particular blood constituent is the interfering and overlapping signal from other blood constituents. The selection of the constituent of interest may be improved using a number of techniques. For example, a higher light level or intensity may improve the signal-to-noise ratio for the measurement. Second, mathematical modeling and signal processing methodologies may help to reduce the interference, such as multivariate techniques, multiple linear regression, and factor-based algorithms, for example. For instance, a number of mathematical approaches include multiple linear regression, partial least squares, and principal component regression (PCR). Also, as illustrated in FIG. 8A, various mathematical derivatives, including the first and second derivatives, may help to accentuate differences between spectra. In addition, by using a wider wavelength range and using more sampling wavelengths may improve the ability to discriminate one signal from another. Moreover, it may be advantageous to pulse the light source with a particular pulse width and pulse repetition rate, and then the detection system can measure the pulsed light returned from or transmitted through the tissue. Using a lock-in type technique (e.g., detecting at the same frequency as the pulsed light source and also possibly phase locked to the same signal), the detection system may be able to reject background or spurious signals and increase the signal-to-noise ratio of the measurement. In one particular embodiment, high signal-to-noise ratio may be achieved using a fiber-based super-continuum (SC) light source (described further herein). Other light sources may also be used, including a plurality of laser diodes, super-luminescent laser diodes, or fiber lasers. In one embodiment, an all-fiber-integrated, high-powered SC light source may be elegant for its simplicity. The light may be first generated from a seed laser diode (LD). For example, the seed LD may be a distributed feedback (DFB) laser diode with a wavelength near 1542 nm or 1550 nm, with approximately 0.5-2.0 ns pulsed output, and with a pulse repetition rate between one kilohertz and about 100 MHz or more.

Beyond having a pulse width, the laser output can also have a preferred repetition rate. For pulse repetition rates above around 10 MHz, where multiple pulses fall within a thermal diffusion time, the tissue response may be more related to the energy deposited or the fluence of the laser beam. The separation between pulses or a sub-group of pulses may also be selected so that the tissue sample can reach thermal equilibrium between pulses. Also, the pulse pattern may or may not be periodic. In one embodiment, there may be several pulses used per spot, where the pulse pattern is selected to obtain a desired thermal profile. The laser beam may then be moved to a new spot and then another pulse train delivered to that spot. In one embodiment, there can be several seconds of pre-cooling, the laser can be exposed on the tissue for several seconds, and then there may also be post-cooling. Although particular examples of laser duration and repetition rate are described, other values may also be used consistent with this disclosure. For example, depending on the application and mechanisms, the pulse rate could range all the way from continuous wave to 100's of Megahertz.

The above are just examples of some of the methods of improving the ability to discriminate between different constituents, but other techniques may also be used and are intended to be covered by this disclosure.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. In the following some exemplary detection systems are described.

Interference from Skin

Several proposed non-invasive glucose monitoring techniques rely on transmission, absorption, and/or diffuse reflection through the skin to measure blood constituents or blood analytes in veins, arteries, capillaries or in the tissue itself. However, on top of the interference from other blood constituents or analytes, the skin also introduces significant interference. For example, chemical, structural, and physiological variations occur that may produce relatively large and nonlinear changes in the optical properties of the tissue sample. In one embodiment, the near-infrared reflectance or absorbance spectrum may be a complex combination of the tissue scattering properties that result from the concentration and characteristics of a multiplicity of tissue components including water, fat, protein, collagen, elastin, and/or glucose. Moreover, the optical properties of the skin may also change with environmental factors such as humidity, temperature and pressure. Physiological variation may also cause changes in the tissue measurement over time and may vary based on lifestyle, health, aging, etc. The structure and composition of skin may also vary widely among individuals, between different sites within an individual, and over time on the same individual. Thus, the skin introduces a dynamic interference signal that may have a wide variation due to a number of parameters.

Figure 9:
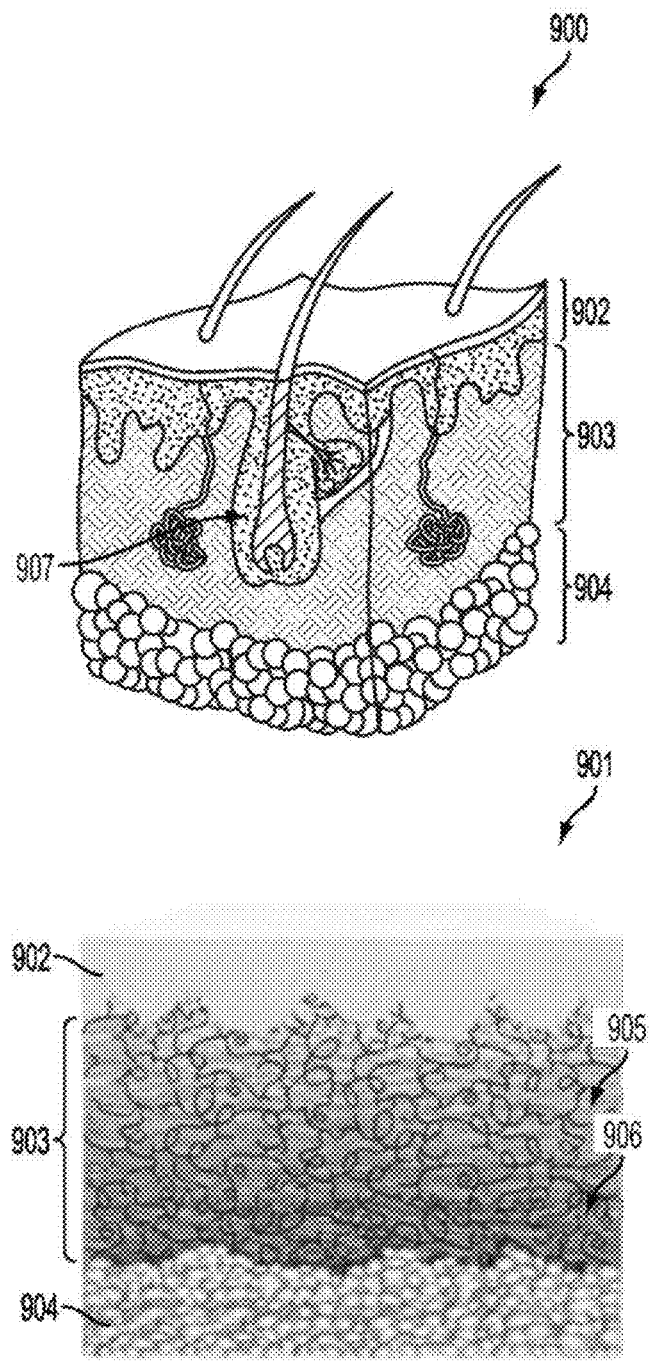
FIG. 9 shows a schematic of the human skin. In particular, the dermis may comprise significant amounts of collagen, elastin, lipids, and water.

FIG. 9 shows a schematic cross-section of human skin 900, 901. The top layer of the skin is epidermis 902, followed by a layer of dermis 903 and then subcutaneous fat 904 below the dermis. The epidermis 902, with a thickness of approximately 10-150 microns, may provide a barrier to infection and loss of moisture and other body constituents. The dermis 903 ranges in thickness from approximately 0.5 mm to 4 mm (averages approximately 1.2 mm over most of the body) and may provide the mechanical strength and elasticity of skin.

In the dermis 903, water may account for approximately 70% of the volume. The next most abundant constituent in the dermis 903 may be collagen 905, a fibrous protein comprising 70-75% of the dry weight of the dermis 903. Elastin fibers 906, also a protein, may also be plentiful in the dermis 903, although they constitute a smaller portion of the bulk. In addition, the dermis 903 may contain a variety of structures (e.g., sweat glands, hair follicles with adipose rich sebaceous glands 907 near their roots, and blood vessels) and other cellular constituents.

Below the dermis 903 lies the subcutaneous layer 904 comprising mostly adipose tissue. The subcutaneous layer 904 may be by volume approximately 10% water and may be comprised primarily of cells rich in triglycerides or fat. With this complicated structure of the skin 900, 901, the concentration of glucose may vary in each layer according to a variety of factors including the water content, the relative sizes of the fluid compartments, the distribution of capillaries, the perfusion of blood, the glucose uptake of cells, the concentration of glucose in blood, and the driving forces (e.g., osmotic pressure) behind diffusion.

Figure 10:
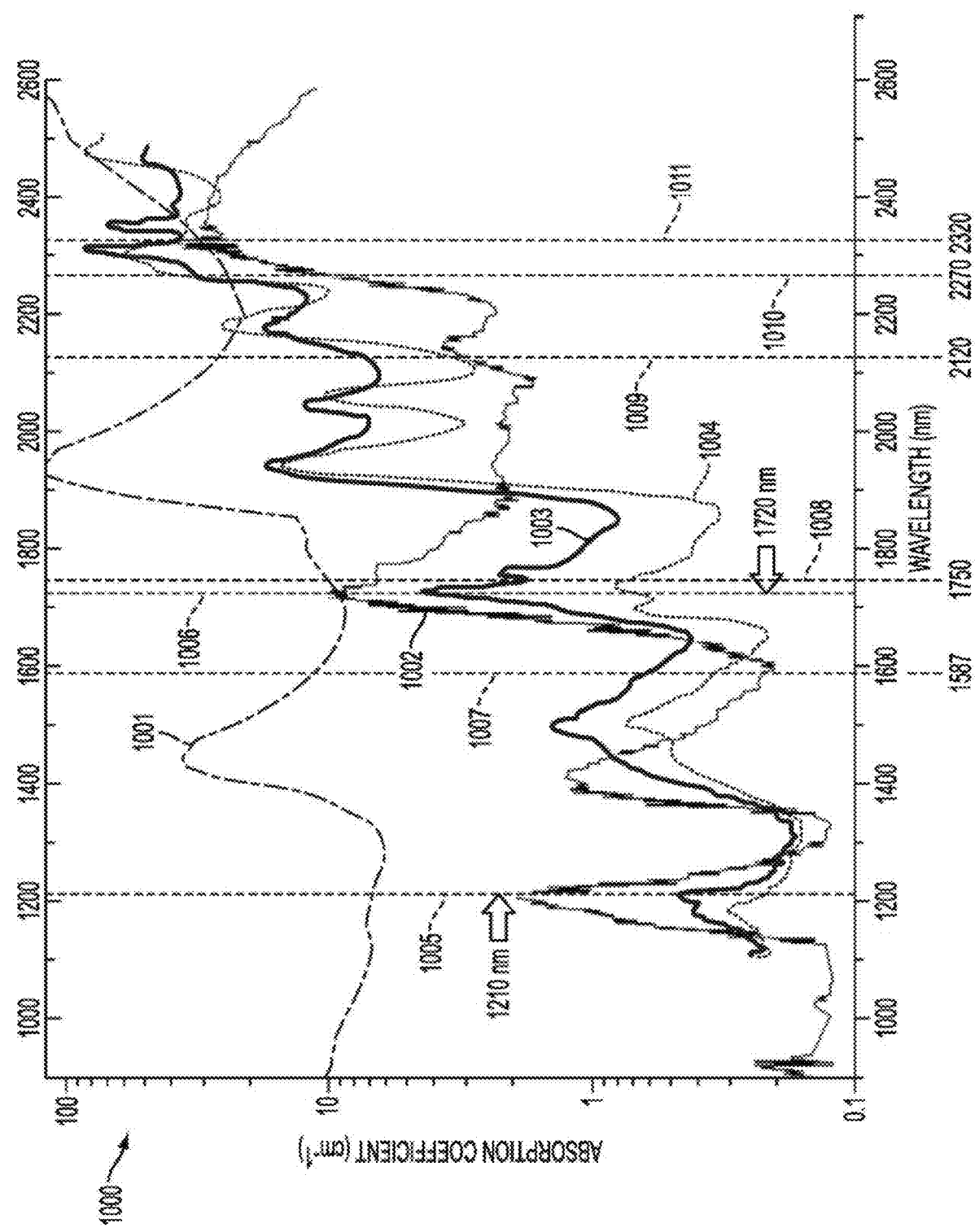
FIG. 10 illustrates the absorption coefficients for water (including scattering), adipose, collagen, and elastin.

To better understand the interference that the skin introduces when attempting to measure glucose, the absorption coefficient for the various skin constituents should be examined. For example, FIG. 10 illustrates 1000 the absorption coefficients for water (including scattering) 1001, adipose 1002, collagen 1003 and elastin 1004. Note that the absorption curves for water 1001 and adipose 1002 are calibrated, whereas the absorption curves for collagen 1003 and elastin 1004 are in arbitrary units. Also shown are vertical lines demarcating the wavelengths near 1210 nm 1005 and 1720 nm 1006. In general, the water absorption increases with increasing wavelength. With the increasing absorption beyond about 2000 nm, it may be difficult to achieve deeper penetration into biological tissue in the infrared wavelengths beyond approximately 2500 nm.

Although the absorption coefficient may be useful for determining the material in which light of a certain infrared wavelength will be absorbed, to determine the penetration depth of the light of a certain wavelength may also require the addition of scattering loss to the curves. For example, the water curve 1001 includes the scattering loss curve in addition to the water absorption. In particular, the scattering loss can be significantly higher at shorter wavelengths. In one embodiment, near the wavelength of 1720 nm (vertical line 1006 shown in FIG. 10), the adipose absorption 1002 can still be higher than the water plus scattering loss 1001. For tissue that contains adipose, collagen and elastin, such as the dermis of the skin, the total absorption can exceed the light energy lost to water absorption and light scattering at 1720 nm. On the other hand, at 1210 nm the adipose absorption 1002 can be considerably lower than the water plus scattering loss 1001, particularly since the scattering loss can be dominant at these shorter wavelengths.

The interference for glucose lines observed through skin may be illustrated by overlaying the glucose lines over the absorption curves 1000 for the skin constituents. For example, FIG. 2 illustrated that the glucose absorption 202 included features centered around 1587 nm, 1750 nm, 2120 nm, 2270 nm and 2320 nm. On FIG. 10 vertical lines have been drawn at the glucose line wavelengths of 1587 nm 1007, 1750 nm 1008, 2120 nm 1009, 2270 nm 1010 and 2320 nm 1011. In one embodiment, it may be difficult to detect the glucose lines near 1750 nm 1008, 2270 nm 1010 and 2320 nm 1011 due to significant spectral interference from other skin constituents. On the other hand, the glucose line near 1587 m 1007 may be more easily detected because it peaks while most of the other skin constituents are sloped downward toward an absorption valley. Moreover, the glucose line near 2120 nm 1009 may also be detectable for similar reasons, although adipose may have conflicting behavior due to local absorption minimum and maximum nearby in wavelength.

Thus, beyond the problem of other blood constituents or analytes having overlapping spectral features (e.g., FIG. 5), it may be difficult to observe glucose spectral signatures through the skin and its constituents of water, adipose, collagen and elastin. One approach to overcoming this difficulty may be to try to measure the blood constituents in veins that are located at relatively shallow distances below the skin. Veins may be more beneficial for the measurement than arteries, since arteries tend to be located at deeper levels below the skin. Also, in one embodiment it may be advantageous to use a differential measurement to subtract out some of the interfering absorption lines from the skin. For example, an instrument head may be designed to place one probe above a region of skin over a blood vein, while a second probe may be placed at a region of the skin without a noticeable blood vein below it. Then, by differencing the signals from the two probes, at least part of the skin interference may be cancelled out.

Figure 11:
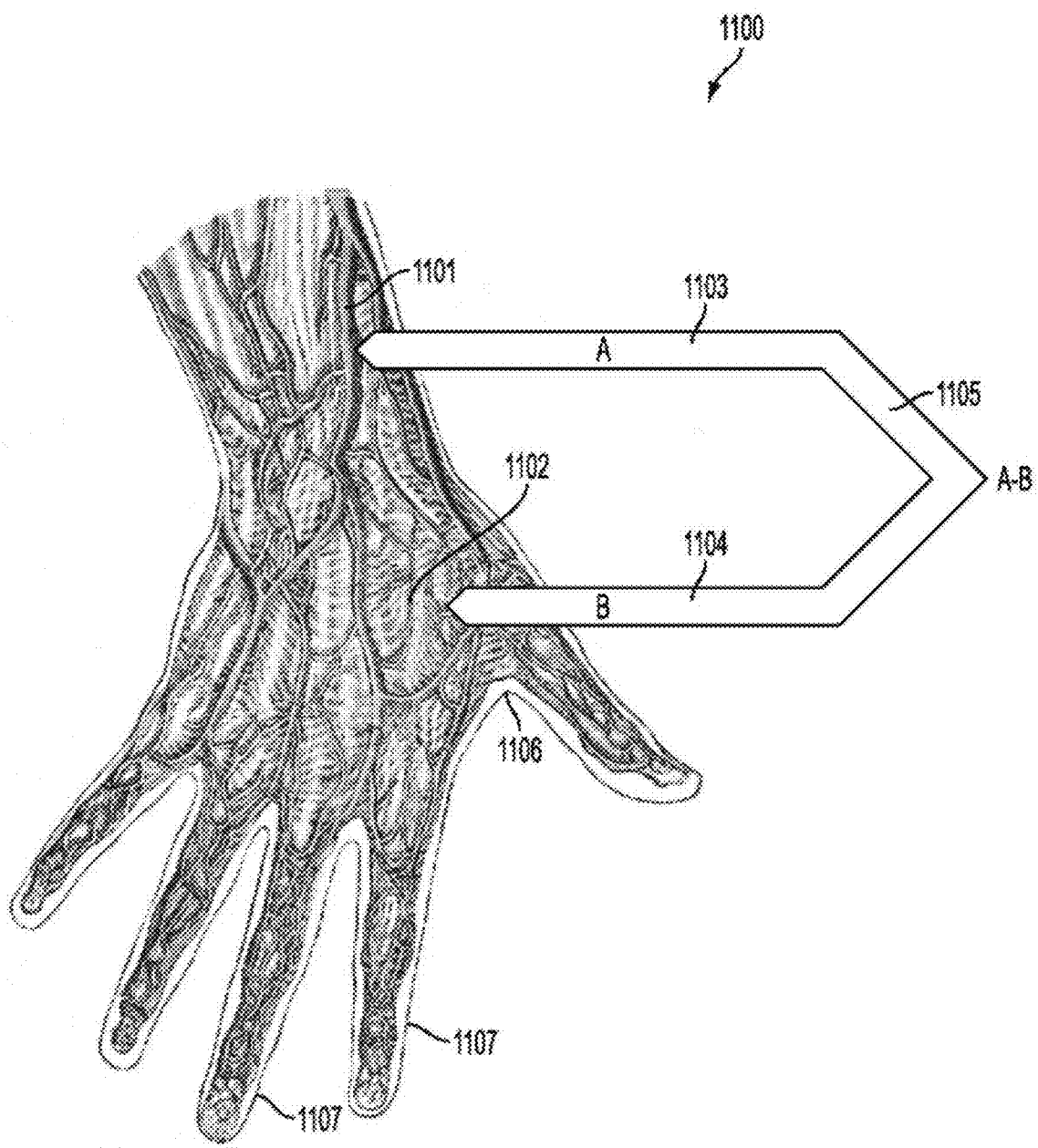
FIG. 11 shows the dorsal of the hand, where a differential measurement may be made to at least partially compensate for or subtract out the skin interference.
Figure 12:
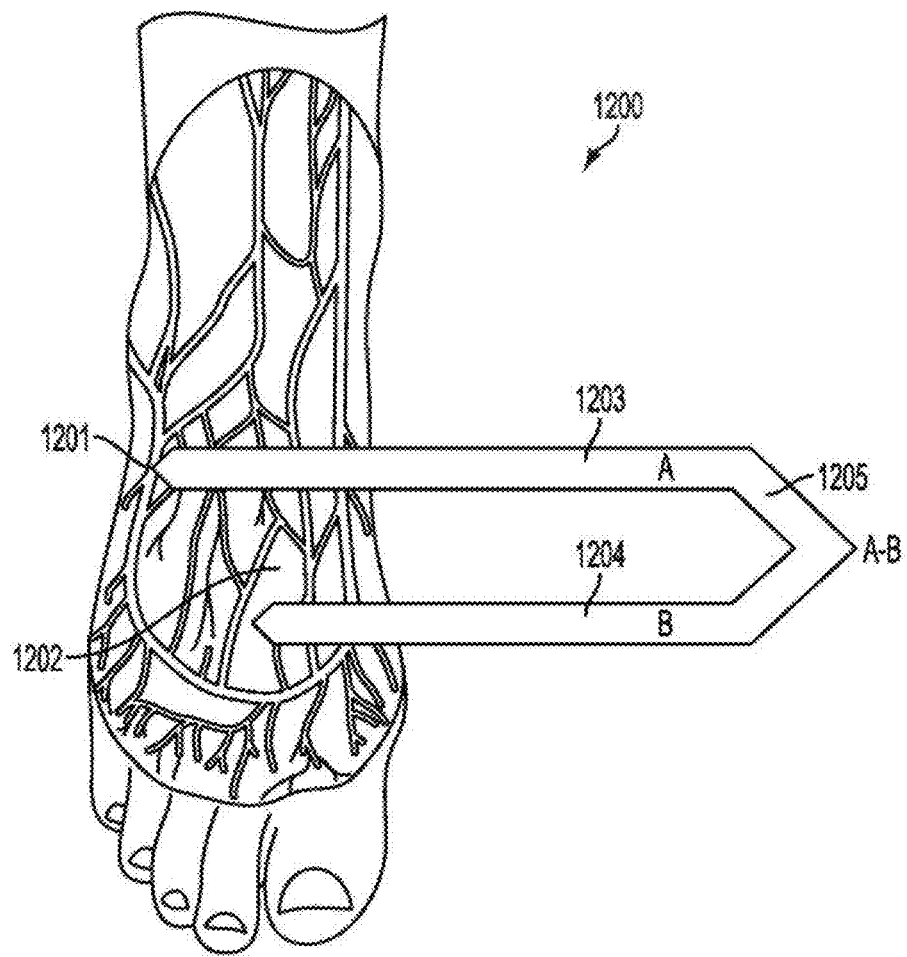
FIG. 12 shows the dorsal of the foot, where a differential measurement may be made to at least partially compensate for or subtract out the skin interference.

Two representative embodiments for performing such a differential measurement are illustrated in FIG. 11 and FIG. 12. In one embodiment shown in FIG. 11, the dorsal of the hand 1100 may be used for measuring blood constituents or analytes. The dorsal of the hand 1100 may have regions that have distinct veins 1101 as well as regions where the veins are not as shallow or pronounced 1102. By stretching the hand and leaning it backwards, the veins 1101 may be accentuated in some cases. A near-infrared diffuse reflectance measurement may be performed by placing one probe 1103 above the vein-rich region 1101. To turn this into a differential measurement, a second probe 1104 may be placed above a region without distinct veins 1102. Then, the outputs from the two probes may be subtracted 1105 to at least partially cancel out the features from the skin. The subtraction may be done preferably in the electrical domain, although it can also be performed in the optical domain or digitally/mathematically using sampled data based on the electrical and/or optical signals. Although one example of using the dorsal of the hand 1100 is shown, many other parts of the hand can be used within the scope of this disclosure. For example, alternate methods may use transmission through the webbing between the thumb and the fingers 1106, or transmission or diffuse reflection through the tips of the fingers 1107.

In another embodiment, the dorsal of the foot 1200 may be used instead of the hand. One advantage of such a configuration may be that for self-testing by a user, the foot may be easier to position the instrument using both hands. One probe 1203 may be placed over regions where there are more distinct veins 1201, and a near-infrared diffuse reflectance measurement may be made. For a differential measurement, a second probe 1204 may be placed over a region with less prominent veins 1202, and then the two probe signals may be subtracted, either electronically or optically, or may be digitized/sampled and processed mathematically depending on the particular application and implementation. As with the hand, the differential measurements may be intended to compensate for or subtract out (at least in part) the interference from the skin. Since two regions are used in close proximity on the same body part, this may also aid in removing some variability in the skin from environmental effects such as temperature, humidity, or pressure. In addition, it may be advantageous to first treat the skin before the measurement, by perhaps wiping with a cloth or treated cotton ball, applying some sort of cream, or placing an ice cube or chilled bag over the region of interest.

Although two embodiments have been described, many other locations on the body may be used using a single or differential probe within the scope of this disclosure. In yet another embodiment, the wrist may be advantageously used, particularly where a pulse rate is typically monitored. Since the pulse may be easily felt on the wrist, there is underlying the region a distinct blood flow. Other embodiments may use other parts of the body, such as the ear lobes, the tongue, the inner lip, the nails, the eye, or the teeth. Some of these embodiments will be further described below. The ear lobes or the tip of the tongue may be advantageous because they are thinner skin regions, thus permitting transmission rather than diffuse reflection. However, the interference from the skin is still a problem in these embodiments. Other regions such as the inner lip or the bottom of the tongue may be contemplated because distinct veins are observable, but still the interference from the skin may be problematic in these embodiments. The eye may seem as a viable alternative because it is more transparent than skin. However, there are still issues with scattering in the eye. For example, the anterior chamber of the eye (the space between the cornea and the iris) comprises a fluid known as aqueous humor. However, the glucose level in the eye chamber may have a significant temporal lag on changes in the glucose level compared to the blood glucose level.

Figure 13:
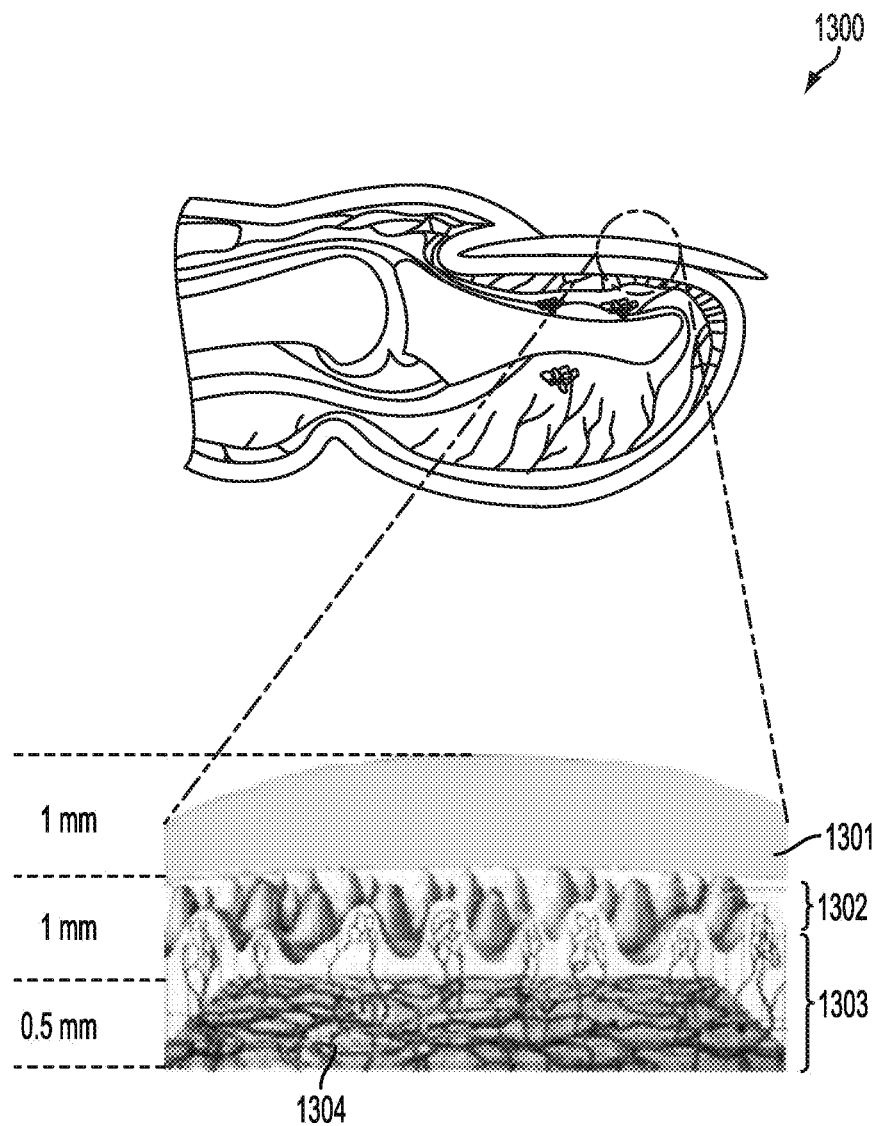
FIG. 13 illustrates a typical human nail tissue structure and the capillary vessels below it.

Because of the complexity of the interference from skin in non-invasive glucose monitoring (e.g., FIG. 10), other parts of the body without skin above blood vessels or capillaries may be alternative candidates for measuring blood constituents. One embodiment may involve transmission or reflection through human nails. As an example, FIG. 13 illustrates a typical human nail tissue structure 1300 and the capillary vessels below it. The fingernail 1301 is approximately 1 mm thick, and below this resides a layer of epidermis 1302 with a thickness of approximately 1 mm. The dermis 1304 is also shown, and within particularly the top about 0.5 mm of dermis are a significant number of capillary vessels. To measure the blood constituents, the light exposed on the top of the fingernail must penetrate about 2-2.5 mm or more, and the reflected light (round trip passage) should be sufficiently strong to measure. In one embodiment, the distance required to penetrate could be reduced by drilling a hole in the fingernail 1301.

Figure 14:
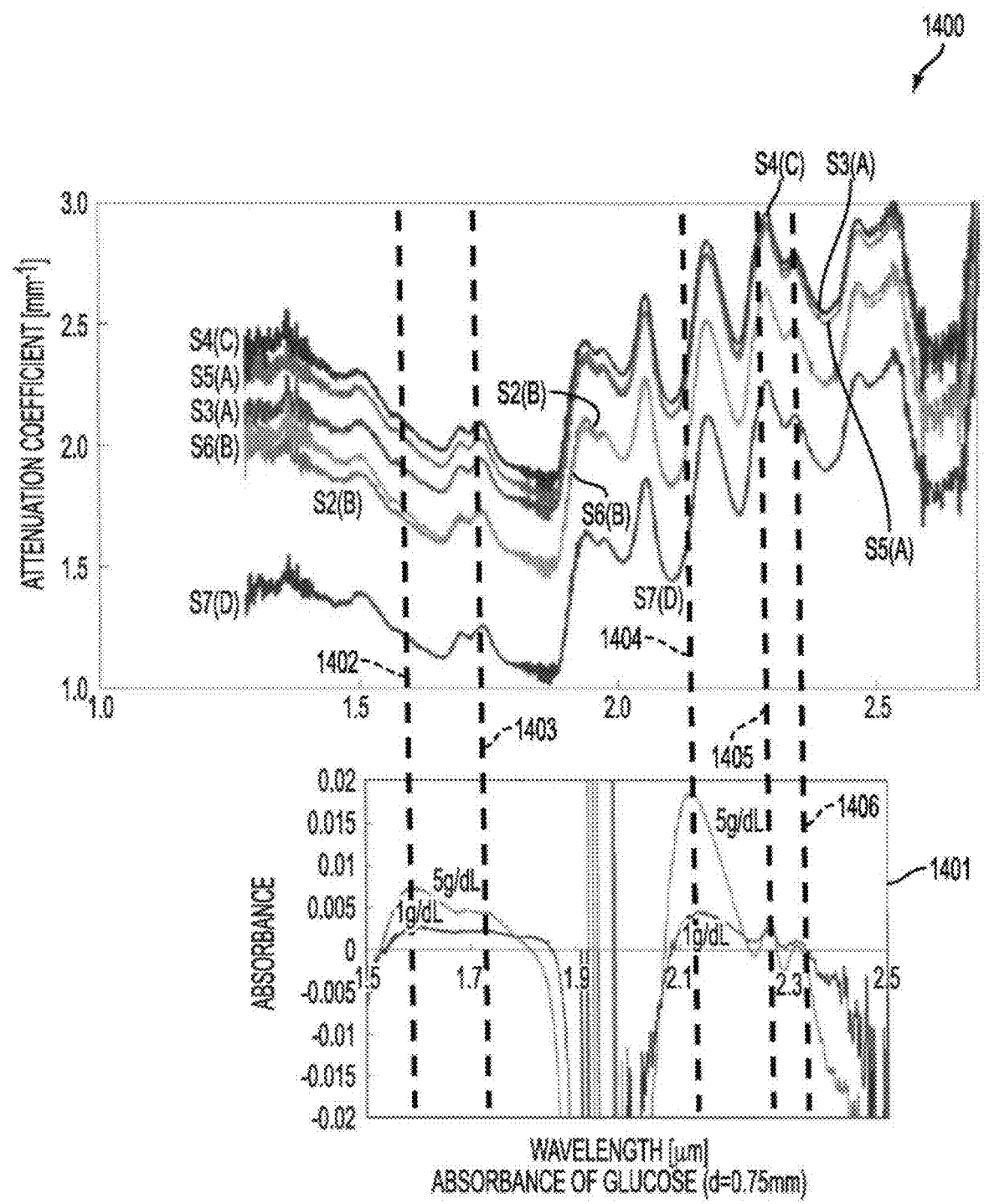
FIG. 14 shows the attenuation coefficient for seven nail samples that are allowed to stand in an environment with a humidity level of 14%. These coefficients are measured using an FTIR spectrometer over the near-infrared wavelength range of approximately 1 to 2.5 microns. Below is also included the spectrum of glucose.

In this alternative embodiment using the fingernail, there may still be interference from the nail's spectral features. For example, FIG. 14 illustrates the attenuation coefficient 1400 for seven nail samples that are allowed to stand in an environment with a humidity level of 14%. These coefficients are measured using an FTIR spectrometer over the near-infrared wavelength range of approximately 1 to 2.5 microns. These spectra are believed to correspond to the spectra of keratin contained in the nail plate. The base lines for the different samples are believed to differ because of the influence of scattering. Several of the absorption peaks observed correspond to peaks of keratin absorption, while other features may appear from the underlying epidermis and dermis. It should also be noted that the attenuation coefficients 1400 also vary considerably depending on humidity level or water content as well as temperature and other environmental factors. Moreover, the attenuation coefficient may also change in the presence of nail polish of various sorts.

Similar to skin, the large variations in attenuation coefficient for fingernails also may interfere with the absorption peaks of glucose. As an example, in FIG. 14 below the fingernail spectrum is also shown the glucose spectrum 1401 for two different glucose concentrations. The vertical lines 1402, 1403, 1404, 1405 and 1406 are drawn to illustrate the glucose absorption peaks and where they lie on the fingernail spectra 1400. As is apparent, the nail has interfering features that may be similar to skin, particularly since both have spectra that vary not only in wavelength but also with environmental factors. In one embodiment, it may be possible to see the glucose peaks 1402 and 1404 through the fingernail, but it may be much more difficult to observe the glucose peaks near 1403, 1405 and 1406.

Transmission or Reflection Through Teeth

Figure 15:
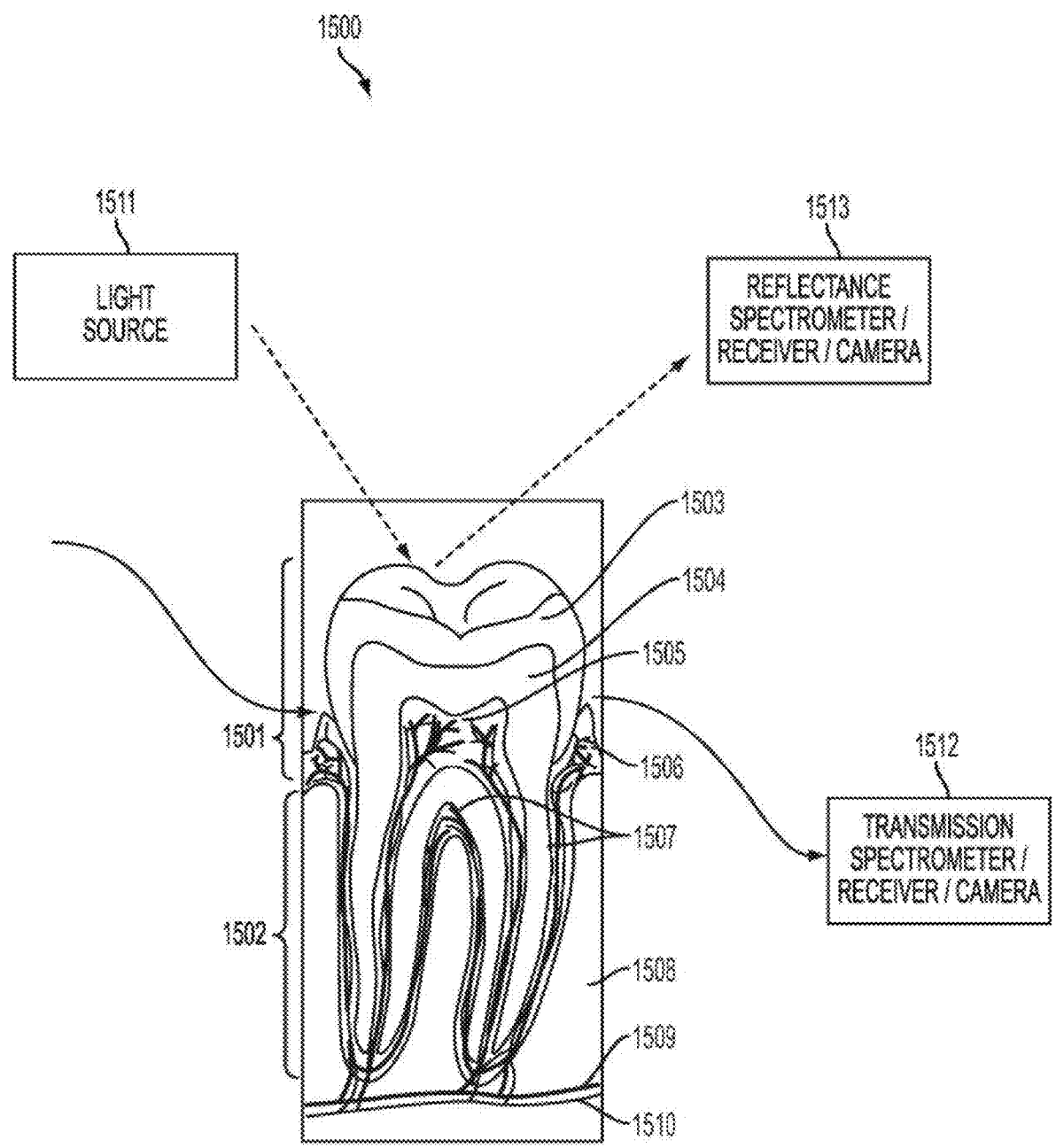
FIG. 15 illustrates the structure of a tooth.

Yet another embodiment may observe the transmittance or reflectance through teeth to measure blood constituents or analytes. FIG. 15 illustrates an exemplary structure of a tooth 1500. The tooth 1500 has a top layer called the crown 1501 and below that a root 1502 that reaches well into the gum 1506 and bone 1508 of the mouth. The exterior of the crown 1501 is an enamel layer 1503, and below the enamel is a layer of dentine 1504 that sits atop a layer of cementum 1507. Below the dentine 1504 is a pulp region 1505, which comprises within it blood vessels 1509 and nerves 1510. If the light can penetrate the enamel 1503 and dentine 1504, then the blood flow and blood constituents can be measured through the blood vessels in the dental pulp 1505. While it may be true that the amount of blood flow in the dental pulp 1505 may be less since it comprises capillaries, the smaller blood flow could still be advantageous if there is less interfering spectral features from the tooth.

Figure 16A:
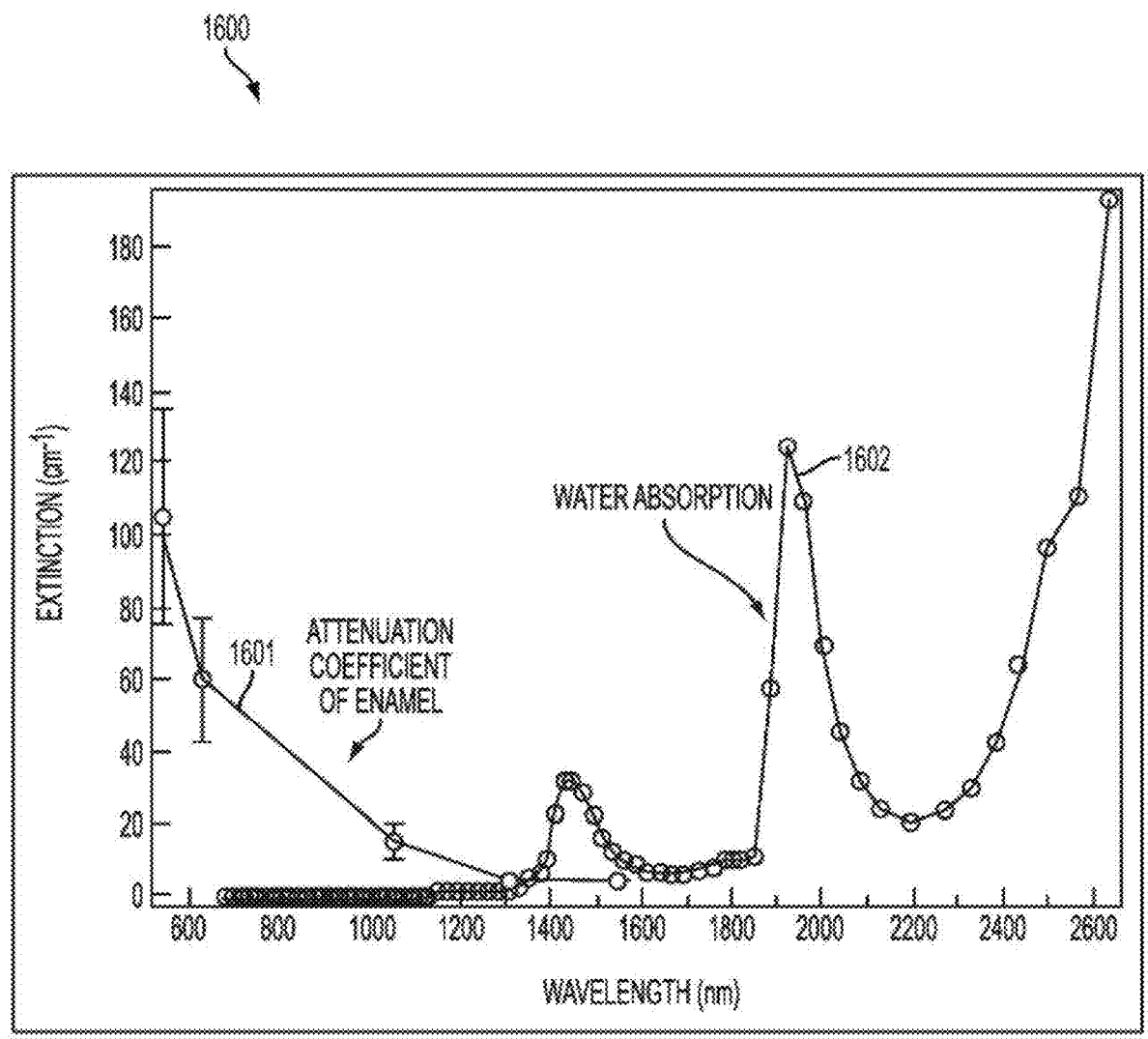
FIG. 16A shows the attenuation coefficient for dental enamel and water versus wavelength from approximately 600 nm to 2600 nm.

The transmission, absorption and reflection from teeth has been studied in the near infrared, and, although there are some features, the enamel and dentine appear to be fairly transparent in the near infrared (particularly wavelengths between 1500 and 2500 nm). For example, the absorption or extinction ratio for light transmission has been studied. FIG. 16A illustrates the attenuation coefficient 1600 for dental enamel 1601 (filled circles) and the absorption coefficient of water 1602 (open circles) versus wavelength. Near-infrared light may penetrate much further without scattering through all the tooth enamel, due to the reduced scattering coefficient in normal enamel. Scattering in enamel may be fairly strong in the visible, but decreases as approximately 1/wavelength$^3$ (i.e., inverse of the wavelength cubed) with increasing wavelength to a value of only 2-3 cm$^{-1}$ at 1310 nm and 1550 nm in the near infrared. Therefore, enamel may be virtually transparent in the near infrared with optical attenuation 1-2 orders of magnitude less than in the visible range.

Figure 16B:
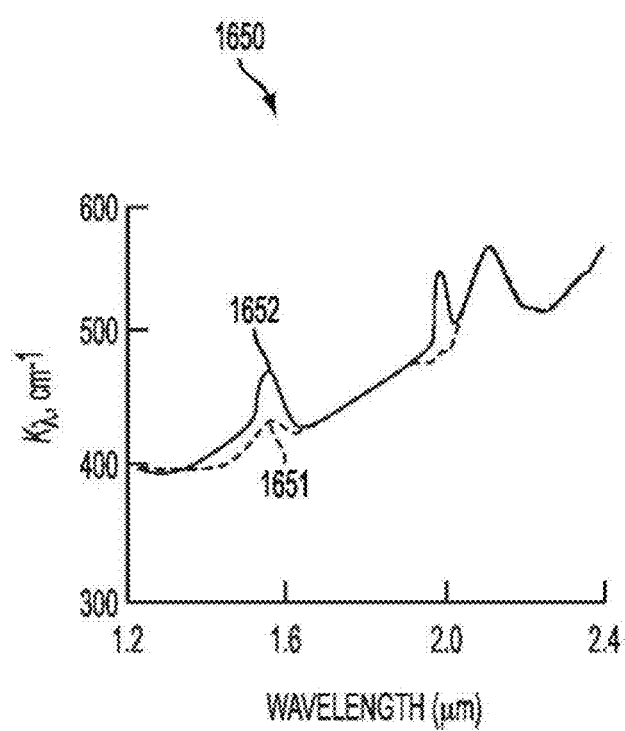
FIG. 16B illustrates the absorption spectrum of intact enamel and dentine in the wavelength range of approximately 1.2 to 2.4 microns.

As another example, FIG. 16B illustrates the absorption spectrum 1650 of intact enamel 1651 (dashed line) and dentine 1652 (solid line) in the wavelength range of approximately 1.2 to 2.4 microns. In the near infrared there are two absorption bands around 1.5 and 2 microns. The band with a peak around 1.57 microns may be attributed to the overtone of valent vibration of water present in both enamel and dentine. In this band, the absorption is greater for dentine than for enamel, which may be related to the large water content in this tissue. In the region of 2 microns, dentine may have two absorption bands, and enamel one. The band with a maximum near 2.1 microns may belong to the overtone of vibration of PO hydroxyapatite groups, which is the main substance of both enamel and dentine. Moreover, the band with a peak near 1.96 microns in dentine may correspond to water absorption (dentine may contain substantially higher water than enamel).

In addition to the absorption coefficient, the reflectance from intact teeth and teeth with dental caries (e.g., cavities) has been studied. In one embodiment, FIG. 17 shows the near infrared spectral reflectance 1700 over the wavelength range of approximately 800 nm to 2500 nm from an occlusal (e.g., top/bottom) tooth surface 1704. The curve with black diamonds 1701 corresponds to the reflectance from a sound, intact tooth section. The curve with asterisks * 1702 corresponds to a tooth section with an enamel lesion. The curve with circles 1703 corresponds to a tooth section with a dentine lesion. Thus, when there is a lesion, more scattering occurs and there may be an increase in the reflected light.

For wavelengths shorter than approximately 1400 nm, the shapes of the spectra remain similar, but the amplitude of the reflection changes with lesions. Between approximately 1400 nm and 2500 nm, an intact tooth 1701 has low reflectance (e.g., high transmission), and the reflectance appears to be more or less independent of wavelength. On the other hand, in the presence of lesions 1702 and 1703, there is increased scattering, and the scattering loss may be wavelength dependent. For example, the scattering loss may decrease as 1/(wavelength)$^3$—so, the scattering loss decreases with longer wavelengths. When there is a lesion in the dentine 1703, more water can accumulate in the area, so there is also increased water absorption. For example, the dips near 1450 nm and 1900 nm correspond to water absorption, and the reflectance dips are particularly pronounced in the dentine lesion 1703. One other benefit of the absorption, transmission or reflectance in the near infrared may be that stains and non-calcified plaque are not visible in this wavelength range, enabling better discrimination of defects, cracks, and demineralized areas.

Compared with the interference from skin 1000 in FIG. 10 or fingernails 1400 in FIG. 14, the teeth appear to introduce much less interference for non-invasive monitoring of blood constituents. The few features in FIG. 16B or 17 may be calibrated out of the measurement. Also, using an intact tooth 1701 may further minimize any interfering signals. Furthermore, since the tooth comprises relatively hard tissue, higher power from the light sources in the near infrared may be used without damaging the tissue, such as with skin.

Human Interface for Measurement System

A number of different types of measurements may be used to sample the blood in the dental pulp. The basic feature of the measurements should be that the optical properties are measured as a function of wavelength at a plurality of wavelengths. As further described below, the light source may output a plurality of wavelengths, or a continuous spectrum over a range of wavelengths. In a preferred embodiment, the light source may cover some or all of the wavelength range between approximately 1400 nm and 2500 nm. The signal may be received at a receiver, which may also comprise a spectrometer or filters to discriminate between different wavelengths. The signal may also be received at a camera, which may also comprise filters or a spectrometer. In an alternate embodiment, the spectral discrimination using filters or a spectrometer may be placed after the light source rather than at the receiver. The receiver usually comprises one or more detectors (optical-to-electrical conversion element) and electrical circuitry. The receiver may also be coupled to analog to digital converters, particularly if the signal is to be fed to a digital device.

Referring to FIG. 15, one or more light sources 1511 may be used for illumination. In one embodiment, a transmission measurement may be performed by directing the light source output 1511 to the region near the interface between the gum 1506 and dentine 1504. In one embodiment, the light may be directed using a light guide or a fiber optic. The light may then propagate through the dental pulp 1505 to the other side, where the light may be incident on one or more detectors or another light guide to transport the signal to a spectrometer, receiver or camera 1512. In another embodiment, the light source may be directed to one or more locations near the interface between the gum 1506 and dentine 1504 (in one example, could be from the two sides of the tooth). The transmitted light may then be detected in the occlusal surface above the tooth using a spectrometer, receiver, or camera 1512. In yet another embodiment, a reflectance measurement may be conducted by directing the light source output 1511 to, for example, the occlusal surface of the tooth, and then detecting the reflectance at a spectrometer, receiver or camera 1513. Although a few embodiments for measuring the blood constituents through a tooth are described, other embodiments and techniques may also be used and are intended to be covered by this disclosure.

Figure 18A:
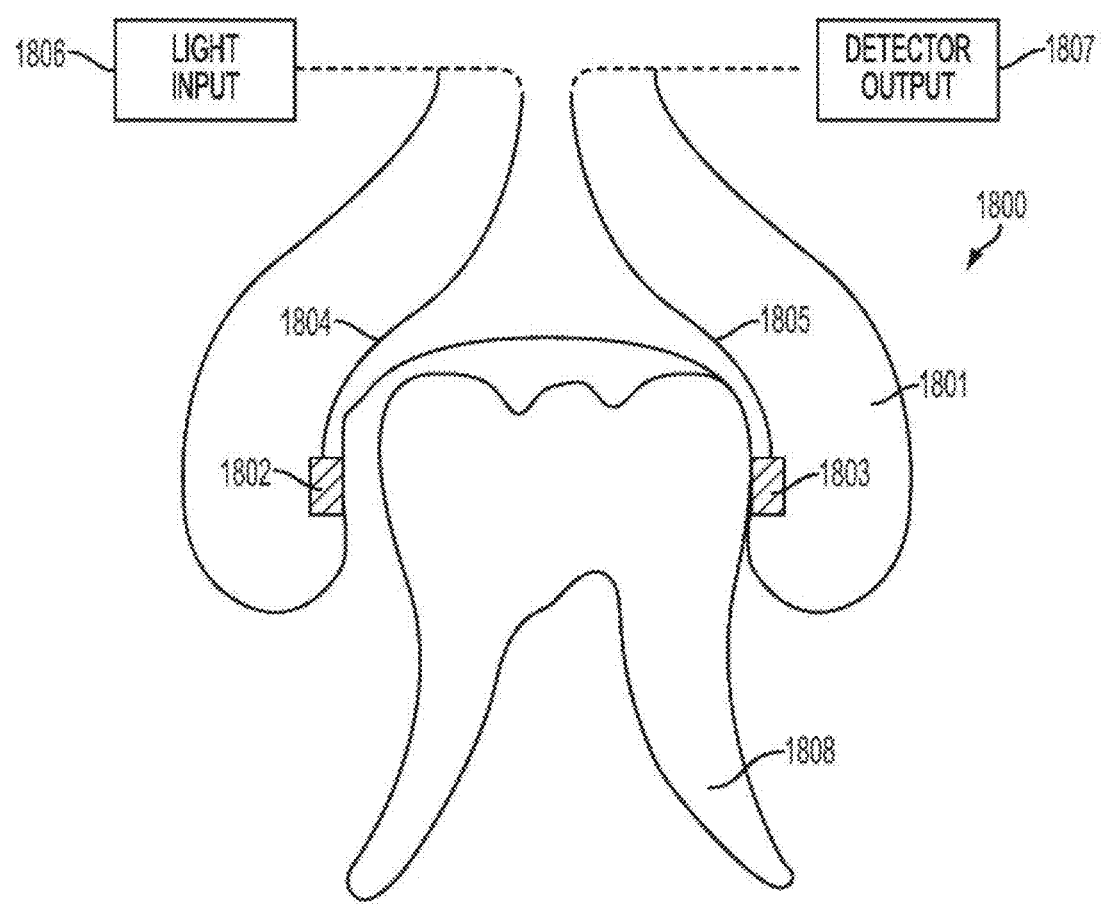
FIG. 18A illustrates a clamp design of a human interface to cap over one or more teeth and perform a non-invasive measurement of blood constituents.

The human interface for the non-invasive measurement of blood constituents may be of various forms. In one embodiment, a "clamp" design 1800 may be used cap over one or more teeth, as illustrated in FIG. 18A. The clamp design may be different for different types of teeth, or it may be flexible enough to fit over different types of teeth. For example, different types of teeth include the molars (toward the back of the mouth), the premolars, the canine, and the incisors (toward the front of the mouth). One embodiment of the clamp-type design is illustrated in FIG. 18A for a molar tooth 1808. The C-clamp 1801 may be made of a plastic or rubber material, and it may comprise a light source input 1802 and a detector output 1803 on the front or back of the tooth.

The light source input 1802 may comprise a light source directly, or it may have light guided to it from an external light source. Also, the light source input 1802 may comprise a lens system to collimate or focus the light across the tooth. The detector output 1803 may comprise a detector directly, or it may have a light guide to transport the signal to an external detector element. The light source input 1802 may be coupled electrically or optically through 1804 to a light input 1806. For example, if the light source is external in 1806, then the coupling element 1804 may be a light guide, such as a fiber optic. Alternately, if the light source is contained in 1802, then the coupling element 1804 may be electrical wires connecting to a power supply in 1806. Similarly, the detector output 1803 may be coupled to a detector output unit 1807 with a coupling element 1805, which may be one or more electrical wires or a light guide, such as a fiber optic. This is just one example of a clamp over one or more teeth, but other embodiments may also be used and are intended to be covered by this disclosure.

Figure 18B:
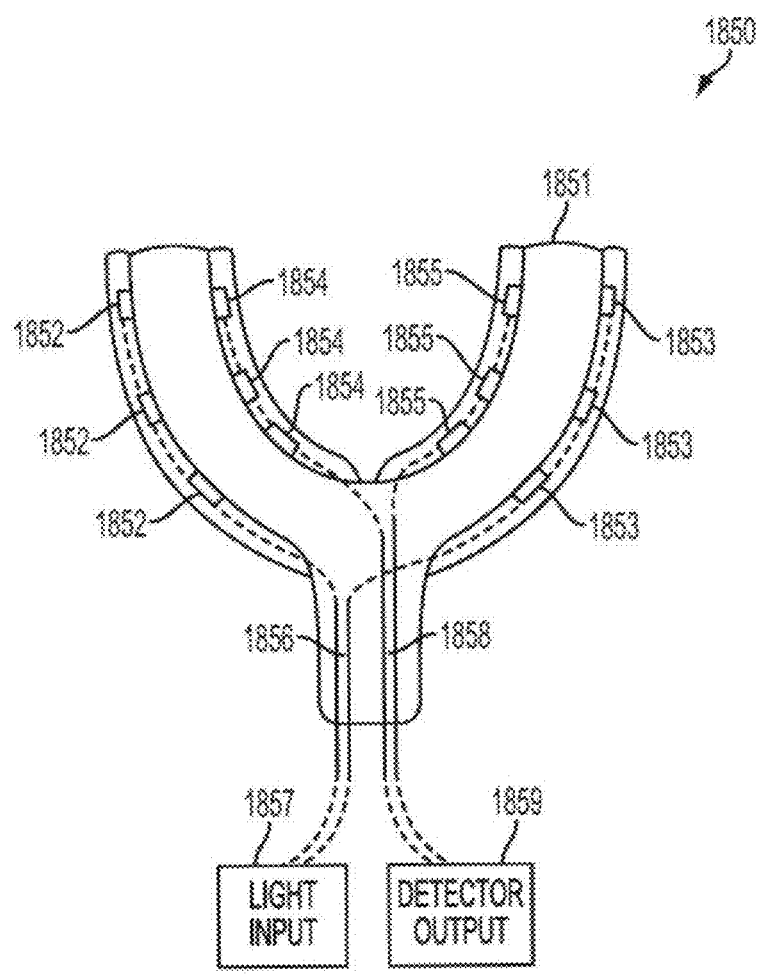
FIG. 18B shows a mouth guard design of a human interface to perform a non-invasive measurement of blood constituents.

In yet another embodiment, one or more light source ports and sensor ports may be used in a mouth-guard type design. For example, one embodiment of a dental mouth guard 1850 is illustrated in FIG. 18B. The structure of the mouth guard 1851 may be similar to mouth guards used in sports (e.g., when playing football or boxing) or in dental trays used for applying fluoride treatment, and the mouth guard may be made from plastic or rubber materials, for example. As an example, the mouth guard may have one or more light source input ports 1852, 1853 and one or more detector output ports 1854, 1855. Although six input and output ports are illustrated, any number of ports may be used.

Similar to the clamp design described above, the light source inputs 1852, 1853 may comprise one or more light sources directly, or they may have light guided to them from an external light source. Also, the light source inputs 1852, 1853 may comprise lens systems to collimate or focus the light across the teeth. The detector outputs 1854, 1855 may comprise one or more detectors directly, or they may have one or more light guides to transport the signals to an external detector element. The light source inputs 1852, 1853 may be coupled electrically or optically through 1856 to a light input 1857. For example, if the light source is external in 1857, then the one or more coupling elements 1856 may be one or more light guides, such as a fiber optic. Alternately, if the light sources are contained in 1852, 1853, then the coupling element 1856 may be one or more electrical wires connecting to a power supply in 1857. Similarly, the detector outputs 1854, 1855 may be coupled to a detector output unit 1859 with one or more coupling elements 1858, which may be one or more electrical wires or one or more light guides, such as a fiber optic. This is just one example of a mouth guard design covering a plurality of teeth, but other embodiments may also be used and are intended to be covered by this disclosure. For instance, the position of the light source inputs and detector output ports could be exchanged, or some mixture of locations of light source inputs and detector output ports could be used.

Also, if reflectance from the teeth is to be measured, then the light sources and detectors may be on the same side of the tooth. Moreover, it may be advantageous to pulse the light source with a particular pulse width and pulse repetition rate, and then the detection system can measure the pulsed light returned from or transmitted through the tooth. Using a lock-in type technique (e.g., detecting at the same frequency as the pulsed light source and also possibly phase locked to the same signal), the detection system may be able to reject background or spurious signals and increase the signal-to-noise ratio of the measurement.

Other elements may be added to the human interface designs of FIG. 18 and are also intended to be covered by this disclosure. For instance, in one embodiment it may be desirable to have replaceable inserts that may be disposable. Particularly in a doctor's office or hospital setting, the same instrument may be used with a plurality of patients. Rather than disinfecting the human interface after each use, it may be preferable to have disposable inserts that can be thrown away after each use. In one embodiment, a thin plastic coating material may enclose the clamp design of FIG. 18A or mouth guard design of FIG. 18B. The coating material may be inserted before each use, and then after the measurement is exercised the coating material may be peeled off and replaced. Such a design may save the physician or user considerable time, while at the same time provide the business venture with a recurring cost revenue source. Any coating material or other disposable device may be constructed of a material having suitable optical properties that may be considered during processing of the signals used to detect any anomalies in the teeth.

Light Sources for Near Infrared

In general, the near-infrared (NIR) region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye-safe" window, which corresponds to wavelengths longer than about 1400 nm. While the SWIR is used for illustrative purposes, it should be clear that the discussion that follows could also apply to using the NIR wavelength range, or other wavelength bands. There are a number of light sources that may be used in the near infrared. To be more specific, the discussion below will consider light sources operating in the so-called short wave infrared (SWIR), which may cover the wavelength range of approximately 1400 nm to 2500 nm. Other wavelength ranges may also be used for the applications described in this disclosure, so the discussion below is merely provided for exemplary types of light sources. The SWIR wavelength range may be valuable for a number of reasons. First, the SWIR corresponds to a transmission window through water and the atmosphere. For example, 302 in FIG. 3A and 1602 in FIG. 16A illustrate the water transmission windows. Also, through the atmosphere, wavelengths in the SWIR have similar transmission windows due to water vapor in the atmosphere. Second, the so-called "eye-safe" wavelengths are wavelengths longer than approximately 1400 nm. Third, the SWIR covers the wavelength range for nonlinear combinations of stretching and bending modes as well as the first overtone of C—H stretching modes. Thus, for example, glucose and ketones among other substances may have unique signatures in the SWIR. Moreover, many solids have distinct spectral signatures in the SWIR, so particular solids may be identified using stand-off detection or remote sensing. For instance, many explosives have unique signatures in the SWIR.

Infrared light sources can be used for diagnostics and therapeutics in a number of medical applications. For example, broadband light sources can advantageously be used for diagnostics, while narrower band light sources can advantageously be used for therapeutics. In one embodiment, selective absorption or damage can be achieved by choosing the laser wavelength to lie approximately at an absorption peak of particular tissue types. Also, by using infrared wavelengths that minimize water absorption peaks and longer wavelengths that have lower tissue scattering, larger penetration depths into the biological tissue can be obtained. In this disclosure, infrared wavelengths include wavelengths in the range of approximately 0.9 microns to 10 microns, with wavelengths between about 0.98 microns and 2.5 microns more suitable for certain applications.

Different light sources may be selected for the SWIR based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum sources (SC) may be advantageously used. Also, different fibers may be used for transporting the light, such as fused silica fibers, plastic fibers, mid-infrared fibers (e.g., tellurite, chalcogenides, fluorides, ZBLAN, etc), or a hybrid of these fibers.

Lamps may be used if low power or intensity of light is required in the SWIR, and if an incoherent beam is suitable. In one embodiment, in the SWIR an incandescent lamp that can be used is based on tungsten and halogen, which have an emission wavelength between approximately 500 nm to 2500 nm. For low intensity applications, it may also be possible to use thermal sources, where the SWIR radiation is based on the black body radiation from the hot object. Although the thermal and lamp based sources are broadband and have low intensity fluctuations, it may be difficult to achieve a high signal-to-noise ratio in a non-invasive blood constituent measurement due to the low power levels. Also, the lamp based sources tend to be energy inefficient.

In another embodiment, LED's can be used that have a higher power level in the SWIR wavelength range. LED's also produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in different wavelength bands, some of which could preferably overlap in spectrum. One advantage of LEDs as well as other solid state components is the compact size that they may be packaged into.

In yet another embodiment, various types of laser diodes may be used in the SWIR wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB) LDs, distributed Bragg reflector (DBR) LDs. Since the LDs have relatively narrow wavelength range (typically under 10 nm), in one embodiment a plurality of LDs may be used that are at different wavelengths in the SWIR. For example, in a preferred embodiment for non-invasive glucose monitoring, it may be advantageous to use LDs having emission spectra near some or all of the glucose spectral peaks (e.g., near 1587 nm, 1750 nm, 2120 nm, 2270 nm, and 2320 nm). The various LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures, such as distributed Bragg reflector LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 to 100 nm wide, preferably in the 60 to 100 nm range. Although currently SLDs are commercially available in the wavelength range of approximately 400 nm to 1700 nm, SLDs could and may in the future be made to cover a broader region of the SWIR.

Figure 19:
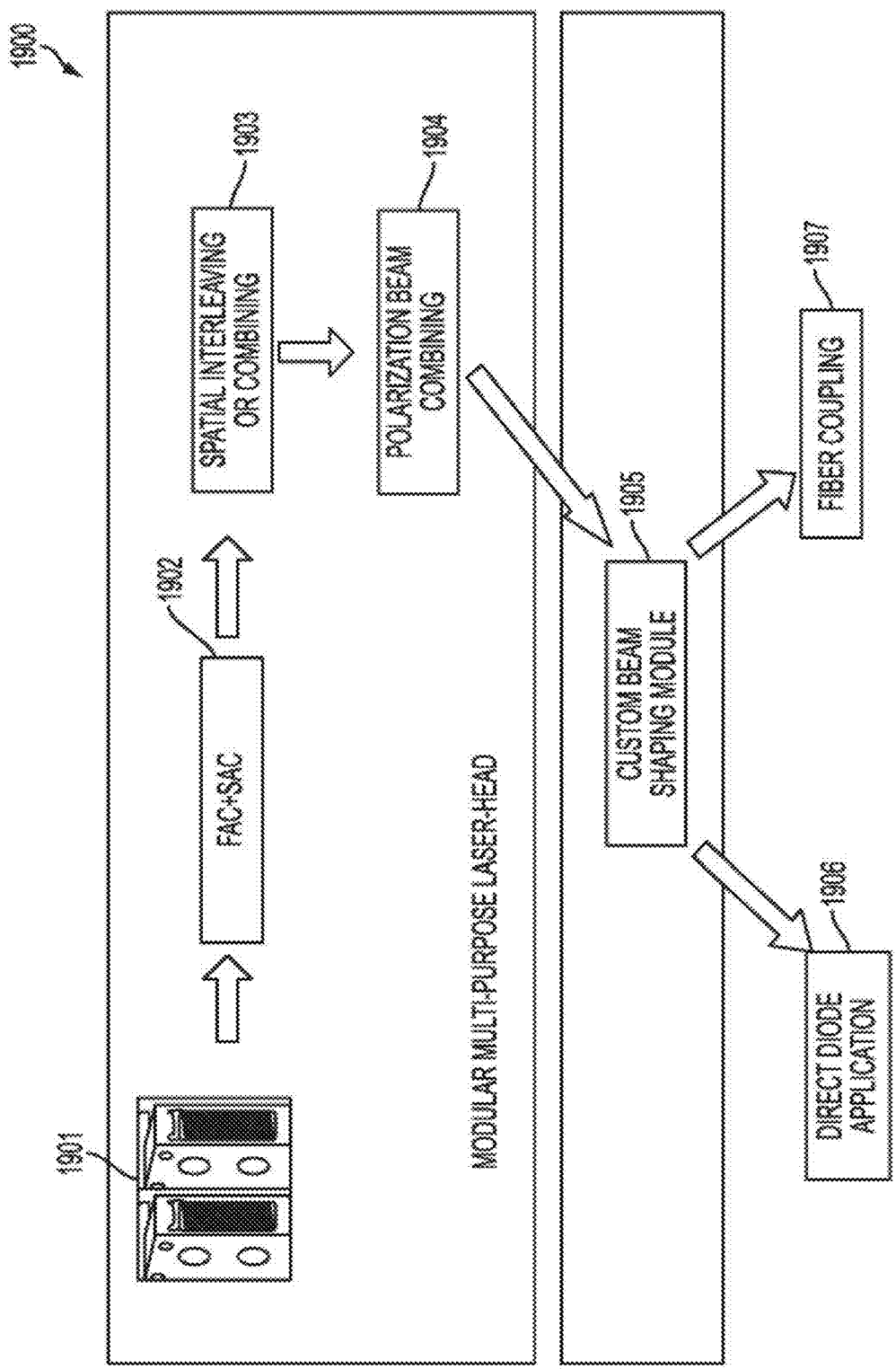
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. As an example, FIG. 19 shows an example of the block diagram 1900 or building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

Then, the brightness may be increased by spatially combining the beams from multiple stacks 1903. The combiner may include spatial interleaving, it may include wavelength multiplexing, or it may involve a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In one embodiment, the output may then be focused or coupled into a large diameter core fiber. As an example, typical dimensions for the large diameter core fiber range from approximately 100 microns in diameter to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or additional elements may also be used.

SWIR Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until now, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

Figure 20:
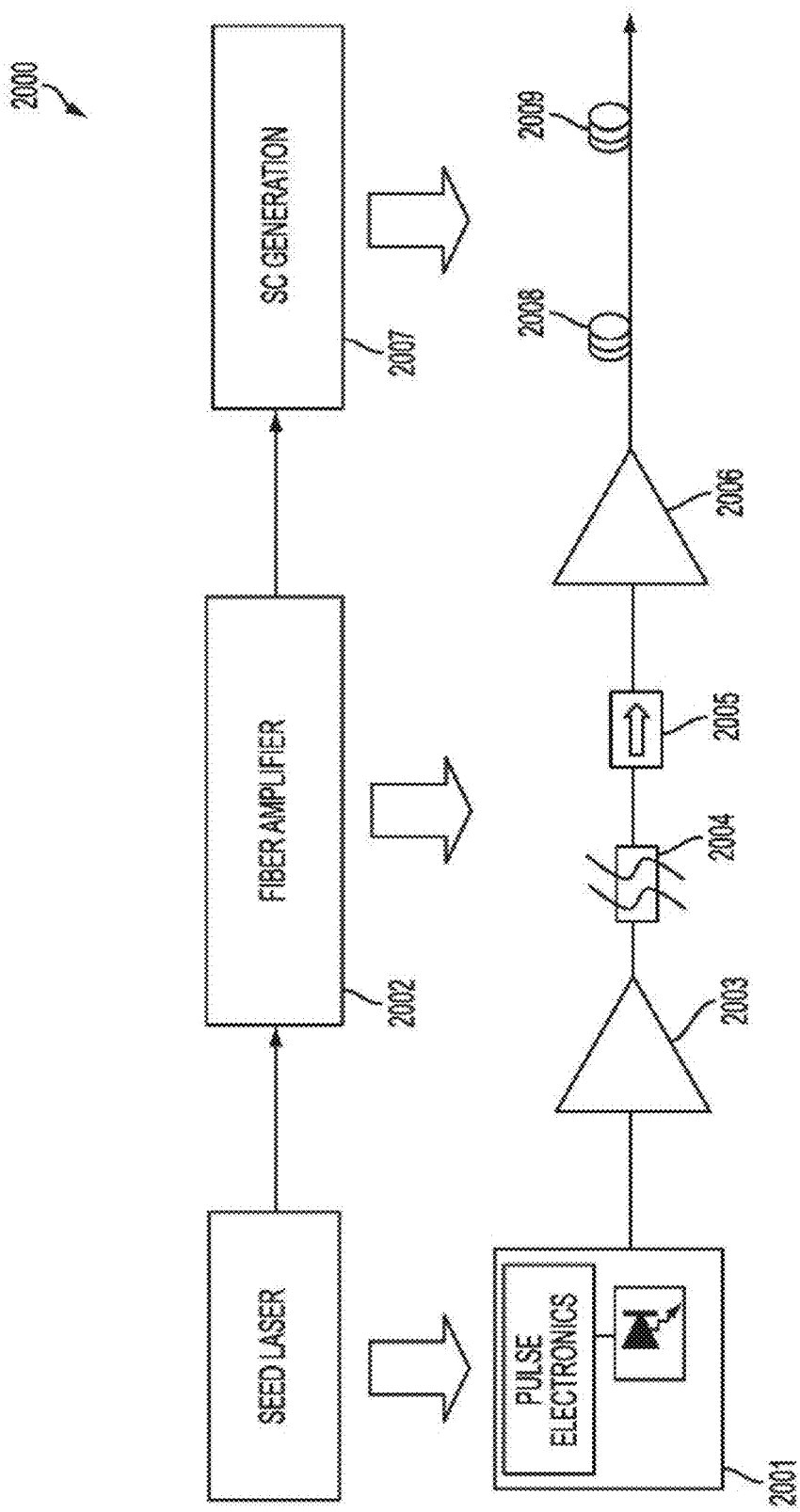
FIG. 20 shows a platform architecture for different wavelength ranges for an all-fiber-integrated, high powered, super-continuum light source.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback laser diode with a wavelength near 1542 or 1550 nm, with approximately 0.5-2.0 ns pulsed output, and with a pulse repetition rate between a kilohertz to about 100 MHz or more. The output from the seed laser diode may then be amplified in a multiple-stage fiber amplifier 2002 comprising one or more gain fiber segments. In one embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. In one exemplary embodiment, the SC fiber length may range from a few millimeters to 100 m or more. In one embodiment, the SC generation may occur in a first fiber 2008 where the modulational-instability initiated pulse break-up primarily occurs, followed by a second fiber 2009 where the SC generation and spectral broadening primarily occurs.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime—often called the soliton regime. For high peak powers in the dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 µm), mid-IR fibers such as fluorides, chalcogenides, or tellurites (for generating SC out to 4.5 µm or longer), photonic crystal fibers (for generating SC between 0.4 and 1.7 µm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

Figure 21:
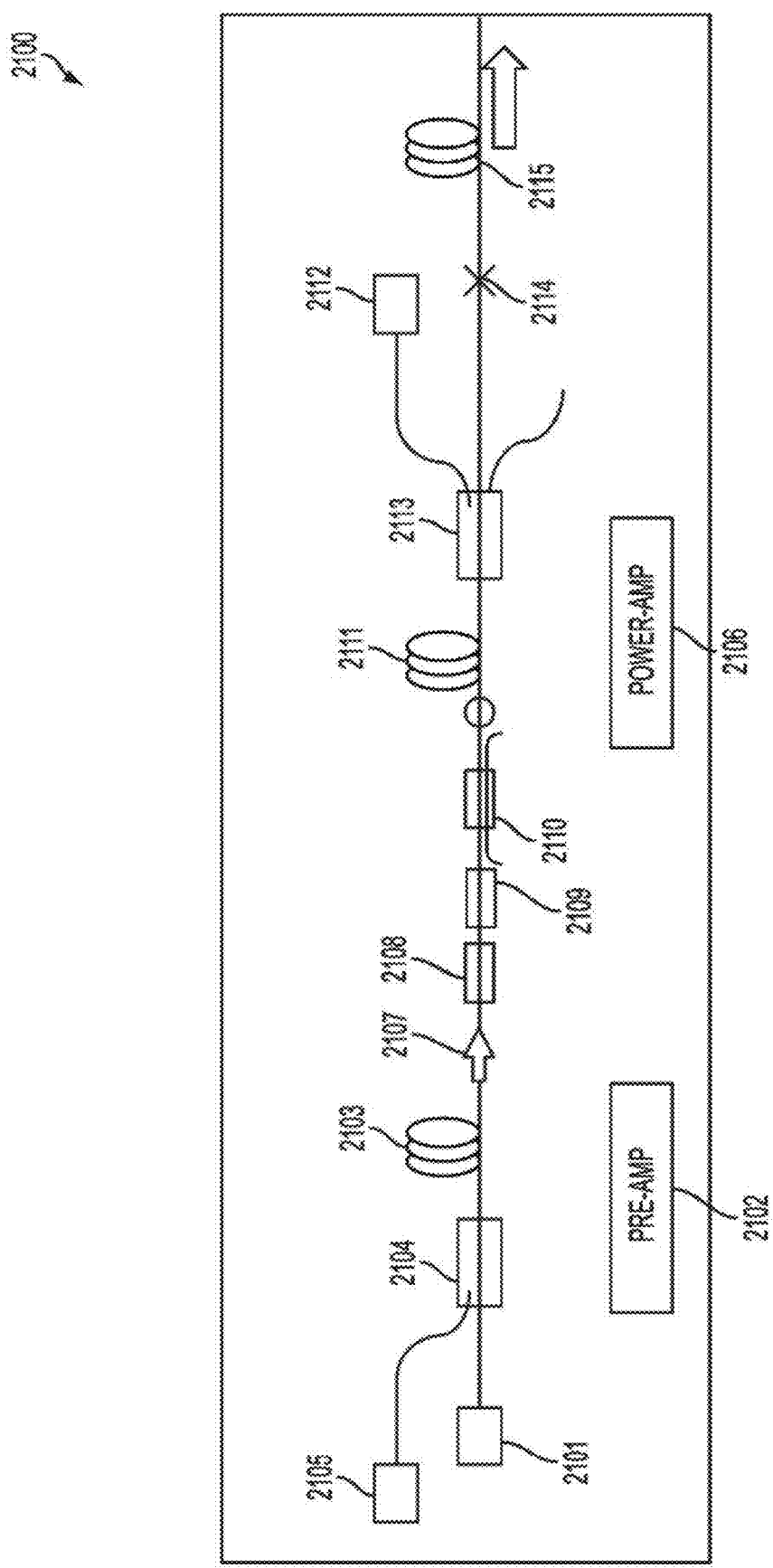
FIG. 21 illustrates one embodiment of a short-wave infrared (SWIR) super-continuum (SC) light source.

One example of an SC laser that operates in the SWIR used in one embodiment is illustrated in FIG. 21. This SWIR SC source 2100 produces an output of up to approximately 5 W over a spectral range of about 1.5 to 2.4 microns, and this particular laser is made out of polarization maintaining components. The seed laser 2101 is a distributed feedback (DFB) laser operating near 1542 nm producing approximately 0.5 nanosecond (ns) pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W 940 nm laser diode 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses a 4 m length of the 12/130 micron erbium/ytterbium doped fiber 2111 that is counter-propagating pumped using one or more 30 W 940 nm laser diodes 2112 coupled in through a combiner 2113. An approximately 1-2 meter length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
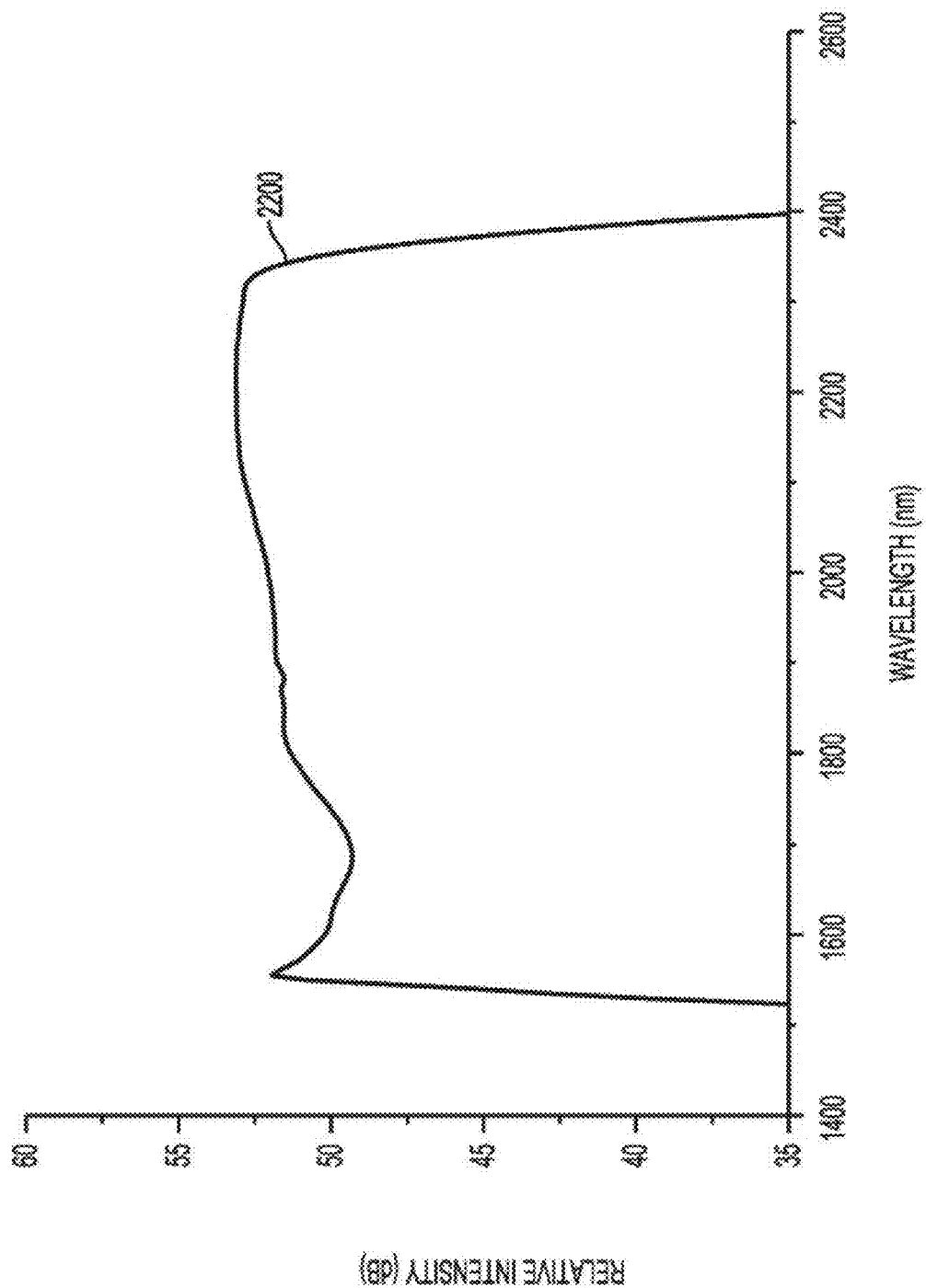
FIG. 22 shows the output spectrum from the SWIR SC laser of FIG. 21 when about 10 m length of fiber for SC generation is used. This fiber is a single-mode, non-dispersion shifted fiber that is optimized for operation near 1550 nm.

If an output fiber of about 10 m in length is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to ~2500 nm).

Also, if extra-dry fibers are used with less O—H content, then the wavelength edge may also reach to a longer wavelength. To generate more spectrum toward the shorter wavelengths, the pump wavelength (in this case .about.1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC has been described, different components, different fibers, and different configurations may also be used consistent with this disclosure. For instance, another embodiment of the similar configuration 2100 in FIG. 21 may be used to generate high powered SC between approximately 1060 and 1800 nm. For this embodiment, the seed laser 2101 may be a 1064 nm distributed feedback (DFB) laser diode, the pre-amplifier gain fiber 2103 may be a ytterbium-doped fiber amplifier with 10/125 microns dimensions, and the pump laser 2105 may be a 10 W 915 nm laser diode. In the mid-stage, a mode field adapter may be included in addition to the isolator 2107, band pass filter 2108, polarizer 2109 and tap 2110. The gain fiber 2111 in the power amplifier may be a 20 m length of ytterbium-doped fiber with 25/400 microns dimension for example. The pump 2112 for the power amplifier may be up to six pump diodes providing 30 W each near 915 nm, for example. For this much pump power, the output power in the SC may be as high as 50 W or more.

In another embodiment, it may be desirous to generate high power SWIR SC over 1.4-1.8 microns and separately 2-2.5 microns (the window between 1.8 and 2 microns may be less important due to the strong water and atmospheric absorption). For example, the top SC source of FIG. 23 can lead to bandwidths ranging from about 1400 nm to 1800 nm or broader, while the lower SC source of FIG. 23 can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber SMF, high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

Figure 23:
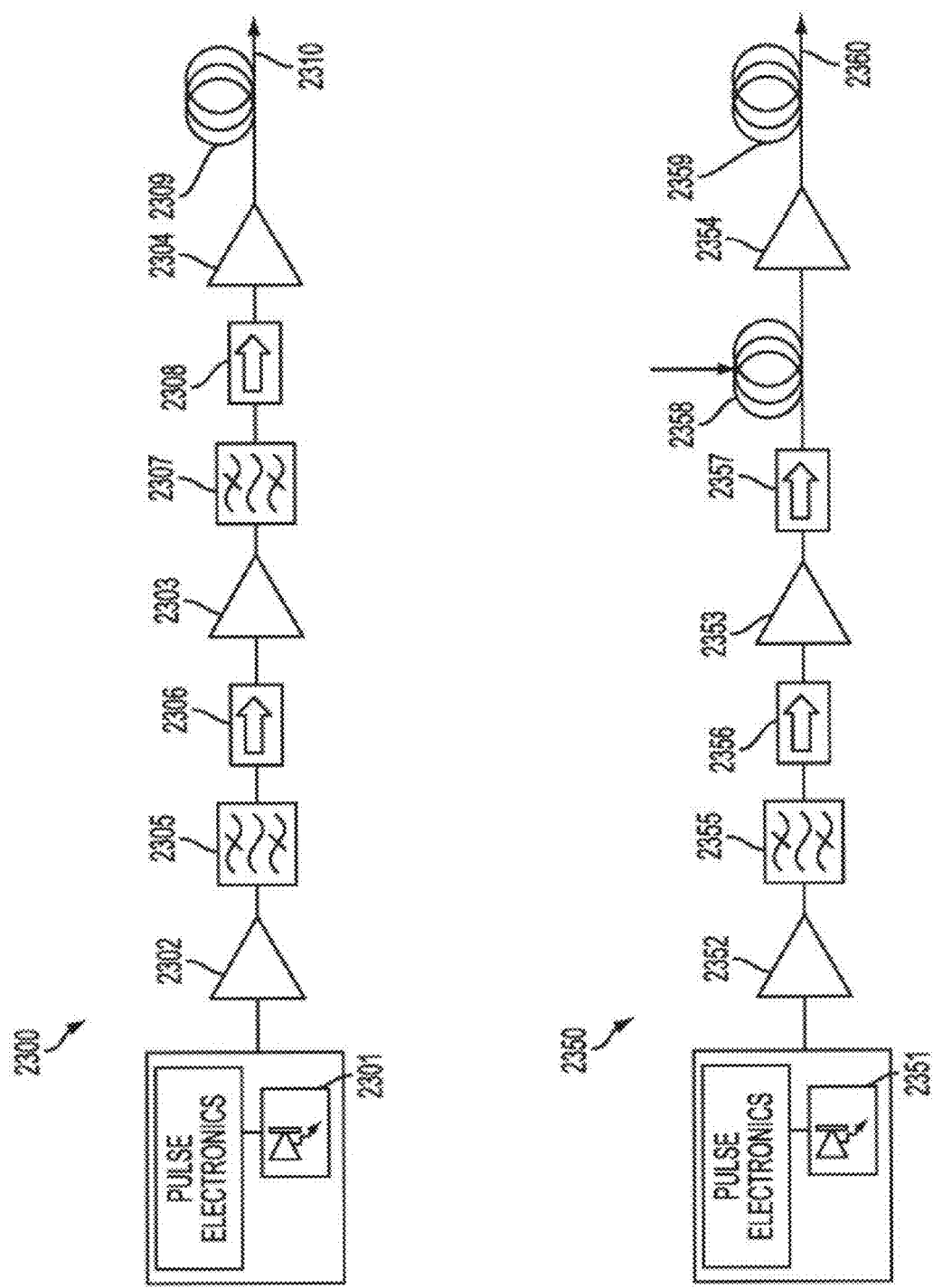
FIG. 23 illustrates high power SWIR-SC lasers that may generate light between approximately 1.4-1.8 microns (top) or approximately 2-2.5 microns (bottom).
Figure 24:
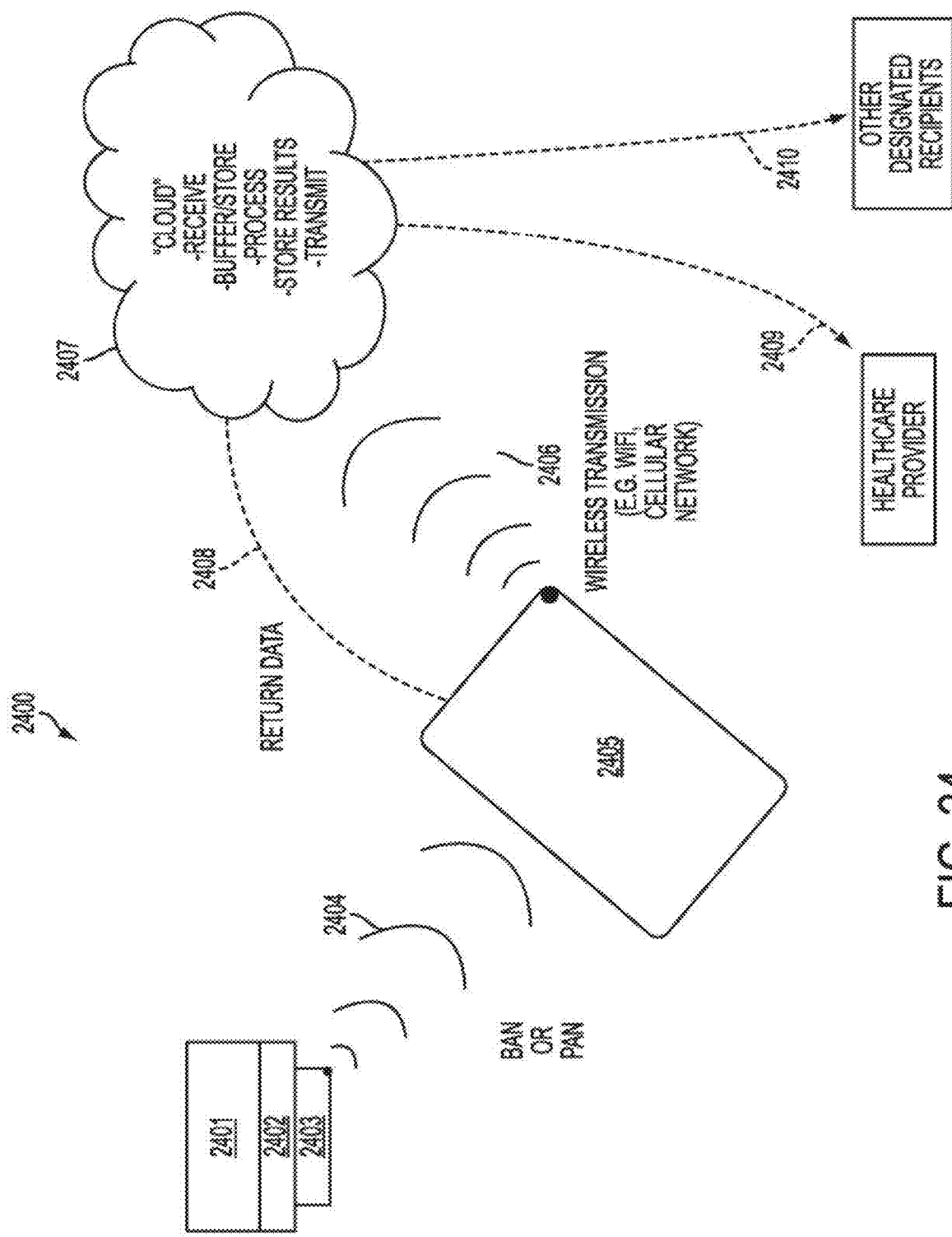
FIG. 24 schematically shows that the medical measurement device can be part of a personal or body area network that communicates with another device (e.g., smart phone or tablet) that communicates with the cloud. The cloud may in turn communicate information with the user, healthcare providers, or other designated recipients.

In one embodiment, the top of FIG. 23 illustrates a block diagram for an SC source 2300 capable of generating light between approximately 1400 and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, the bottom of FIG. 23 illustrates a block diagram for an SC source 2350 capable of generating light between approximately 1900 and 2500 nm or broader. As an example, the seed laser diode 2351 can comprise a DFB or DBR laser that generates, for example, several milliwatts of power around 1542 or 1553 nm. The fiber pre-amplifier 2352 can comprise an erbium-doped fiber amplifier or an erbium/ytterbium doped double-clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1550 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have a length between approximately 5 and 50 meters, for example. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20-23 are that they may use all-fiber components, so that the SC laser can be all-fiber, monolithically integrated with no moving parts. The all-integrated configuration can consequently be robust and reliable.

FIGS. 20-23 are examples of SC light sources that may be advantageously used for SWIR light generation in various medical diagnostic and therapeutic applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers. Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In an alternate embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate SWIR light that are intended to be covered by this disclosure.

Wireless Link to the Cloud

The non-invasive blood constituent or analytes measurement device may also benefit from communicating the data output to the "cloud" (e.g., data servers and processors in the web remotely connected) via wired and/or wireless communication strategies. The non-invasive devices may be part of a series of biosensors applied to the patient, and collectively these devices form what might be called a body area network or a personal area network. The biosensors and non-invasive devices may communicate to a smart phone, tablet, personal data assistant, computer, and/or other microprocessor-based device, which may in turn wirelessly or over wire and/or fiber optically transmit some or all of the signal or processed data to the internet or cloud. The cloud or internet may in turn send the data to doctors or health care providers as well as the patients themselves. Thus, it may be possible to have a panoramic, high-definition, relatively comprehensive view of a patient that doctors can use to assess and manage disease, and that patients can use to help maintain their health and direct their own care.

In a particular embodiment 2400, the physiological measurement device or non-invasive blood constituent measurement device 2401 may comprise a transmitter 2403 to communicate over a first communication link 2404 in the body area network or personal area network to a receiver in a smart phone, tablet cell phone, PDA, or computer 2405. For the measurement device 2401, it may also be advantageous to have a processor 2402 to process some of the physiological data, since with processing the amount of data to transmit may be less (hence, more energy efficient). The first communication link 2404 may operate through the use of one of many wireless technologies such as Bluetooth, Zigbee, WiFi, IrDA (infrared data association), wireless USB, or Z-wave, to name a few. Alternatively, the communication link 2404 may occur in the wireless medical band between 2360 and 2390 MHz, which the FCC allocated for medical body area network devices, or in other designated medical device or WMTS bands. These are examples of devices that can be used in the body area network and surroundings, but other devices could also be used and are included in the scope of this disclosure.

The personal device 2405 may store, process, display, and transmit some of the data from the measurement device 2401. The device 2405 may comprise a receiver, transmitter, display, voice control and speakers, and one or more control buttons or knobs and a touch screen. Examples of the device 2405 include smart phones such as the Apple iPhones® or phones operating on the Android or Microsoft systems. In one embodiment, the device 2405 may have an application, software program, or firmware to receive and process the data from the measurement device 2401. The device 2405 may then transmit some or all of the data or the processed data over a second communication link 2406 to the internet or "cloud" 2407. The second communication link 2406 may advantageously comprise at least one segment of a wireless transmission link, which may operate using WiFi or the cellular network. The second communication link 2406 may additionally comprise lengths of fiber optic and/or communication over copper wires or cables.

The internet or cloud 2407 may add value to the measurement device 2401 by providing services that augment the physiological data collected. In a particular embodiment, some of the functions performed by the cloud include: (a) receive at least a fraction of the data from the device 2405; (b) buffer or store the data received; (c) process the data using software stored on the cloud; (d) store the resulting processed data; and (e) transmit some or all of the data either upon request or based on an alarm. As an example, the data or processed data may be transmitted 2408 back to the originator (e.g., patient or user), it may be transmitted 2409 to a health care provider or doctor, or it may be transmitted 2410 to other designated recipients.

The cloud 2407 may provide a number of value-add services. For example, the cloud application may store and process the physiological data for future reference or during a visit with the healthcare provider. If a patient has some sort of medical mishap or emergency, the physician can obtain the history of the physiological parameters over a specified period of time. In another embodiment, if the physiological parameters fall out of acceptable range, alarms may be delivered to the user 2408, the healthcare provider 2409, or other designated recipients 2410. These are just some of the features that may be offered, but many others may be possible and are intended to be covered by this disclosure. As an example, the device 2405 may also have a GPS sensor, so the cloud 2407 may be able to provide time, data and position along with the physiological parameters. Thus, if there is a medical emergency, the cloud 2407 could provide the location of the patient to the healthcare provider 2409 or other designated recipients 2410. Moreover, the digitized data in the cloud 2407 may help to move toward what is often called "personalized medicine." Based on the physiological parameter data history, medication or medical therapies may be prescribed that are customized to the particular patient.

Beyond the above benefits, the cloud application 2407 and application on the device 2405 may also have financial value for companies developing measurement devices 2401 such as a non-invasive blood constituent monitor. In the case of glucose monitors, the companies make the majority of their revenue on the measurement strips. However, with a non-invasive monitor, there is no need for strips, so there is less of an opportunity for recurring costs (e.g., the razor/razor blade model does not work for non-invasive devices). On the other hand, people may be willing to pay a periodic fee for the value-add services provided on the cloud 2407. Diabetic patients, for example, would probably be willing to pay a periodic fee for monitoring their glucose levels, storing the history of the glucose levels, and having alarm warnings when the glucose level falls out of range. Similarly, patients taking ketone bodies supplement for treatment of disorders characterized by impaired glucose metabolism (e.g., Alzheimer's, Parkinson's, Huntington's or ALS) may need to monitor their ketone bodies level. These patients would also probably be willing to pay a periodic fee for the value-add services provided on the cloud 2407. Thus, by leveraging the advances in wireless connectivity and the widespread use of handheld devices such as smart phones that can wirelessly connect to the cloud, businesses can build a recurring cost business model even using non-invasive measurement devices.

In addition, it may be advantageous to use pattern matching algorithms and other software and mathematical methods to identify the blood constituents of interest. In one embodiment, the spectrum may be correlated with a library of known spectra to determine the overlap integrals, and a threshold function may be used to quantify the concentration of different constituents. This is just one way to perform the signal processing, and many other techniques, algorithms, and software may be used and would fall within the scope of this disclosure.

Described herein are just some examples of the beneficial use of near-infrared or SWIR lasers for non-invasive monitoring of glucose, ketones, HbA1c and other blood constituents. However, many other medical procedures can use the near-infrared or SWIR light consistent with this disclosure and are intended to be covered by the disclosure.

Figure 25:
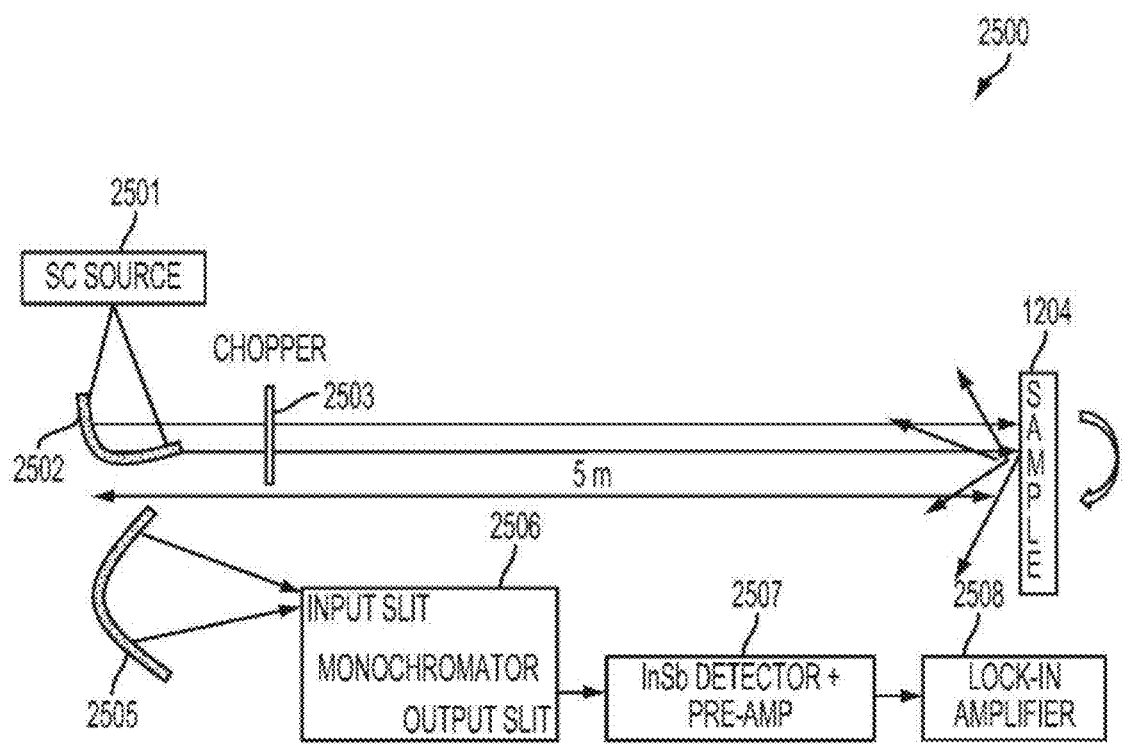
FIG. 25 shows the experimental set-up for a reflection-spectroscopy based stand-off detection system.

In another specific embodiment, experiments have been performed for stand-off detection of solid targets with diffuse reflection spectroscopy using a fiber-based super-continuum source (further described herein). In particular, the diffuse reflection spectrum of solid samples such as explosives (TNT, RDX, PETN), fertilizers (ammonium nitrate, urea), and paints (automotive and military grade) have been measured at stand-off distances of 5 m. Although the measurements were done at 5 m, calculations show that the distance could be anywhere from a few meters to over 150 m. These are specific samples that have been tested, but more generally other materials (particularly comprising hydro-carbons) could also be tested and identified using similar methods. The experimental set-up 2500 for the reflection-spectroscopy-based stand-off detection system is shown in FIG. 25, while details of the SC source 2501 are described in this disclosure in FIGS. 20, 21, and 23. First, the diverging SC output is collimated to a 1 cm diameter beam using a 25 mm focal length, 90 degrees off-axis, gold coated, parabolic mirror 2502. To reduce the effects of chromatic aberration, refractive optics are avoided in the setup. All focusing and collimation is done using metallic mirrors that have almost constant reflectivity and focal length over the entire SC output spectrum. The sample 2504 is kept at a distance of 5 m from the collimating mirror 2502, which corresponds to a total round trip path length of 10 m before reaching the collection optics 2505. A 12 cm diameter silver coated concave mirror 2505 with a 75 cm focal length is kept 20 cm to the side of the collimation mirror 2502. The mirror 2505 is used to collect a fraction of the diffusely reflected light from the sample, and focus it into the input slit of a monochromator 2506. Thus, the beam is incident normally on the sample 2504, but detected at a reflection angle of tan−1(0.2/5) or about 2.3 degrees. Appropriate long wavelength pass filters mounted in a motorized rotating filter wheel are placed in the beam path before the input slit 2506 to avoid contribution from higher wavelength orders from the grating (300 grooves/mm, 2 μm blaze). The output slit width is set to 2 mm corresponding to a spectral resolution of 10.8 nm, and the light is detected by a 2 mm×2 mm liquid nitrogen cooled (77K) indium antimonide (InSb) detector 2507. The detected output is amplified using a trans-impedance pre-amplifier 2507 with a gain of about 105V/A and connected to a lock-in amplifier 2508 setup for high sensitivity detection. The chopper frequency is 400 Hz, and the lock-in time constant is set to 100 ms corresponding to a noise bandwidth of about 1 Hz. These are exemplary elements and parameter values, but other or different optical elements may be used consistent with this disclosure.

Process Analytical Technology (PAT)

One definition of process analytical technology, PAT, is "a system for designing, analyzing and controlling manufacturing through timely evaluations (i.e., during processing) of significant quality and performance attributes of raw and in-process materials and processes, with the goal of ensuring final product quality." Near-infrared or SWIR spectroscopy may have applications in the PAT of the pharmaceutical industry by providing, for example, quantitative analysis of multiple components in a sample and in pack quantification of drugs in formulation, as well as quality of a drug and quality control of complex excipients used in formulation. The PAT process may benefit from near-infrared or SWIR spectroscopy for some steps, such as: raw material identification, active pharmaceutical ingredient applications, drying, granulation, blend uniformity and content uniformity. Some of the strengths of near-infrared or SWIR spectroscopy include: radiation has good penetration properties, and, thus, minimal sample preparation may be required; measurement results may be obtained rapidly, and simultaneous measurements may be obtained for several parameters; non-destructive methods with little or no chemical waste; and organic chemicals that comprise most pharmaceutical products have unique spectra in the near-infrared and SWIR ranges, for example.

One goal of the manufacturing process and PAT may be the concept of a "smart" manufacturing process, which may be a system or manufacturing operation responding to analytical data generated in real-time. Such a system may also have an in-built "artificial intelligence" as decisions may be made whether to continue a manufacturing operation. For example, with respect to the raw materials, integration of the quality measurement into smart manufacturing processes could be used to improve manufacturing operations by ensuring that the correct materials of the appropriate quality are used in the manufacture. Similarly, a smart blender would be under software control and would respond to the real-time spectral data collected.

Figure 26:
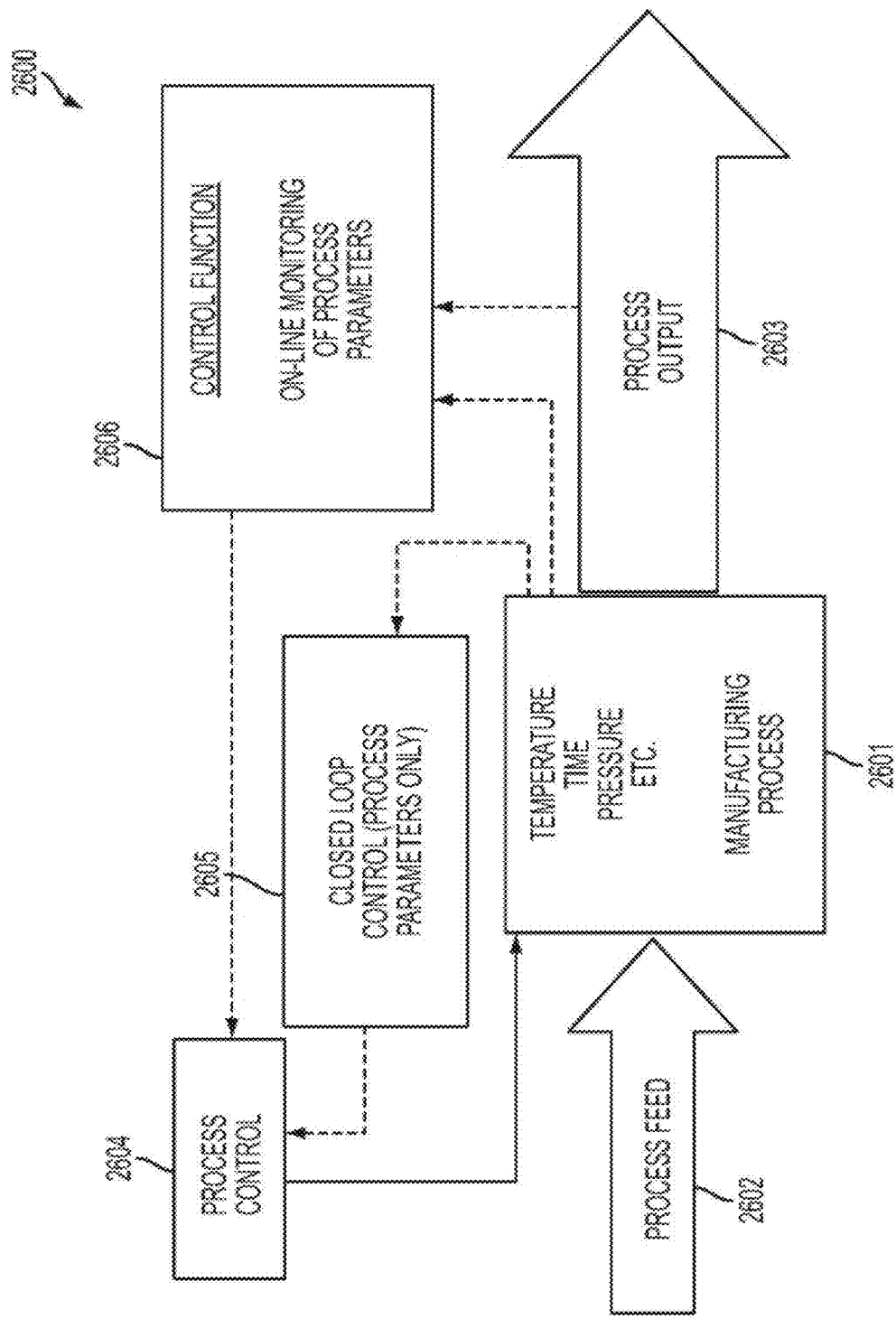
FIG. 26 shows what might be an eventual flow-chart of a smart manufacturing process.

FIG. 26 illustrates what might be an eventual flow-chart 2600 of a smart manufacturing process. The manufacturing process 2601 may have as input the process feed 2602 and result in a process output 2603. A process controller 2604 may at least partially control the manufacturing process 2601, and the controller 2604 may receive inputs from the closed loop control (process parameters) 2605 as well as the on-line monitoring of process parameters 2606. The feedback loops in the process could refine the manufacturing process 2601 and improve the quality of the process output 2603. These are particular embodiments of the use of near-infrared or SWIR spectroscopy in the PAT of the pharmaceutical industry, but other variations, combinations, and methods may also be used and are intended to be covered by this disclosure.

The discussion thus far has included use of near-infrared or SWIR spectroscopy in applications such as identification of counterfeit drugs, detection of illicit drugs, and pharmaceutical process control. Although drugs and pharmaceuticals are one example, many other fields and applications may also benefit from the use of near infrared or SWIR spectroscopy, and these may also be implemented without departing from the scope of this disclosure. As just another example, near-infrared or SWIR spectroscopy may also be used as an analytic tool for food quality and safety control. Applications in food safety and quality assessment include contaminant detection, defect identification, constituent analysis, and quality evaluation. The techniques described in this disclosure are particularly valuable when non-destructive testing is desired at stand-off or remote distances.

Cancer and Other Diagnostics

Breast cancer is considered to be the most common cancer among women in industrialized countries. It is believed that early diagnosis and consequent therapy could significantly reduce mortality. Mammography is considered the gold standard among imaging techniques in diagnosing breast pathologies. However, the use of ionizing radiation in mammography may have adverse effects and lead to other complications. Moreover, screening x-ray mammography may be limited by false positives and negatives, leading to unnecessary physical and psychological morbidity. Although breast cancer is one of the focuses of this disclosure, the same techniques may also be applied to other cancer types, including, for example, skin, prostate, brain, pancreatic, and colorectal cancer.

Diagnostic methods for assessment and therapy follow-up of breast cancer include mammography, ultrasound, and magnetic resonance imaging. The most effective screening technique at this time is x-ray mammography, with an overall sensitivity for breast cancer detection around 75%, which is even further reduced in women with dense breasts to around 62%. Moreover, x-ray mammography has a 22% false positive rate in women under 50, and the method cannot accurately distinguish between benign and malignant tumors. Magnetic resonance imaging and ultrasound are sometimes used to augment x-ray mammography, but they have limitations such as high cost, low throughput, limited specificity and low sensitivity. Thus, there is a continued need to detect cancers earlier for treatment, missed by mammography, and to add specificity to the procedures.

Optical breast imaging may be an attractive technique for breast cancer to screen early, augment with mammography, or use in follow-on treatments. Also, optical breast imaging may be performed by intrinsic tissue contrast alone (e.g., hemoglobin, water, collagen, and lipid content), or with the use of exogenous fluorescent probes that target specific molecules. For example, near-infrared (NIR) light may be used to assess optical properties, where the absorption and scattering by the tissue components may change with carcinoma. For most of the studies conducted to date, NIR light in the wavelength range of 600-1000 nm has been used for sufficient tissue penetration; these wavelengths have permitted imaging up to several centimeters deep in soft tissue. Optical breast imaging using fluorescent contrast agents may improve lesion contrast and may potentially permit detection of changes in breast tissue earlier. In one embodiment, the fluorescent probes may either bind specifically to certain targets associated with cancer or may non-specifically accumulate at the tumor site.

Optical methods of imaging and spectroscopy can be non-invasive using non-ionizing electromagnetic radiation, and these techniques could be exploited for screening of wide populations and for therapy monitoring. "Optical mammography" may be a diffuse optical imaging technique that aims at detecting breast cancer, characterizing its physiological and pathological state, and possibly monitoring the efficacy of the therapeutic treatment. The main constituents of breast tissue may be lipid, collagen, water, blood, and other structural proteins. These constituents may exhibit marked and characteristic absorption features in the NIR wavelength range. Thus, diffuse optical imaging and spectroscopy in the NIR may be helpful for diagnosing and monitoring breast cancer. Another advantage of such imaging is that optical instruments tend to be portable and more cost effective as compared to other instrumentation that is conventionally used for medical diagnosis. This can be particularly true, if the mature technologies for telecommunications and fiber optics are exploited.

Spectroscopy using NIR or short-wave infrared (SWIR) light may be beneficial, because most tissue has organic compounds that have overtone or combination absorption bands in this wavelength range (e.g., between approximately 0.8-2.5 microns). In one embodiment, a NIR or SWIR super-continuum (SC) laser that is an all-fiber integrated source may be used as the light source for diagnosing cancerous tissue. Exemplary fiber-based super-continuum sources may emit light in the NIR or SWIR between approximately 1.4-1.8 microns, 2-2.5 microns, 1.4-2.4 microns, 1-1.8 microns, or any number of other bands. In particular embodiments, the detection system may be one or more photo-detectors, a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

For breast cancer, experiments have shown that with growing cancer the collagen content increases while the lipid content decreases. Therefore, early breast cancer detection may involve the monitoring of absorption or scattering features from collagen and lipids. In addition, NIR spectroscopy may be used to determine the concentrations of hemoglobin, water, as well as oxygen saturation of hemoglobin and optical scattering properties in normal and cancerous breast tissue. For optical imaging to be effective, it may also be desirable to select the wavelength range that leads to relatively high penetration depths into the tissue. In one embodiment, it may be advantageous to use optical wavelengths in the range of about 1000-1400 nm. In another embodiment, it may be advantageous to use optical wavelengths in the range of about 1600-1800 nm. Higher optical power densities may be used to increase the signal-to-noise ratio of the detected light through the diffuse scattering tissue, and surface cooling or focused light may be beneficial for preventing pain or damage to the skin and outer layer surrounding the breast tissue. Since optical energy may be non-ionizing, different exposure times may be used without danger or harmful radiation.

Figure 27:
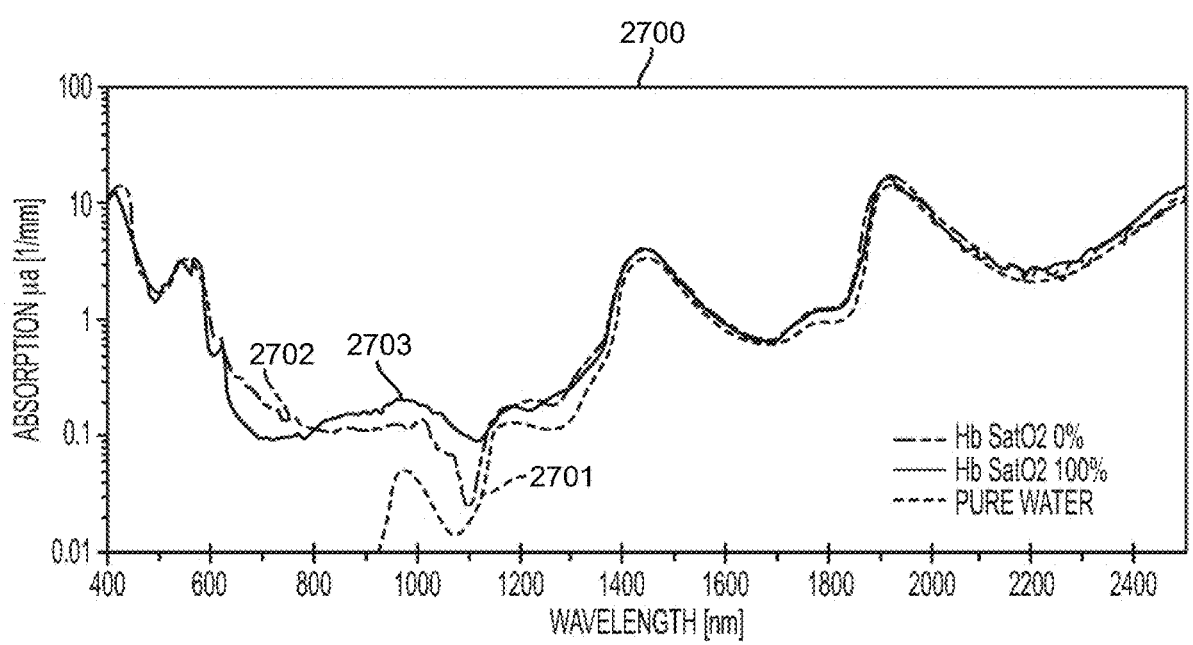
FIG. 27 illustrates the optical absorption of pure water, hemoglobin without oxygen, and hemoglobin saturated with oxygen.

To perform non-invasive optical mammography, one desired attribute is that the light may penetrate as far as possible into the breast tissue. In diffuse reflection spectroscopy, a broadband light spectrum may be emitted into the tissue, and the spectrum of the reflected or transmitted light may depend on the absorption and scattering interactions within the target tissue. Since breast tissue has significant water and hemoglobin content, it is valuable to examine the wavelength range over which deep penetration of light is possible. FIG. 27 illustrates the optical absorption 2700 of pure water (dotted line) 2701, hemoglobin without oxygen (thinner solid line) 2702, and hemoglobin saturated with oxygen (thicker solid line) 2703. It can be noted that above about 1100 nm, the absorption of hemoglobin is almost the same as water absorption. The penetration depth may be proportional to the inverse of the optical absorption. Therefore, the highest penetration depth will be at the absorption valley, approximately in the wavelength range between about 900 nm and about 1300 nm. Although not as low in absorption compared to the first window, another absorption valley lies between about 1600 nm and 1800 nm. Thus, non-invasive imaging preferably should use wavelengths that fall in one of these two absorption valleys.

Figure 28:
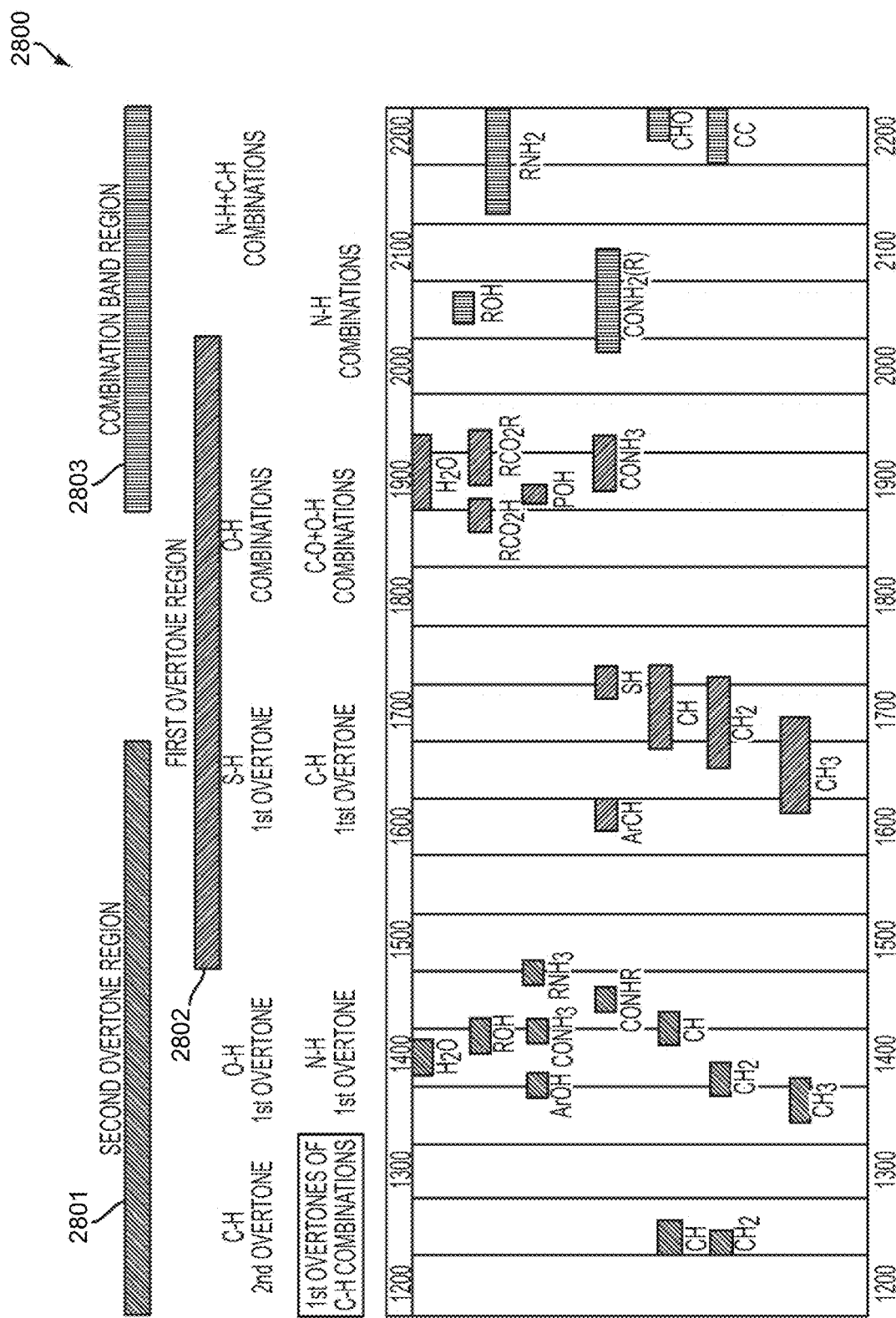
FIG. 28 shows examples of various absorption bands of chemical species in the wavelength range between about 1200-2200 nm.

FIG. 28 shows examples of various absorption bands of chemical species 2800 in the wavelength range between about 1200 nm and 2200 nm. Although the fundamental absorptions usually lie in the mid-infrared (e.g., wavelengths longer than about 3 microns), there are many absorption lines in the NIR corresponding to the second overtone region 2801 between about 1000 nm and 1700 nm, the first overtone region 2802 between about 1500 nm and 2050 nm, and the combination band region 2803 between about 1900 nm and 2300 nm. As an example, hydrocarbon bonds common in many biological substances have their fundamental absorption in the mid-IR near 3300-3600 nm, but they also have many combination band lines between 2000-2500 nm, and other lines at shorter wavelengths corresponding to the first and second overtones. Fortunately, there are spectral features of FIG. 28 that overlap with the absorption valleys in FIG. 27. These are likely to be the wavelengths of interest for spectroscopic analysis of cancerous regions.

Figure 29:
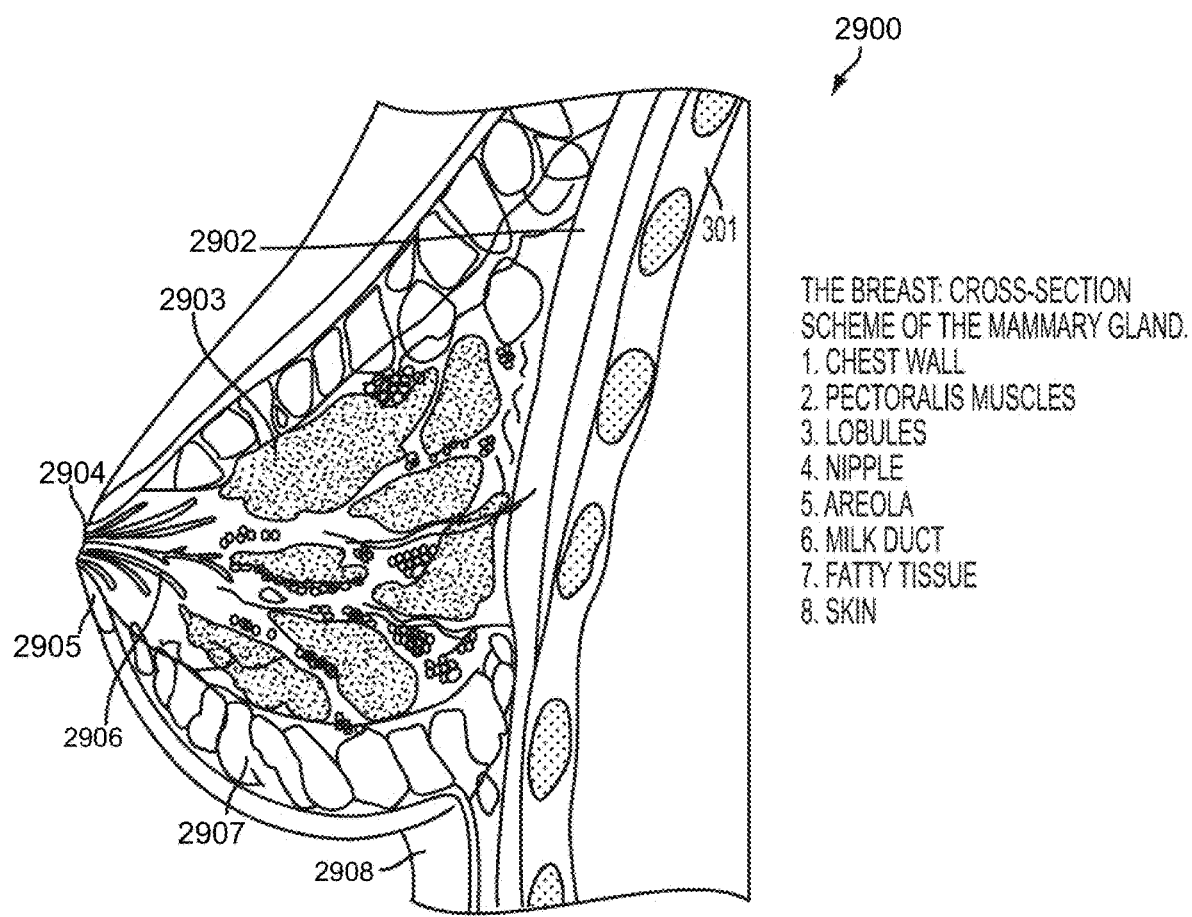
FIG. 29 depicts the structure of a female breast.

In women, the breasts (FIG. 29) 2900 overlay the pectoralis major muscles 2902 and cover much of the chest area and the chest walls 2901. The breast is an apocrine gland that produces milk to feed an infant child; the nipple 2904 of the breast is surrounded by an areola 2905, which has many sebaceous glands. The basic units of the breast are the terminal duct lobules 2903, which produce the fatty breast milk. They give the breast its function as a mammary gland. The lobules 2903 feed through the milk ducts 2906, and in turn these ducts drain to the nipple 2904. The superficial tissue layer (superficial fascia) may be separated from the skin 2908 by about 0.5-2.5 cm of adipose of fatty tissue 2907.

Breast cancer is a type of cancer originating from breast tissue, most commonly from the inner lining of milk ducts 2906, the lobules 2903 that supply the ducts with milk, and/or the connective tissue between the lobules. Cancers originating from ducts 2906 are known as ductal carcinomas, while those originating from lobules 2903 or their connective tissue are known as lobular carcinomas. While the overwhelming majority of human cases occur in women, male breast cancer may also occur.

Figure 30:
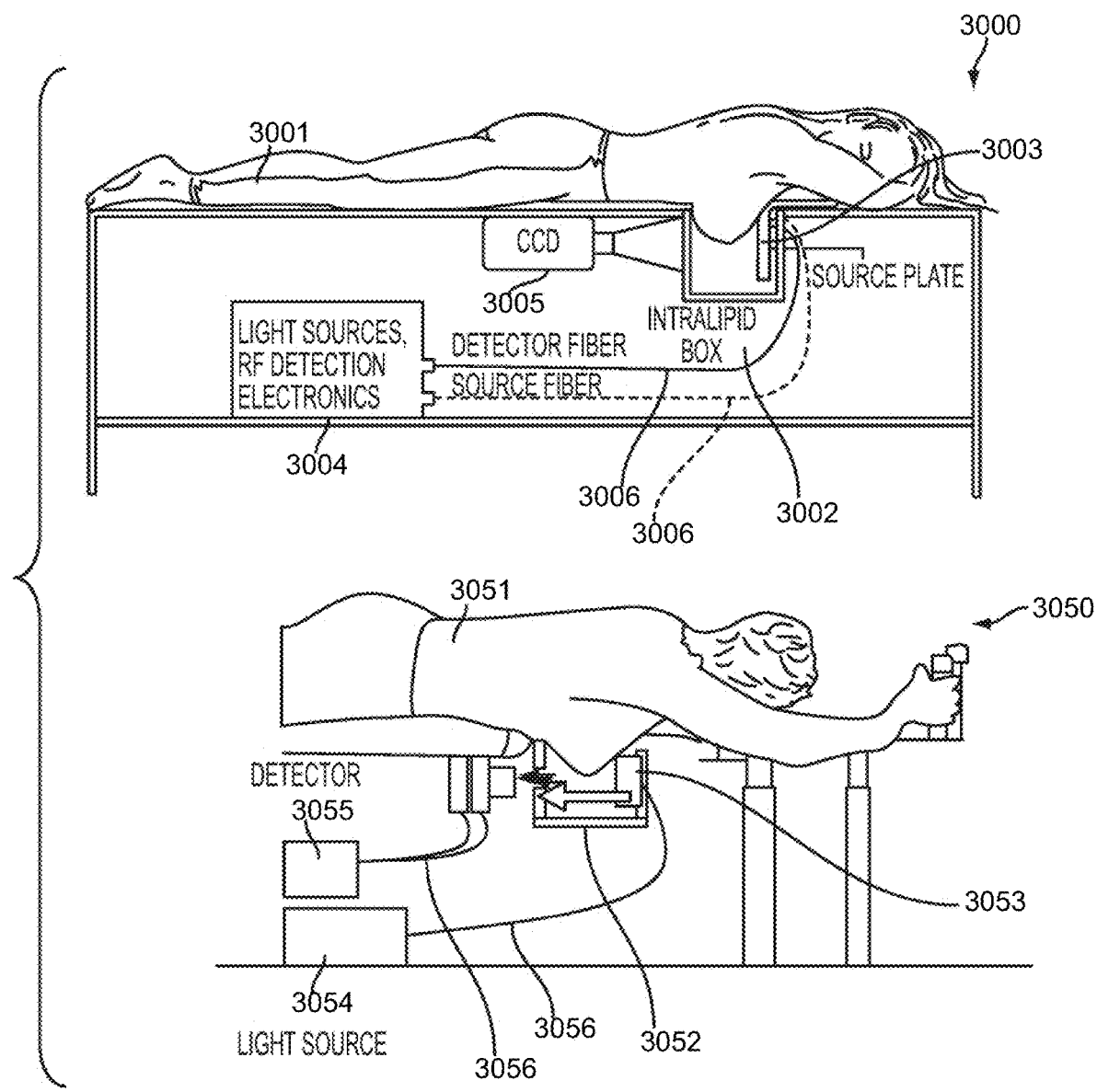
FIG. 30 illustrates particular embodiments of imaging systems for optically scanning a breast.

Several particular embodiments of imaging systems 3000, 3050 for optically scanning a breast are illustrated in FIG. 30. In these particular embodiments, the patient 3001, 3051 may lie in a prone position with her breasts inside a box 3002, 3052 with probably a transparent window on the detector side. A compression plate 3003, 3053 may hold the breast in place against the viewing window by mildly compressing the breast to a thickness between about 5.5 and 7.5 cm. The box 3002, 3052 may then be filled with a matching fluid with optical properties similar to human breast. In one instance, the matching fluid may comprise water, india ink for absorption, and a fat emulsion for scattering. The embodiments in FIG. 30 may also have one or more detectors 3004, 3055, one or more light sources 3004, 3054, various electronics, and even an imaging system based on charge coupled devices 3005. As illustrated in FIG. 30, the light sources 3004, 3054 and detectors 3004, 3055 may be coupled to the box 3002, 3052 through one or more fibers 3006, 3056. Also, the imaging may be in reflection mode (top of FIG. 30), transmission mode (bottom of FIG. 30), or some combination.

Beyond the geometry and apparatus of FIG. 30, the optical imaging system may use one or more of three different illumination methods: continuous wave, time-domain photon migration, and frequency-domain photon migration. In one embodiment, continuous-wave systems emit light at approximately constant intensity or modulated at low frequencies, such as 0.1-100 kHz. In another embodiment, the time-domain photon migration technique uses relatively short, such as 50-400 psec, light pulses to assess the temporal distribution of photons. Since scattering may increase the times of flight spent by photons migrating in tissues, the photons that arrive earliest at the detector probably encountered the fewest scattering events. In yet another embodiment, the frequency-domain photon migration devices modulate the amplitude of the light that may be continuously transmitted at relatively high frequencies, such as 10 MHz to 1 GHz. For example, by measuring the phase shift and amplitude decay of photons as compared to a reference signal, information may be acquired on the optical properties of tissue, and scattering and absorption may be distinguished. Beyond these three methods, other techniques or combinations of these methods may be used, and these other methods are also intended to fall within the scope of this disclosure.

Although particular embodiments of imaging architectures are illustrated in FIG. 30, other system architectures may also be used and are also intended to be covered by this disclosure. For example, in one embodiment several couples of optical fibers for light delivery and collection may be arranged along one or more rings placed at different distances from the nipple 2904. In an alternate embodiment a "cap" with fiber leads for light sources and detectors may be used that fits over the breast. In yet another embodiment, imaging optics and light sources and detectors may surround the nipple 2904 and areola 2905 regions of the breast. As yet another alternative, a minimally invasive procedure may involve inserting needles with fiber enclosure (to light sources and detectors or receivers) into the breast, so as to probe regions such as the lobules 2903 and connective tissue. Both non-invasive and minimally invasive optical imaging methods are intended to be covered by this disclosure.

Optical Wavelength Ranges for Cancer Detection

Figure 31:
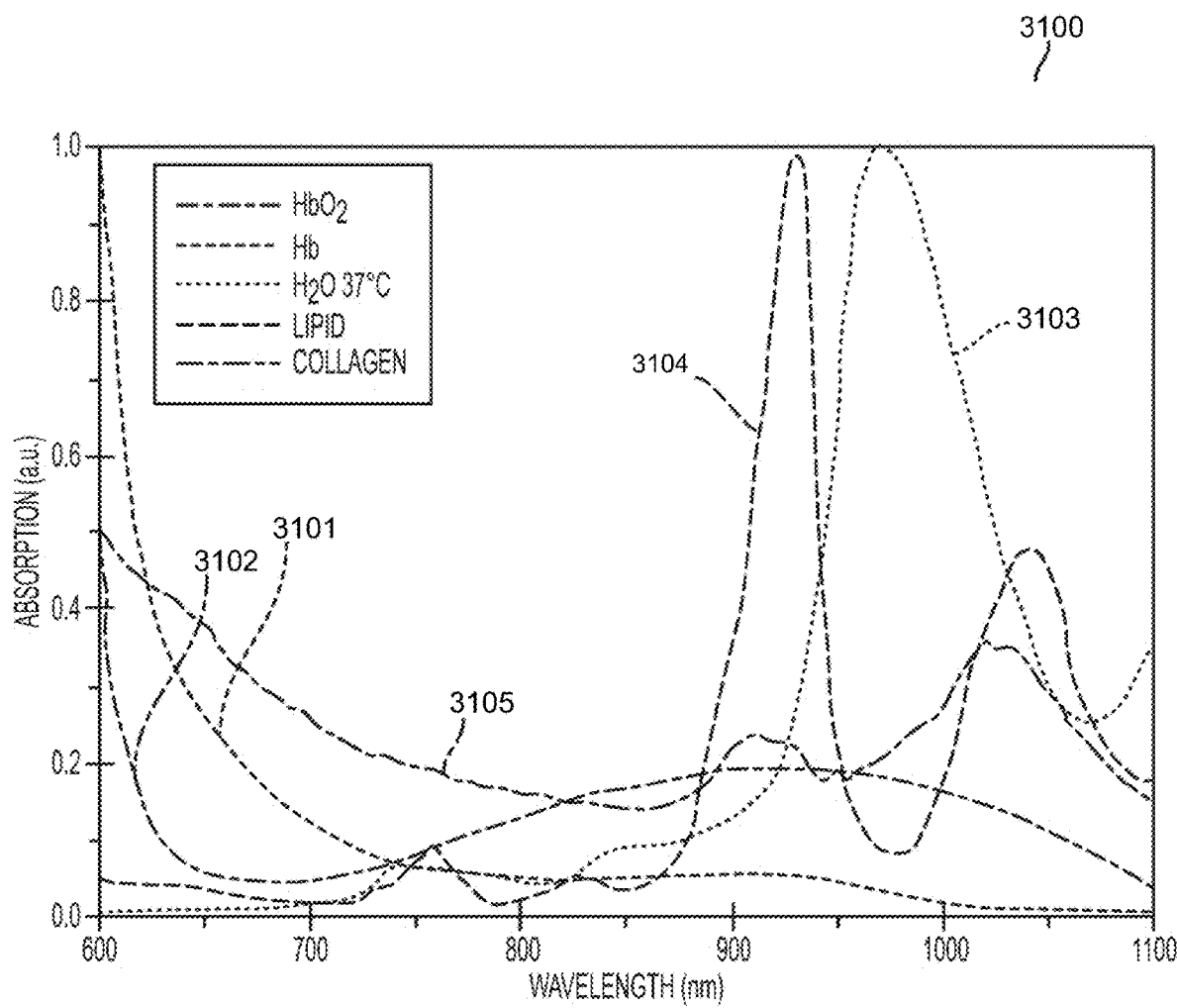
FIG. 31 shows the normalized absorption spectra of main tissue absorbers in the NIR for breast cancer, between about 600-1100 nm.

Many of the diffuse optical tomography studies previously conducted have relied on using NIR in the wavelength range of about 600-1000 nm, where light absorption at these wavelengths may be minimal, allowing for sufficient tissue penetration (up to 15 cm). In these wavelength ranges, it has been claimed that concentrations of oxy- and deoxy-hemoglobin, water, and lipids can be determined. For example, FIG. 31 shows the normalized absorption spectra 3100 of main tissue absorbers in the NIR between about 600 nm and 1100 nm: deoxy-hemoglobin, Hb, 3101, oxy-hemoglobin, HbO2, 3102, water 3103, lipids 3104 and collagen 3105. It is speculated that in a malignant tumor, hemoglobin concentration may be directly related to angiogenesis, one of the main factors required for tumor growth and metastases. Moreover, the proportions of oxy- and deoxy-hemoglobin in a tumor may change due to its metabolism. Thus, by measuring concentrations of the breast components, discrimination of benign and malignant tumors may be possible with diffuse optical imaging. Experiment evidence suggests that cancerous tissue is associated with higher hemoglobin and water concentrations, and a lower lipid concentration with respect to normal breast tissue.

Based on FIG. 27 and the dynamics of carcinoma, it may be advantageous to perform spectroscopy in longer wavelengths, such as windows between 1000-1400 nm or 1600-1800 nm. For example, looking at the absorption curves 2700 in FIG. 27, the absorption between approximately 1000-1300 nm may be comparable to the 600-1000 nm window described in FIG. 31. However, the loss through the soft tissue medium (penetration depth may be inversely related to the loss) will be due to absorption and scattering. In fact, the scattering properties of tissue may also contain valuable information for lesion diagnosis. Since the scattering is inversely proportional to some power of wavelength (for example, in some tissue scattering is inversely proportional to the wavelength cubed), the scattering contribution to the loss may decrease at longer wavelengths. Moreover, these longer wavelength windows may contain diagnostic information on content of collagen and adipose, both of which may be significant indicators for breast cancer.

Figure 32:
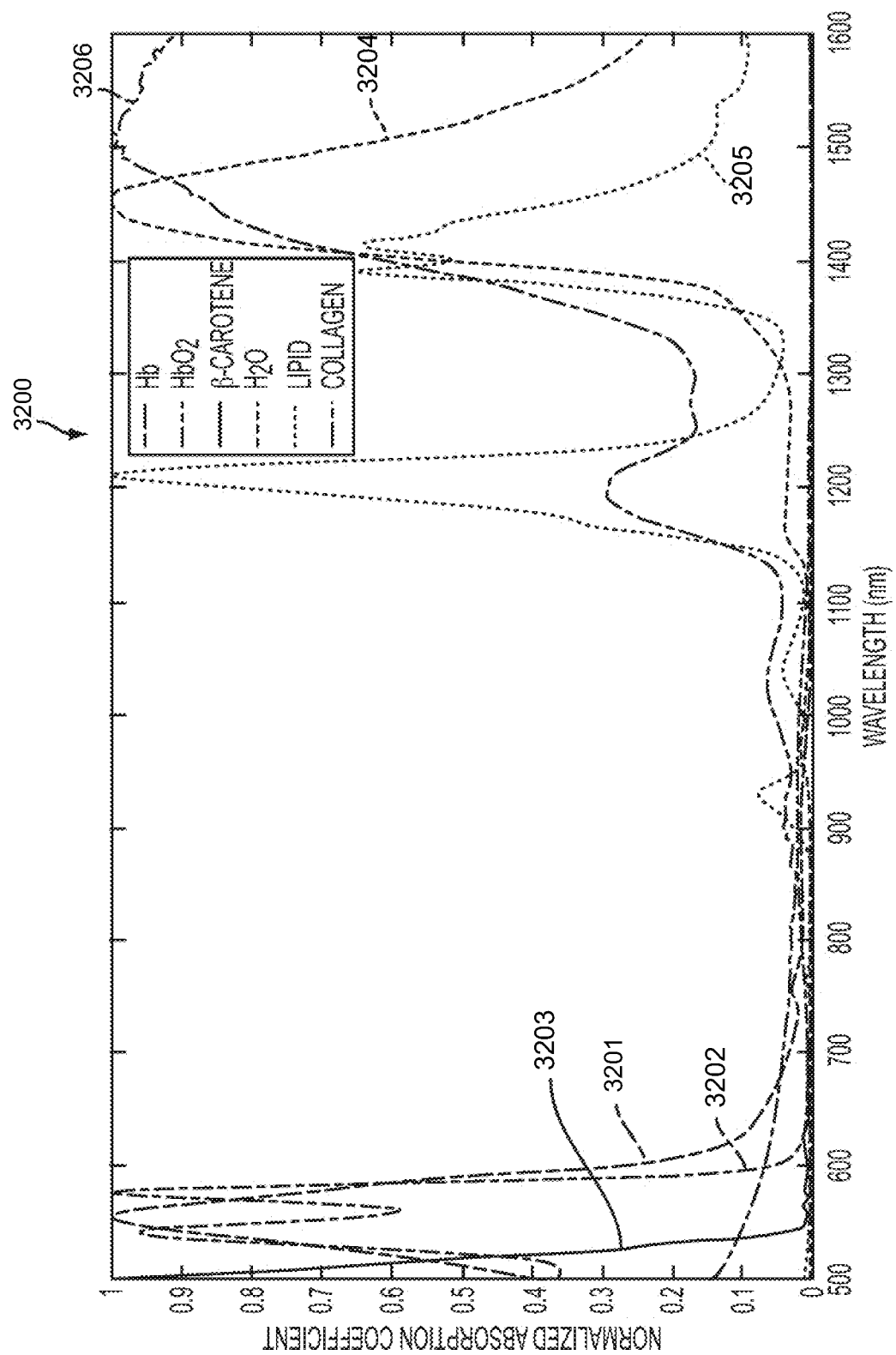
FIG. 32 illustrates the normalized absorption coefficient in the wavelength range between about 500-1600 nm for many of the components of breast tissue.

Breast cancer spectroscopy may benefit from the use of wavelengths longer than about 1000 nm for a number of reasons. As one example, the main absorbers in soft tissues of the visible spectrum of light may be oxy- and deoxygenated hemoglobin and beta-carotene. On the other hand, primary absorbers in the near-infrared spectrum of light may be water, adipose tissue and collagen. Particularly adipose and collagen content may be valuable for early detection of cancers. In one embodiment, increased levels of collagen in breast malignancies are thought to be due to increased vascularity of the tumors. Collagen type I may be an important component of artery walls. FIG. 32 illustrates the normalized absorption coefficient 3200 in the wavelength range between about 500 nm and 1600 nm for Hb 3201, HbO2 3202, beta-carotene 3203, water 3204, lipid 3205 and collagen 3206.

Collagen and Adipose Signatures in Near-IR

Examining the collagen content may be a valuable indicator for breast cancer detection. Collagen is one of the important extracellular matrix proteins, and fibrillar collagens help to determine stromal architecture. In turn, changes in the stromal architecture and composition are one of the aspects of both benign and malignant pathologies, and, therefore, may play an initial role in breast carcinogenesis. For example, collagen seems to be related to cancer development, because high mammographic density may be recognized as a risk factor for breast cancer. Moreover, collagen type in high-risk dense breasts may appear to be different from collagen in low-density breasts.

Experimental data also shows that malignant mammary gland tissues of animals and humans show a decrease in lipids when compared to normal tissues. The reduced amounts of lipids in the cancerous sites may be caused by a high metabolic demand of lipids in the malignant tumors. For example, due to the rapid proliferation of cancerous cells, there may be reduced lipid content in cancerous tissues. Thus, in addition to collagen, another valuable marker for breast cancer may be the lipid spectral features. It may also be possible to combine the markers from oxy- and deoxygenated hemoglobin and water with lipid and collagen lines to improve the diagnostics and/or therapeutics of optical imaging and/or treatment for breast and other types of cancer. Although specific examples of tissue constituents are discussed, other tissue constituents and related markers may also be associated with breast cancer and other cancers, and these other constituents are also intended to be covered by this disclosure.

Figure 33A:
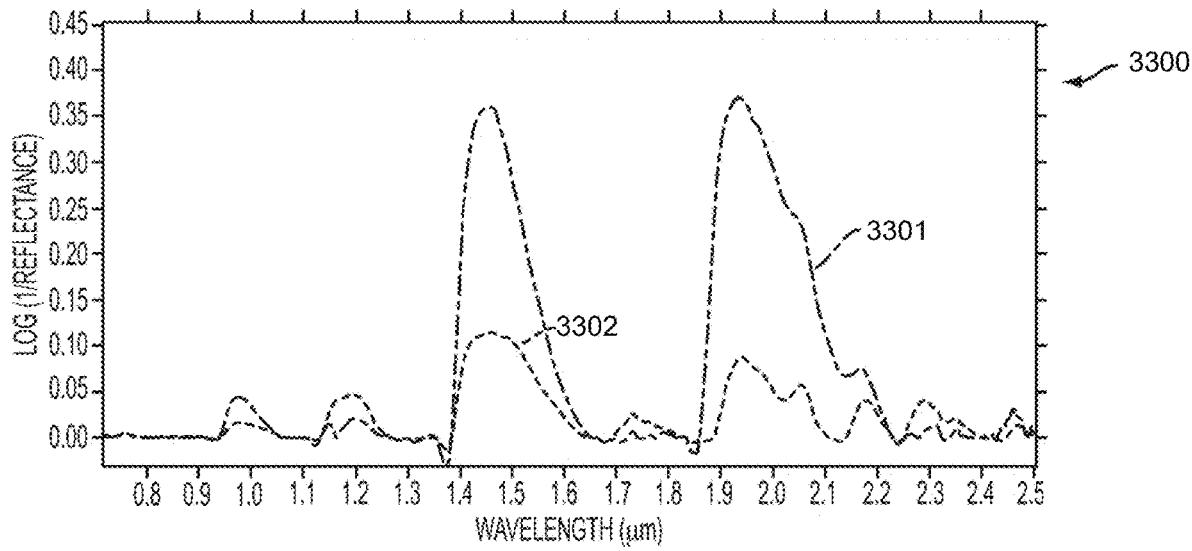
FIGS. 33A and 33B show the typical spectra of the cancerous site of a treated rat and the corresponding site of a normal rat.
Figure 33B:
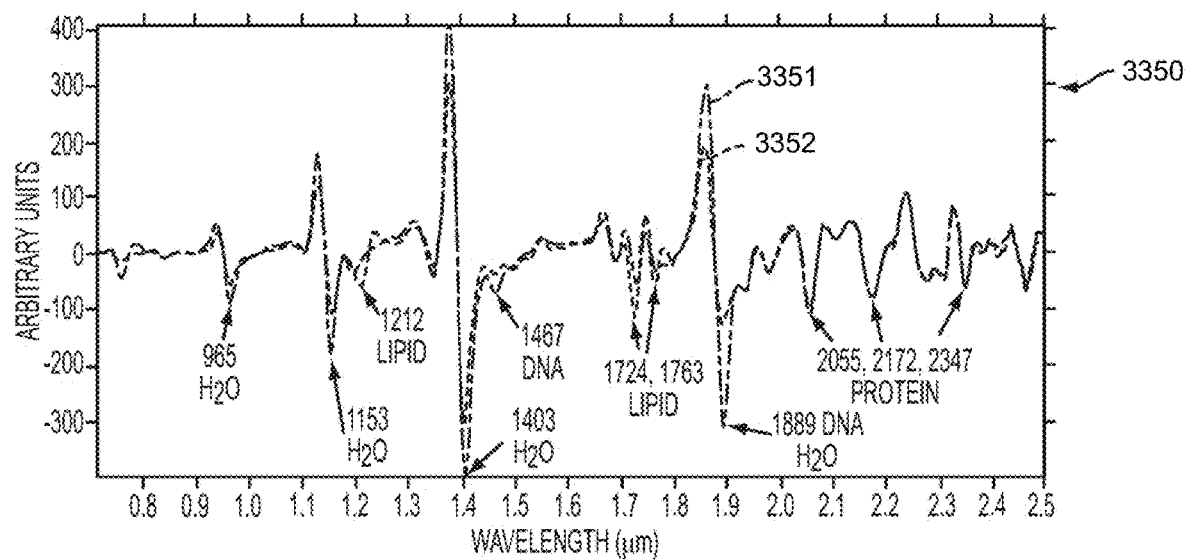

As an example of the types of spectral signatures that may exist, in vivo investigations of progressive changes in rat mammary gland tumors were conducted using near-infrared spectroscopy with a Fourier-transform infrared spectrometer. In one embodiment, FIG. 33 shows the typical spectra of the cancerous site of the treated rat and the corresponding site of the normal rat. FIG. 33A shows the logarithm of the inverse of reflection spectra 3300, while FIG. 33B shows their second derivative spectra 3350. The curves 3301, 3351 correspond to the spectra of the cancerous sites, while 3302, 3352 correspond to the spectra of the normal sites. Since the second derivative techniques may be useful in the analyses of NIR spectra to minimize baseline offsets and to resolve overlapping absorption without compromising signal-to-noise, FIG. 33B may be used for interpretation of the spectral changes.

In FIG. 33B identification may be made of several of the spectral features. In particular, there are DNA bands near 1471 nm and 1911 nm, while there are water bands near 967 nm, 1154 nm, 1402 nm, and 1888 nm. Moreover, there are lipid bands near 1209 nm, 1721 nm and 1764 nm, and there are protein bands near 2055 nm, 2172 nm and 2347 nm. The NIR spectra of FIG. 33 show that the DNA and water contents in the cancerous tissue may be higher than those in normal tissues. On the other hand, the lipid content in the cancerous tissue may be less than the lipid content in normal tissues. With protein contents, however, little difference may be found between the normal and cancerous tissue.

Figure 34:
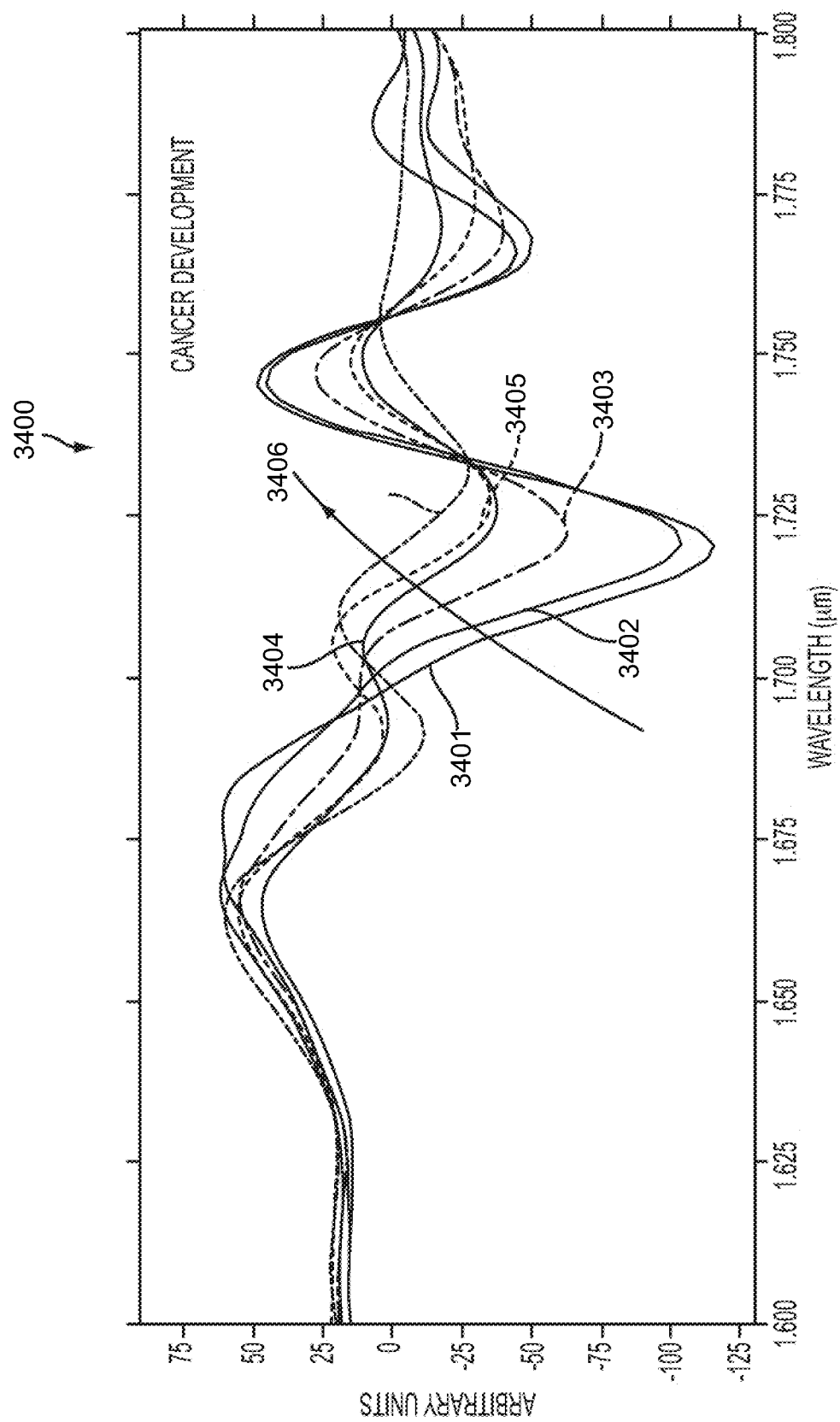
FIG. 34 shows the second derivative of spectral changes over several weeks between about 1600-1800 nm in rats with breast cancer.

These experiments on rats with breast cancer were also used to observe the temporal progression of the cancer. In this embodiment, as the cancer grew, the lipid band intensity decreased, and this band also shifted to higher wavelengths, and collagen peaks appeared in the tissues. In FIG. 34, the second derivative spectral changes 3400 were investigated in the 1600 nm to 1800 nm wavelength range over several weeks. An early cancer was detected in the 5th week, and then it grew rapidly from the 6th 3401 to the 7th 3402 week. The cancer's temporal progression through the 8th 3403, 9th 3404, 10th 3405 and 11th 3406 week are shown in the various curves in FIG. 34. With the cancer growth, the intensity of the lipid band in the vicinity of 1721 nm decreased, and this band shifted to higher wavelengths by 7 nm at the 11th week 3406 compared to the wavelength band at the 5th week. The higher wavelength shift may indicate that an order parameter of the lipids increases with progressive cancer growth.

Figure 37:
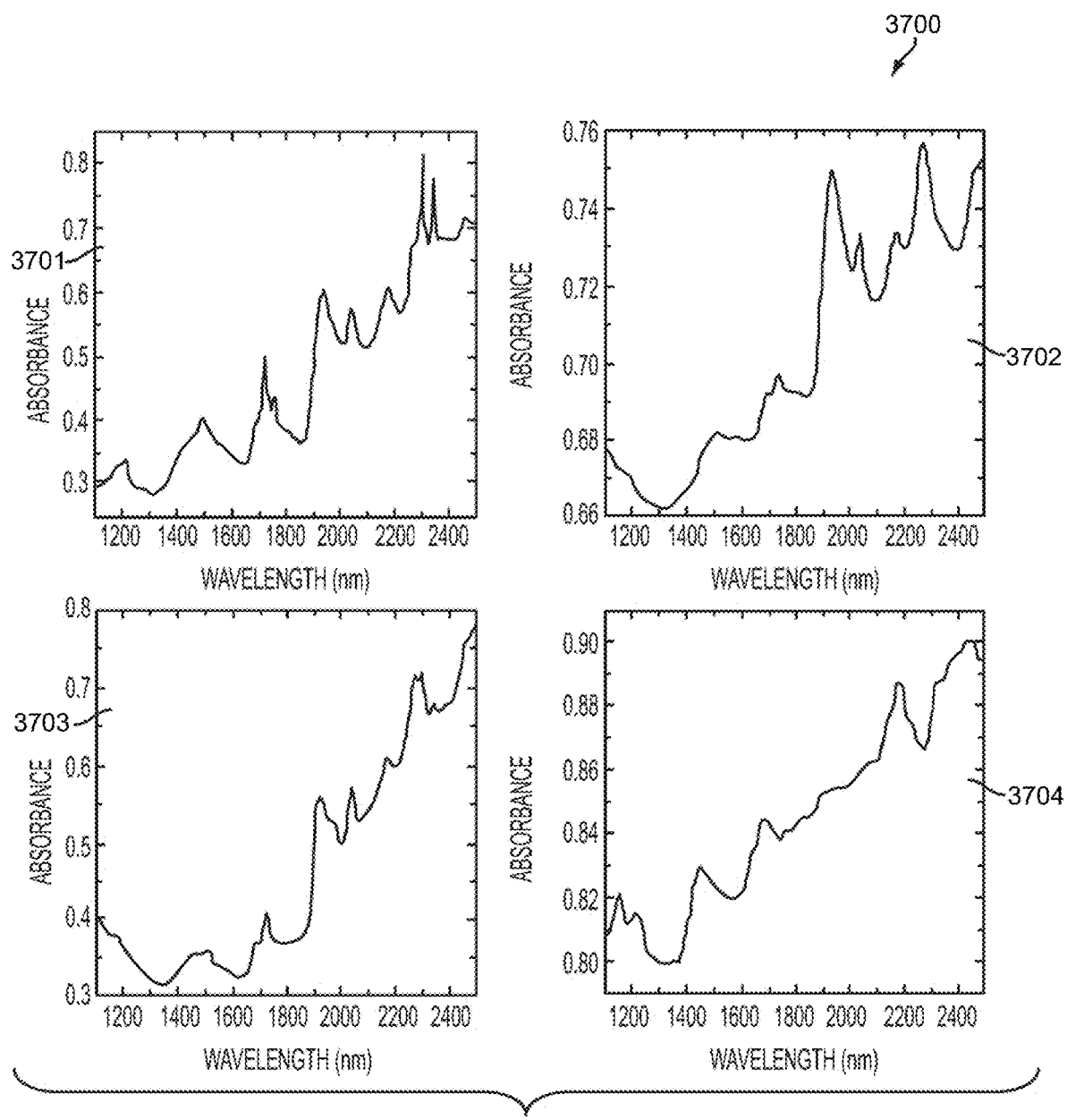
FIG. 37 illustrates the absorbance for four types of collagen: collagen I, collagen II, collagen III, and collagen IV.

Moreover, in the data of FIG. 34 is seen that a new peak appeared as the cancer grew around 1690 nm, which may be assigned to be a collagen absorption by comparison with the absorptions of standard collagen (c.f., FIG. 37). The higher wavelength shift may be attributable to the formation of elastic fibers in the lipid layer with collagen induced in the cancer tissues, thus leading to an increased order parameter of the lipids. Thus, it can be seen that significant information about breast cancer tissue compared with normal tissue may be obtained by spectroscopy at the longer wavelengths in the near-infrared.

Figure 35:
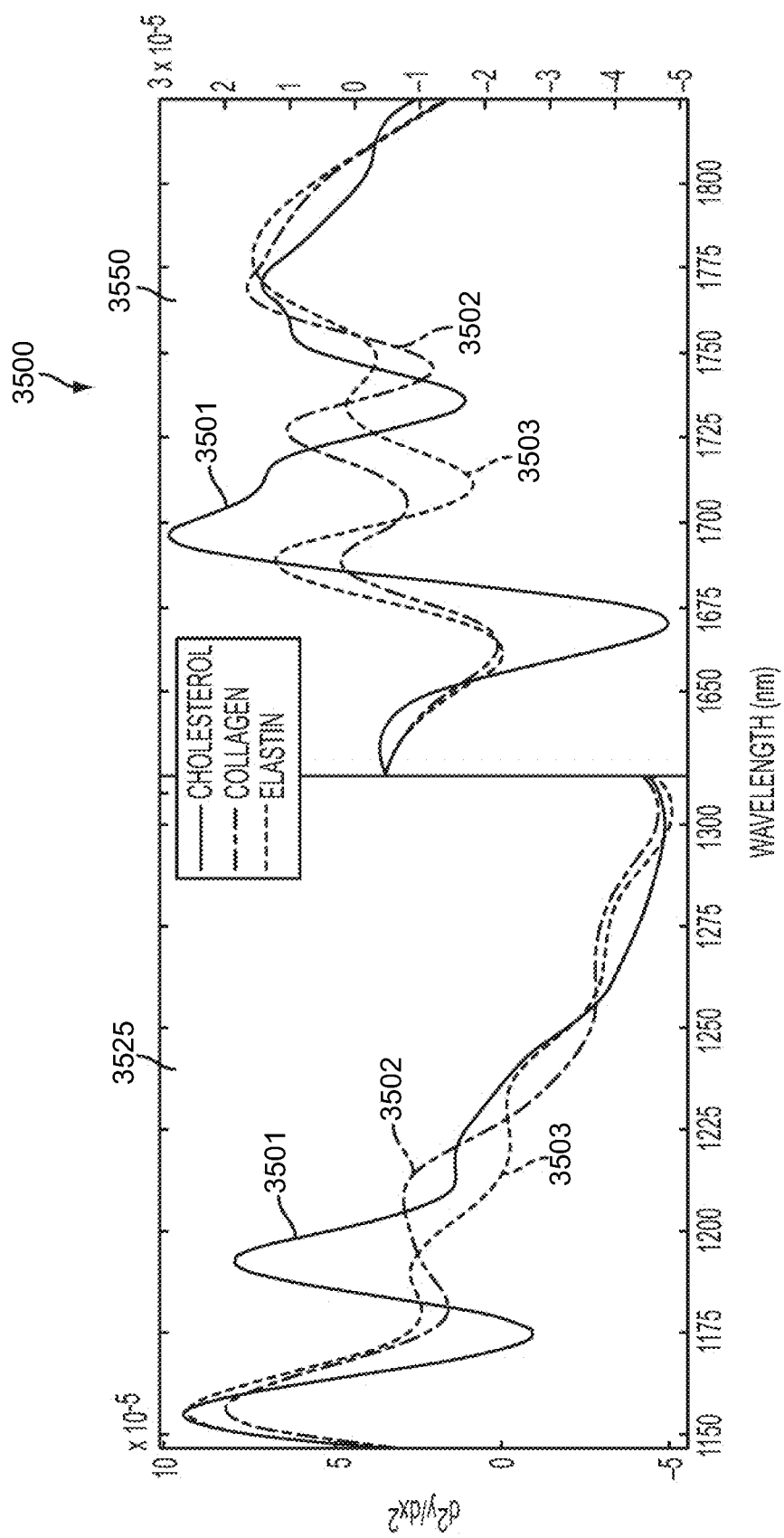
FIG. 35 illustrates the second derivative spectra for cholesterol, collagen and elastin.

The second derivative spectra may also be insightful for observing and monitoring changes in tissue as well as characterizing tissue in the near-infrared wavelength range. As an example, FIG. 35 illustrates the second derivative spectra 3500 for cholesterol (similar to one embodiment of lipids) 3501, collagen 3502, and elastin 3503. The left curve 3525 shows the second derivative data over the wavelength range of about 1150 nm to 1300 nm, while the right curve 3550 shows the second derivative data over the wavelength range of about 1600 nm to 1850 nm. These wavelengths show numerous features for cholesterol/lipid 3501, collagen 3502, and elastin 3503, which again emphasizes the added value of using wavelengths longer than about 1000 nm for cancer diagnostics.

Figure 36:
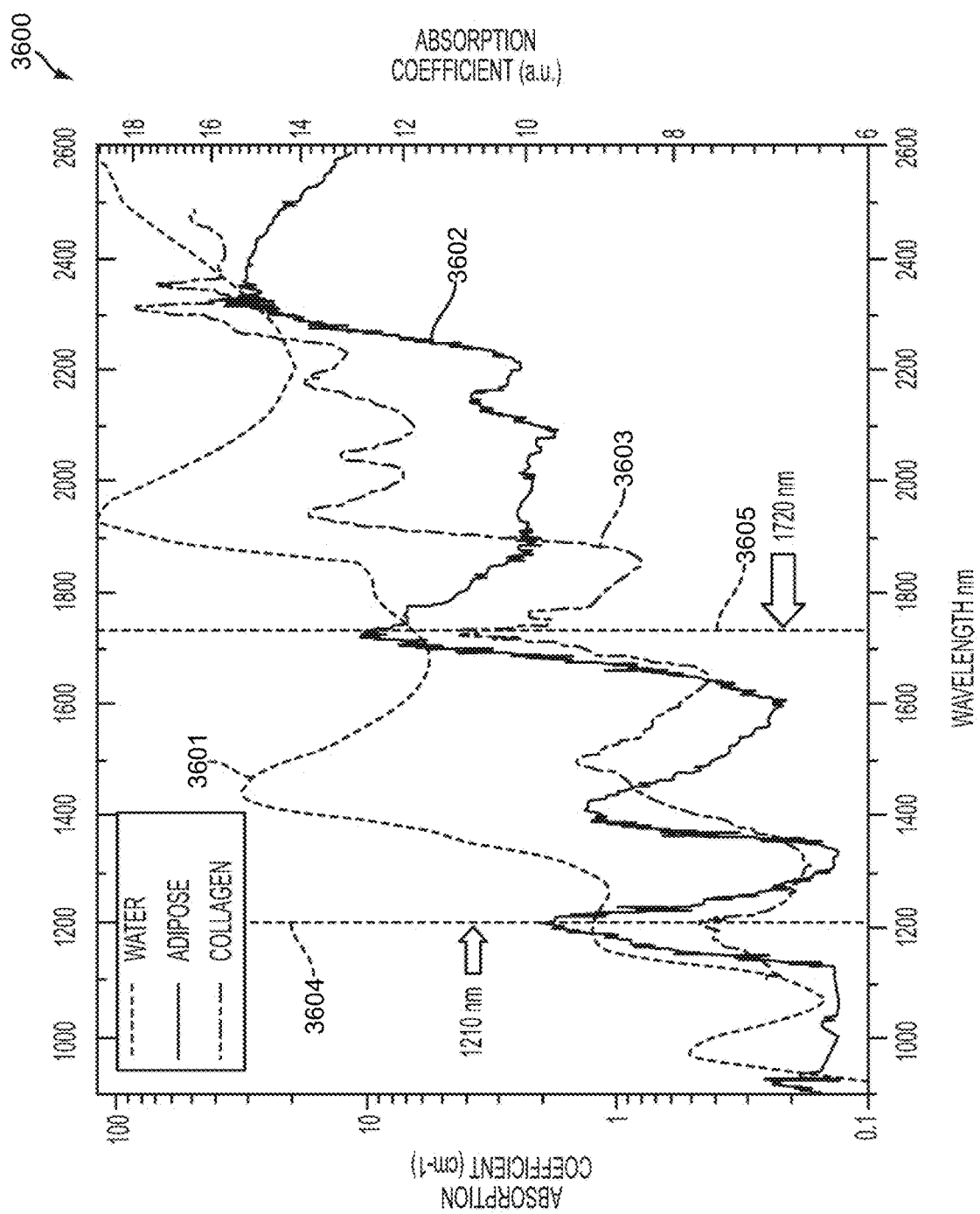
FIG. 36 shows the absorption coefficient as a function of wavelength between about 1000 nm and 2600 nm for water, adipose and collagen.

To further illustrate the value of using longer wavelengths in the NIR or SWIR for observing changes in breast cancer and other cancer markers, the spectra of in water, lipids/adipose and collagen of different varieties may be studied. As one embodiment, the absorption coefficients 1000 are shown in FIG. 36 as a function of wavelength between about 1000 nm and 2600 nm. FIG. 36 overlaps the absorption coefficient for water 3601, adipose 3602 (forms of adipose include fatty tissue and acids, lipids, and cholesterol), and collagen type I 3603. One may note that particular absorption peaks for adipose 3602 and collagen type I 3603 align at wavelengths near 1210 nm 3604 and 1720 nm 3605, which also correspond to local minima in water absorption.

Moreover, the NIR spectra for collagen also depend on the type of collagen. As an example, FIG. 37 illustrates the absorbance 3700 for four types of collagen: collagen I 3701, collagen II 3702, collagen III 3703, and collagen IV 3704. Collagen I, for instance, may be a major constituent of stroma. Also, collagen I and collagen III may be the principal collagens of the aorta. Since the spectra of the four collagens are distinctive, multicomponent analysis of collagens may possibly be used to distinguish the type of collagen involved.

The experimental results discussed thus far indicate that breast cancer detection may benefit from spectroscopy in the NIR and SWIR, particularly wavelengths between approximately 1000-1400 nm and 1600-1800 nm. These are wavelength windows that may have deep penetration into soft tissue, while still falling within lower absorption valleys of water. Moreover, the longer wavelengths lead to less scattering in tissue and water, again permitting deeper penetration of the light. In the NIR and SWIR wavelength range, the spectra of standard samples of cholesterol, protein, collagen, elastin and DNA were measured to obtain information on their characteristic bands in the spectra of mammary gland tissues. Absorption peaks in the standard samples occur at the following exemplary wavelengths:

Collagen: 1182 nm, 1360 nm, 1426 nm, 1496 nm, 1569 nm, 1690 nm, 1732 nm;
Lipids: 1157 nm, 1209 nm, 1404 nm, 1721 nm, 1764 nm;
Cholesterol: 918 nm, 1195 nm, 1376 nm, 1585 nm, 1711 nm, 1757 nm;
Protein: 910 nm, 1143 nm, 1186 nm, 1279 nm, 1420 nm, 1503 nm, 1579 nm, 1690 nm, 1739 nm, 1799 nm; and
DNA: 1414 nm, 1471 nm, 1626 nm, 1728 nm.

Comparing these absorption features with the data in FIGS. 32-37 shows that there are absorption features or signatures in the second derivatives that can be used to monitor changes in, for example, collagen and lipids. By using broadband light and performing spectroscopy in at least some part of the wavelength windows between about 1000-1400 nm and/or 1600-1800 nm, the collagen and lipid changes, or other constituent changes, may be monitored. In one embodiment, for breast cancer the decrease in lipid content, increase in collagen content, and possible shift in collagen peaks may be observed by performing broadband light spectroscopy and comparing normal regions to cancerous regions as well as the absorption strength as a function of wavelength. The spectroscopy may be in transmission, reflection, diffuse reflection, diffuse optical tomography, or some combination. Also, this spectroscopy may be augmented by fluorescence data, if particular tags or markers are added. Beyond looking at the absorbance, the data processing may involve also observing the first, second, or higher order derivatives.

Broadband spectroscopy is one example of the optical data that can be collected to study breast cancer and other types of cancer. However, other types of spectral analysis may also be performed to compare the collagen and lipid features between different wavelengths and different tissue regions (e.g., comparing normal regions to cancerous regions), and these methods also fall within the scope of this disclosure. For example, in one embodiment just a few discrete wavelengths may be monitored to see changes in lipid and collagen contents. In a particular embodiment, wavelengths near 1200 nm may be monitored in the second derivative data of FIG. 35 to measure the cholesterol/lipid peak below 1200 nm in 3501 versus the collagen peak above 1200 nm in 3502. In yet another embodiment, the absorption features in FIG. 32 may be relied upon to monitor the lipid content 3205 by measuring near 1200 nm and the collagen content 3206 by measuring near 1300 nm. Although these embodiments use only two wavelengths, any number of wavelengths may be used and are intended to be covered by this disclosure.

Thus, a breast cancer monitoring system, or a system to monitor different types of cancers, may comprise broadband light sources and detectors to permit spectroscopy in transmission, reflection, diffuse optical tomography, or some combination. In one particular embodiment, high signal-to-noise ratio may be achieved using a fiber-based super-continuum light source (described further herein). Other light sources may also be used, including a plurality of laser diodes, super-luminescent laser diodes, or fiber lasers.

Wavelength ranges that may be advantageous for cancer detection include the NIR and SWIR windows (or some part of these windows) between about 1000-1400 nm and 1600-1800 nm. These longer wavelengths fall within local minima of water absorption, and the scattering loss decreases with increasing wavelength. Thus, these wavelength windows may permit relatively high penetration depths. Moreover, these wavelength ranges contain information on the overtone and combination bands for various chemical bonds of interest, such as hydrocarbons.

These longer wavelength ranges may also permit monitoring levels and changes in levels of important cancer tissue constituents, such as lipids and collagen. Breast cancer tissue may be characterized by decreases in lipid content and increases in collagen content, possibly with a shift in the collagen peak wavelengths. The changes in collagen and lipids may also be augmented by monitoring the levels of oxy- and deoxy-hemoglobin and water, which are more traditionally monitored between 600-1000 nm. Other optical techniques may also be used, such as fluorescent microscopy.

To permit higher signal-to-noise levels and higher penetration depths, higher intensity or brightness of light sources may be used. With the higher intensities and brightness, there may be a higher risk of pain or skin damage. At least some of these risks may be mitigated by using surface cooling and focused infrared light, as further described herein.

Laser Experiments: Penetration Depth, Focusing, Skin Cooling

Some preliminary experiments show the feasibility of using focused infrared light for non-invasive procedures, or other procedures where relatively shallow vessels below the skin are to be thermally coagulated or occluded with minimum damage to the skin upper layers. In one embodiment, the penetration depth and optically induced thermal damage has been studied in chicken breast samples. Chicken breast may be a reasonable optical model for smooth muscle tissue, comprising water, collagen and proteins. Commercially available chicken breast samples were kept in a warm bath (~32 degree Celsius) for about an hour, and then about half an hour at room temperature in preparation for the measurements.

Figure 38:
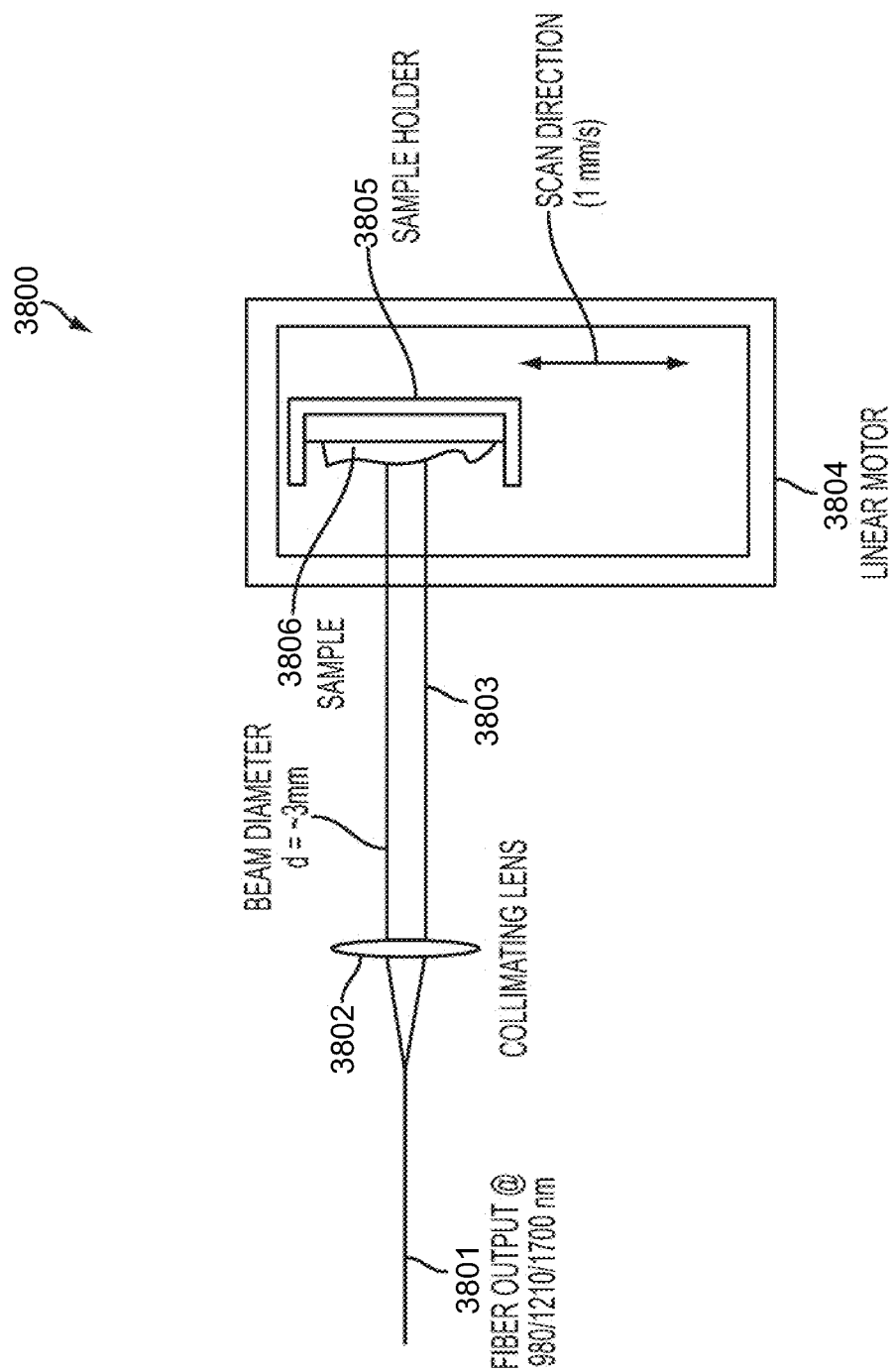
FIG. 38 shows an experimental set-up for testing chicken breast samples using collimated light. In this experiment, the collimated light has a beam diameter of about 3 mm.

An exemplary set-up 3800 for testing chicken breast samples using collimated light is illustrated in FIG. 38. The laser light 3801 near 980 nm, 1210 nm, or 1700 nm may be provided from one or more laser diodes or fiber lasers, as described further below. In this instance, laser diodes were used, which comprise a plurality of laser diode emitters that are combined using one or more multiplexers (particularly spatial multiplexers), and then the combined beam is coupled into a multi-mode fiber (typically 100 microns to 400 microns in diameter). The output from the laser diode fiber was then collimated using one or more lenses 3802. The resulting beam 3803 was approximately round with a beam diameter of about 3 mm. The beam diameter was verified by blade measurements (i.e., translating a blade across the beam). Also, the time-averaged power was measured in the nearly collimated section after the lens using a large power meter. The chicken breast samples 3806 were mounted in a sample holder 3805, and the sampler holder 3805 was mounted in turn on a translation stage 3804 with a linear motor that could move perpendicular to the incoming laser beam. Although particular details of the experiment are described, other elements may be added or eliminated, and these alternate embodiments are also intended to be covered by this disclosure.

Figure 39:
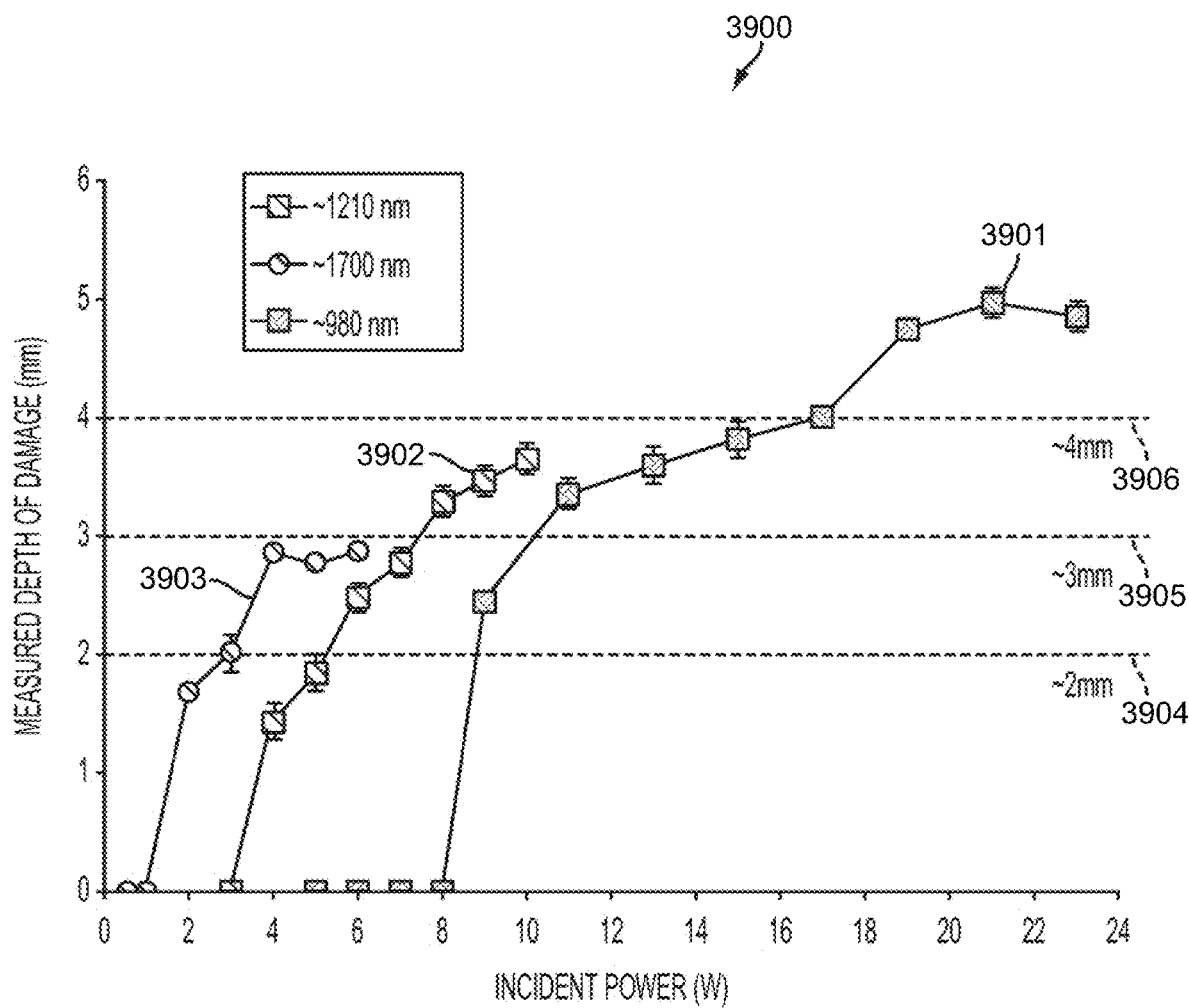
FIG. 39 plots the measured depth of damage (in millimeters) versus the time-averaged incident power (in Watts). Data is presented for laser wavelengths near 980 nm, 1210 nm and 1700 nm, and lines are drawn corresponding to penetration depths of approximately 2 mm, 3 mm, and 4 mm.

For these particular experiments, the measured depth of damage (in millimeters) versus the incident laser power (in Watts) is shown 3900 in FIG. 39. In this embodiment, laser diodes were used at wavelengths near 980 nm, 1210 nm and 1700 nm. The curve 3901 corresponds to about 980 nm, the curve 3902 corresponds to about 1210 nm, and the curve 3903 corresponds to about 1700 nm. It may be noted that there is a threshold power, above which the damage depth increases relatively rapidly. For example, the threshold power for wavelengths around 980 nm may be about 8 W, the threshold power for wavelengths around 1210 nm may be 3 W, and the threshold power for wavelengths around 1700 nm may be about 1 W. The threshold powers may be different at the different wavelengths because of the difference in water absorption (e.g., 3601 in FIG. 36). Part of the difference in threshold powers may also arise from the absorption of proteins such as collagen (e.g., 3603 in FIG. 36). After a certain power level, the damage depth appears to saturate: i.e., the slope flattens out as a function of increasing pump power.

In one embodiment, if the penetration depth is defined as the depth where damage begins to approximately saturate, then for wavelengths of about 980 nm 3901 the penetration depth 3906 may be defined as approximately 4 mm, for wavelengths of about 1210 nm 3902 the penetration depth 3905 may be defined as approximately 3 mm, and for wavelengths of about 1700 nm 3903 the penetration depth 3904 may be defined as approximately 2 mm. These are only approximate values, and other values and criteria may be used to define the penetration depth. It may also be noted that the level of damage at the highest power points differs at the different wavelengths. For example, at the highest power point of 3903 near 1700 nm, much more damage is observed, showing evidence of even boiling and cavitation. This may be due to the higher absorption level near 1700 nm (e.g., 3601 in FIG. 36). On the other hand, at the highest power point 3901 near 980 nm, the damage is not as catastrophic, but the spot size appears larger. The larger spot size may be due to the increased scattering at the shorter wavelengths (e.g., 3601 in FIG. 36). Based on data 3900 such as in FIG. 39, it may be possible to select the particular wavelength for the laser beam to be used in the non-invasive procedure.

Figure 40:
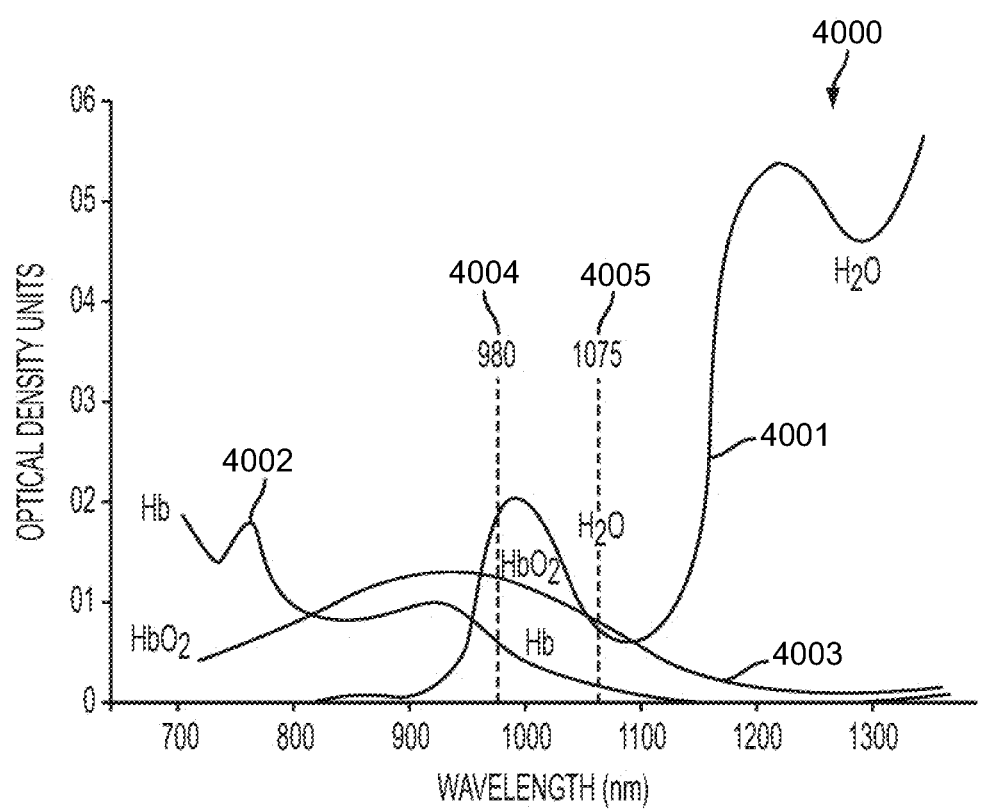
FIG. 40 illustrates the optical absorption or density as a function of wavelength between approximately 700 nm and 1300 nm for water, hemoglobin and oxygenated hemoglobin.

Even near wavelengths such as described in FIG. 39, the particular wavelength selected may be more specifically defined based on the target tissue of interest. In one particular embodiment, the vessel lumen may be modeled as water, and for this example assume that wavelengths in the vicinity of 980 nm are being selected to create thermal coagulation or occlusion. FIG. 40 shows the optical absorption or density as a function of wavelength 4000 between approximately 700 nm and 1300 nm. Curves are shown for the water absorption 4001, hemoglobin Hb absorption 4002, and oxygenated hemoglobin HbO2 4003. In this example, two particular wavelengths are compared: 980 nm 4004 and 1075 nm 4005. For instance, 980 nm may be generated using one or more laser diodes, while 1075 nm may be generated using an ytterbium-doped fiber laser. If maximizing the penetration depth is the significant problem, then 1075 nm 4005 may be preferred, since it falls near a local minimum in water 4001, hemoglobin 4002, and oxygenated hemoglobin 4003 absorption. On the other hand, if the penetration depth at 980 nm 4004 is adequate and the problem is to generate heat through water absorption, then 980 nm 4004 may be a preferred wavelength for the light source because of the higher water absorption. This wavelength range is only meant to be exemplary, but other wavelength ranges and particular criteria for selecting the wavelength may be used and are intended to be covered by this disclosure.

Figure 41:
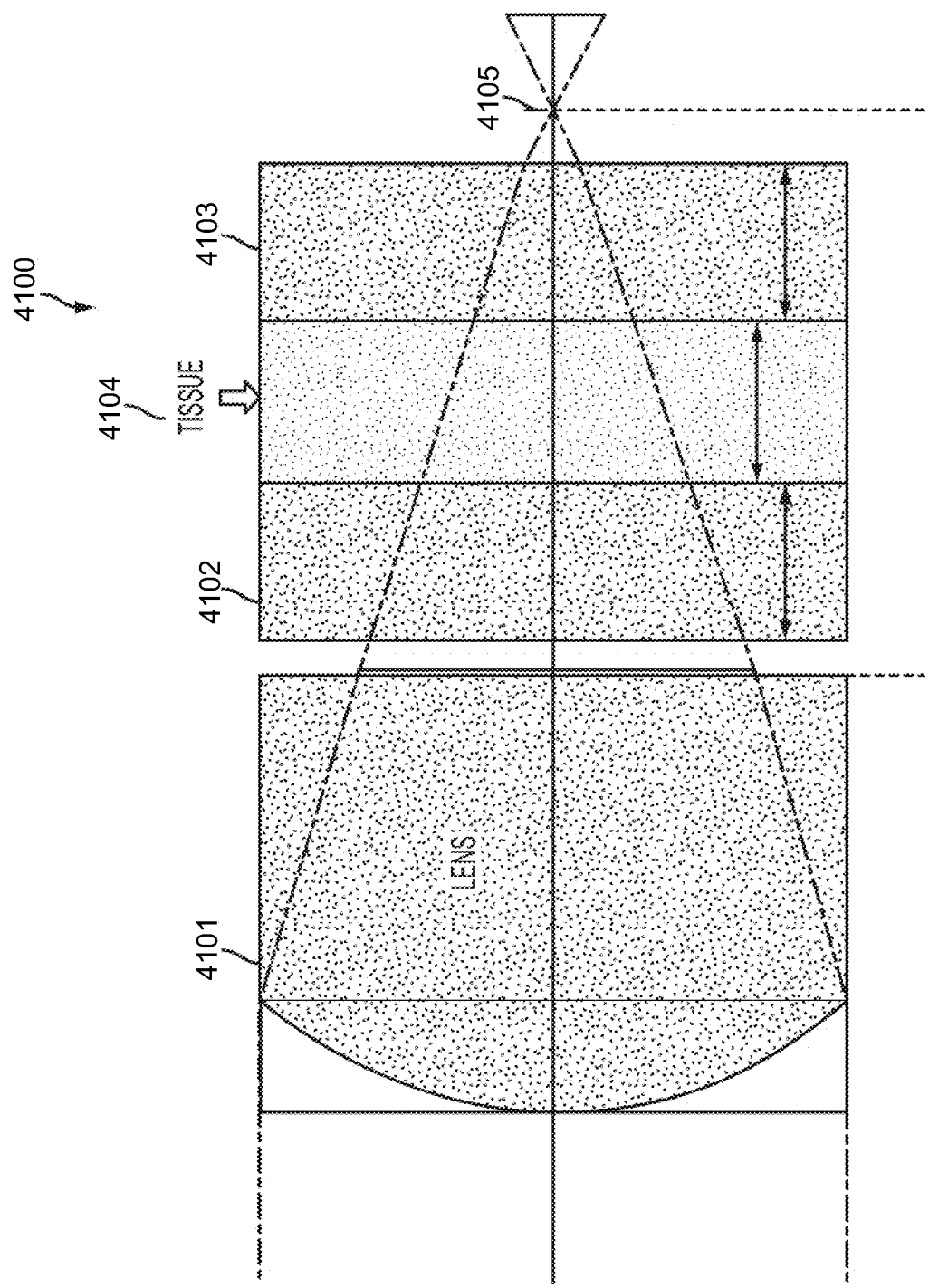
FIG. 41 shows a set-up used for in vitro damage experiments using focused infrared light. After a lens system, the tissue is placed between two microscope slides.

In another embodiment, focused infrared light has been used to preserve the top layer of a tissue while damaging nerves at a deeper level. For instance, FIG. 41 illustrates the set-up 4100 used for the focused infrared experiments. In this embodiment, a lens 4101 is used to focus the light. Although a single lens is shown, either multiple lenses, GRIN (gradient index) lenses, curved mirrors, or a combination of lenses and mirrors may be used. In this particular example, the tissue 4104 is placed between two microscope slides 4102 and 4103 for in vitro experiments. The tissue 4104 is renal artery wall either from porcine or bovine animals (about 1.2 mm thick sample)—i.e., this is the artery leading to the kidneys, and it is the artery where typically renal denervation may be performed to treat hypertension. For this example, the minimum beam waist 4105 falls behind the tissue, and the intensity contrast from the front of the tissue (closest to the lens) to the back of the tissue (furthest from the lens) is about 4:1. These are particular ranges used for this experiment, but other values and locations of minimum beam waist may also be used and intended to be covered by this disclosure.

Figure 42A:
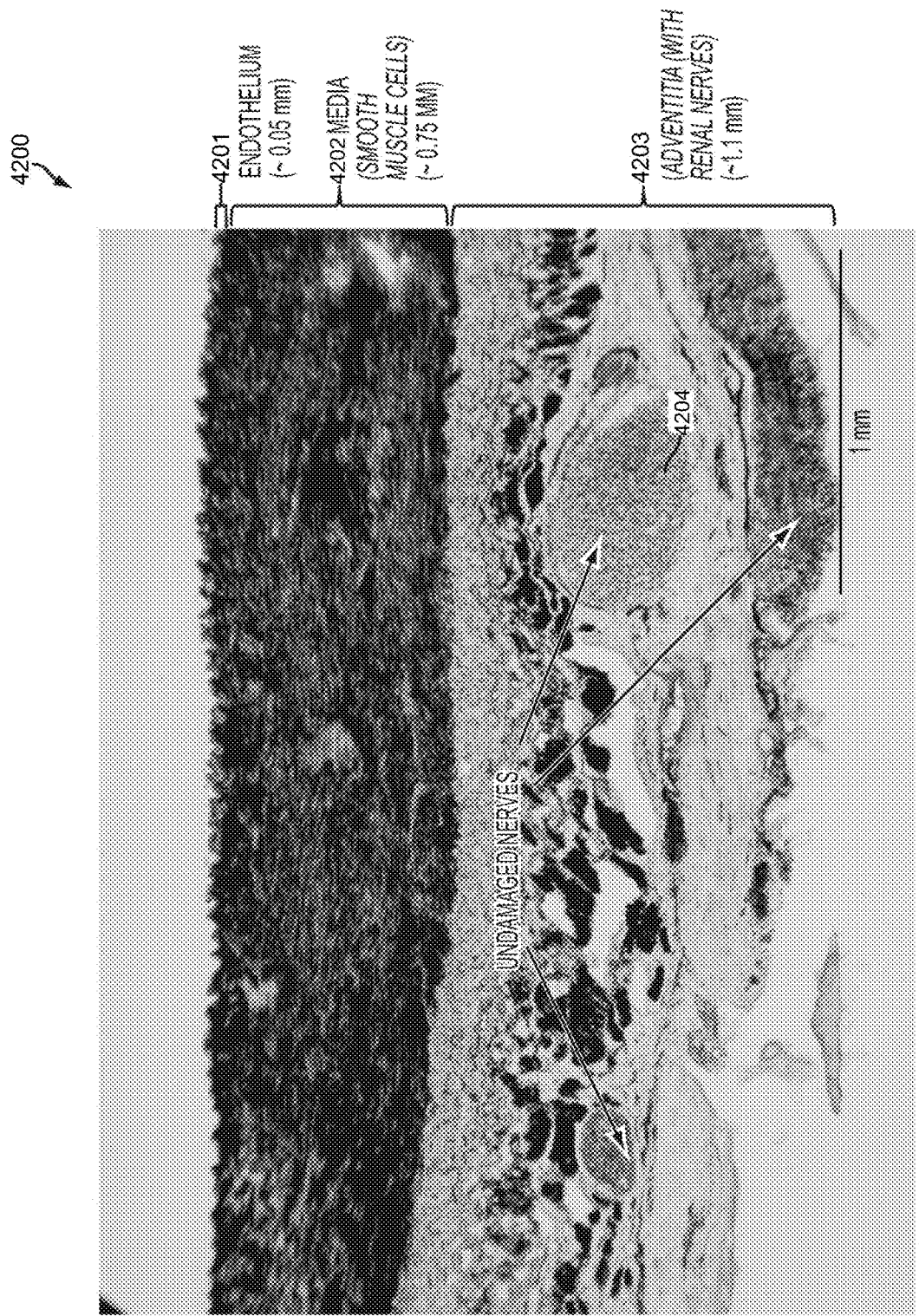
FIGS. 42A and 42B present histology of renal arteries comprising endothelium, media and adventitia layers and some renal nerves in or below the adventitia.
Figure 42B:
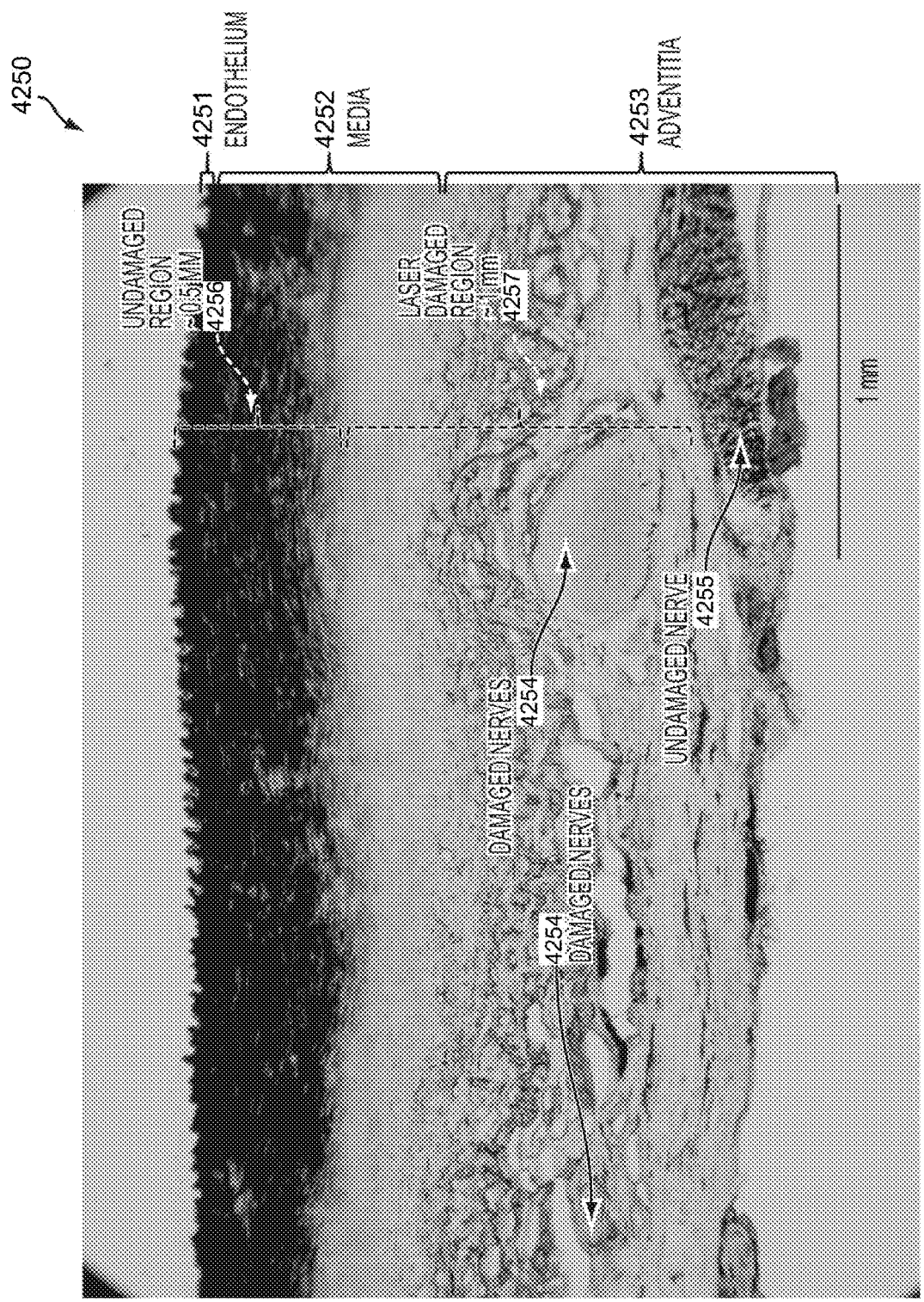

For a particular embodiment, histology of the renal artery is shown in FIG. 42A for no laser exposure 4200 and shown in FIG. 42B with focused infrared laser exposure 4250. In this experiment, the beam diameter incident on the lens was about 4 mm, and the distance from the edge of the flat side of lens to the minimum beam waist was about 3.75 mm. The beam diameter on the front side of the renal artery (i.e., the endothelium side) was about 1.6 mm, and the beam diameter on the back side of the renal artery was about 0.8 mm. In FIG. 42A with no laser exposure, the layers of the artery wall may be identified: top layer of endothelium 4201 that is about 0.05 mm thick, the media comprising smooth muscle cells or tissue 4202 that is about 0.75 mm thick, and the adventitia 4203 comprising some of the renal nerves 4204 that is about 1.1 mm thick. These are particular values for this experiment, and other layers and thicknesses may also be used and are intended to be covered by this disclosure.

The histology with focused infrared light exposure 4250 is illustrated in FIG. 42B. The laser light used is near 1708 nm from a cascaded Raman oscillator (described in greater detail herein), and the power incident on the tissue is about 0.8 W and the beam is scanned across the tissue at a rate of approximately 0.4 mm/sec. The various layers are still observable: the endothelium 4251, the media 4252, and the adventitia 4253. With this type of histology, the non-damaged regions remain darker (similar to FIG. 42A), while the laser induced damaged regions turn lighter in color. In this example, the endothelium 4251 and top layer of the media 4252 remain undamaged—i.e., the top approximately 0.5 mm is the undamaged region 4256. The laser damaged region 4257 extends for about 1 mm, and it includes the bottom layer of the media 4252 and much of the adventitia 4253. The renal nerves 4254 that fall within the damage region 4257 are also damaged (i.e., lighter colored). On the other hand, the renal nerves beyond this depth, such as 4255, may remain undamaged.

Thus, by using focused infrared light near 1708 nm in this example, the top approximately 0.5 mm of the renal artery is spared from laser damage. It should be noted that when the same experiment is conducted with a collimated laser beam, the entire approximately 1.5 mm is damaged (i.e., including regions 4256 and 4257). Therefore, the cone of light with the lower intensity at the top and the higher intensity toward the bottom may, in fact, help preserve the top layer from damage. There should be a Beer's Law attenuation of the light intensity as the light propagates into the tissue. For example, the light intensity should reduce exponentially at a rate determined by the absorption coefficient. In these experiments it appears that the focused light is able to overcome the Beer's law attenuation and still provide contrast in intensity between the front and back surfaces.

Figure 43:
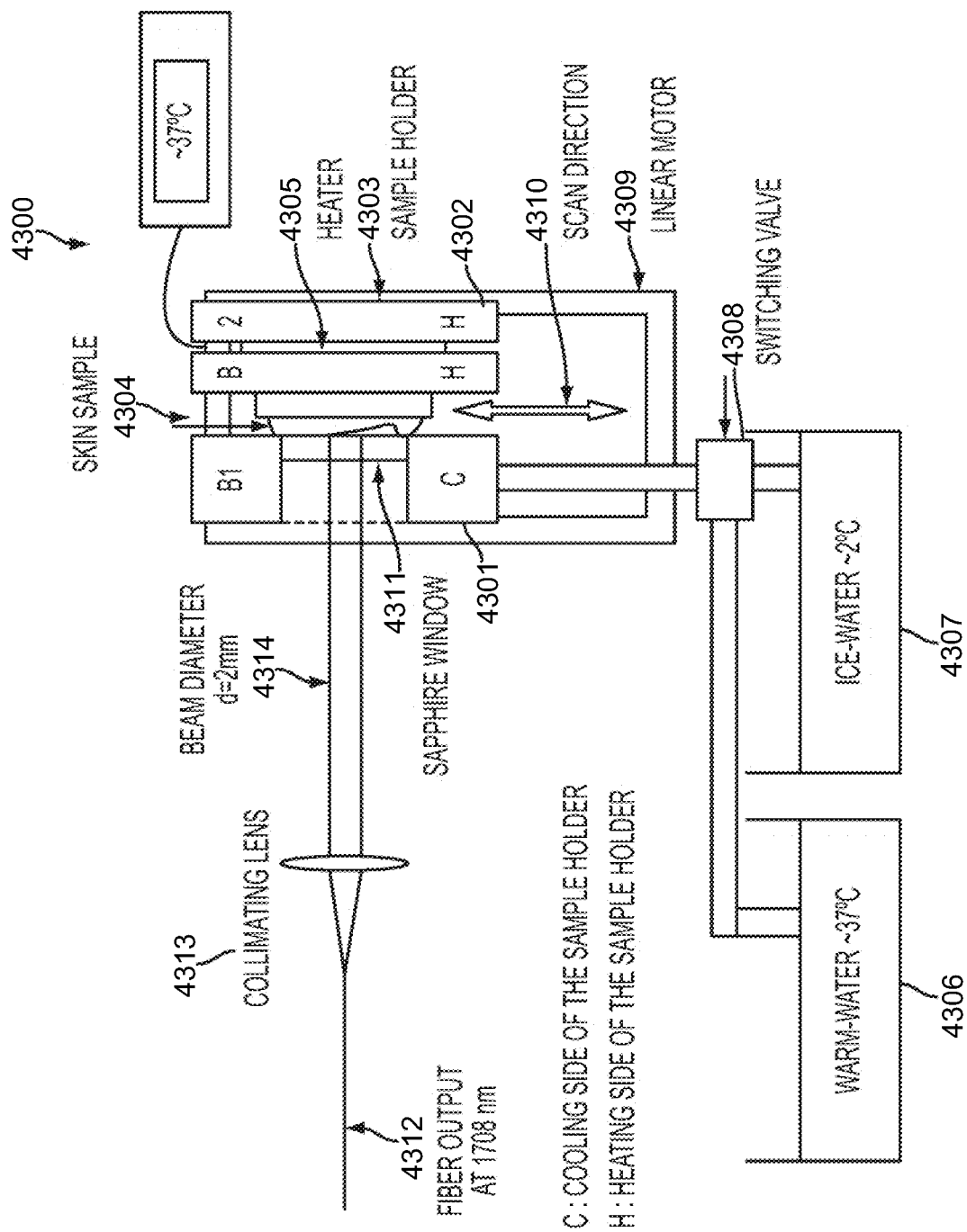
FIG. 43 illustrates the experimental set-up for ex vivo skin laser treatment with surface cooling to protect the epidermis and top layer of the dermis.
Figure 44A:
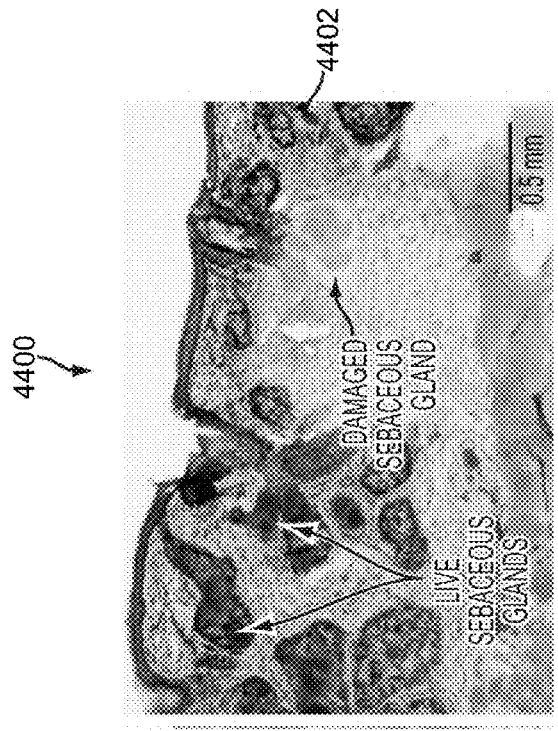
FIGS. 44A-44D show MTT histo-chemistry of ex vivo human skin treated with ~1708 nm laser and cold window (5 seconds precool; 2 mm diameter spot exposure for 3 seconds) at 725 mW (FIGS. 44A and 44B) corresponding to ~70 J/cm2 average fluence and 830 mW (FIGS. 44C and 44D) corresponding to ~80 J/cm2 average fluence.
Figure 44B:
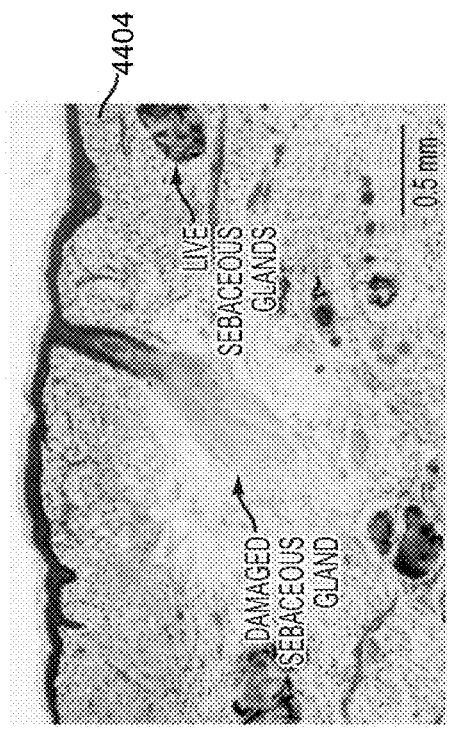
Figure 44C:
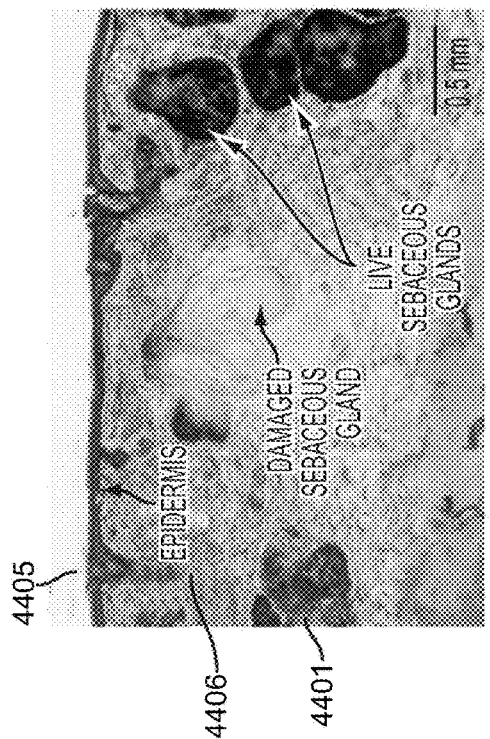
Figure 44D:

In another embodiment, experiments have also been conducted on dermatology samples with surface cooling, and surface cooling is shown to preserve the top layer of the skin during laser exposure. In this particular example, the experimental set-up 4300 is illustrated in FIG. 43. The skin sample 4304, or more generally sample under test, is placed in a sample holder 4303. The sample holder 4303 has a cooling side 4301 and a heating side 4302. The heating side 4302 comprises a heater 4305, which may be adjusted to operate around 37 degrees Celsius—i.e., close to body temperature. The cooling side 4301 is coupled to an ice-water bath 4307 (around 2 degrees Celsius) and a warm-water bath 4306 (around 37 degrees Celsius) through a switching valve 4308. The entire sample holder 4303 is mounted on a linear motor 4309, so the sample can be moved perpendicular 4310 to the incoming light beam.

In this embodiment, the light is incident on the sample 4304 through a sapphire window 4311. The sapphire material 4311 is selected because it is transparent to the infrared wavelengths, while also being a good thermal conductor. Thus, the top layer of the sample 4304 may be cooled by being approximately in contact with the sapphire window 4311. The laser light 4312 used is near 1708 nm from a cascaded Raman oscillator (described in greater detail herein), and one or more collimating lenses 4313 are used to create a beam with a diameter 4314 of approximately 2 mm. This is one particular embodiment of the sample surface cooling arrangement, but other apparatuses and methods may be used and are intended to be covered by this disclosure.

Experimental results obtained using the set-up of FIG. 43 are included in FIG. 44. In this example, FIG. 44 shows the MTT histochemistry of human skin 4400 treated with ~1708 nm laser (5 seconds pre-cool; 2 mm diameter spot exposure for 3 seconds) at 725 mW (A 4401, B 4402) corresponding to about 70 J/cm2 average fluence, and 830 mW (C 4403, D 4404) corresponding to about 80 J/cm2 average fluence. The images in FIG. 44 show that the application of a cold window was effective in protecting the epidermis 4405 (darker top layer) and the top approximately 0.4 or 0.5 mm of the dermis 4406. As before, the darker regions of the histology correspond to undamaged regions, while the lighter regions correspond to damaged regions. In contrast, when no surface cooling is applied, then thermal damage to the dermis occurs in the epidermis and dermis where the laser exposure occurs, and the thermal damage extends to about 1.3 or 1.4 mm or more from the skin surface. Thus, surface cooling applied to the skin may help to reduce or eliminate damage to the top layer of the skin under laser exposure.

In summary, experiments verify that infrared light, such as near 980 nm, 1210 nm, or 1700 nm, may achieve penetration depths between approximately 2 mm to 4 mm or more. The top layer of skin or tissue may be spared damage under laser exposure by focusing the light beyond the top layer, applying surface cooling, or some combination of the two. These are particular experimental results, but other wavelengths, methods and apparatuses may be used for achieving the penetration and minimizing damage to the top layer and are intended to be covered by this disclosure. In an alternate embodiment, it may be beneficial to use wavelengths near 1310 nm if the absorption from skin constituents (FIG. 36), such as collagen 3603, adipose 3602 and elastin 3604, are to be minimized. The water absorption 3601 near 1310 nm may still permit a penetration depth of approximately 1 cm, or perhaps less. In yet another embodiment, wavelengths near 1210 nm may be beneficial, if penetration depths on the order of 3 mm are adequate and less scattering loss (e.g. 3601 in FIG. 36) is desired. Any of FIG. 27, 32, 35, 36, or 37 may be used to select these or other wavelengths to achieve the desired penetration depth and to also perhaps target particular tissue of interest, and these alternate embodiments are also intended to be covered by this disclosure.

Detection Systems

As discussed earlier, the active remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. Using a lock-in type technique (e.g., detecting at the same frequency as the pulsed light source and also possibly phase locked to the same signal), the detection system may be able to reject background or spurious signals and increase the signal-to-noise ratio of the measurement. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 45:
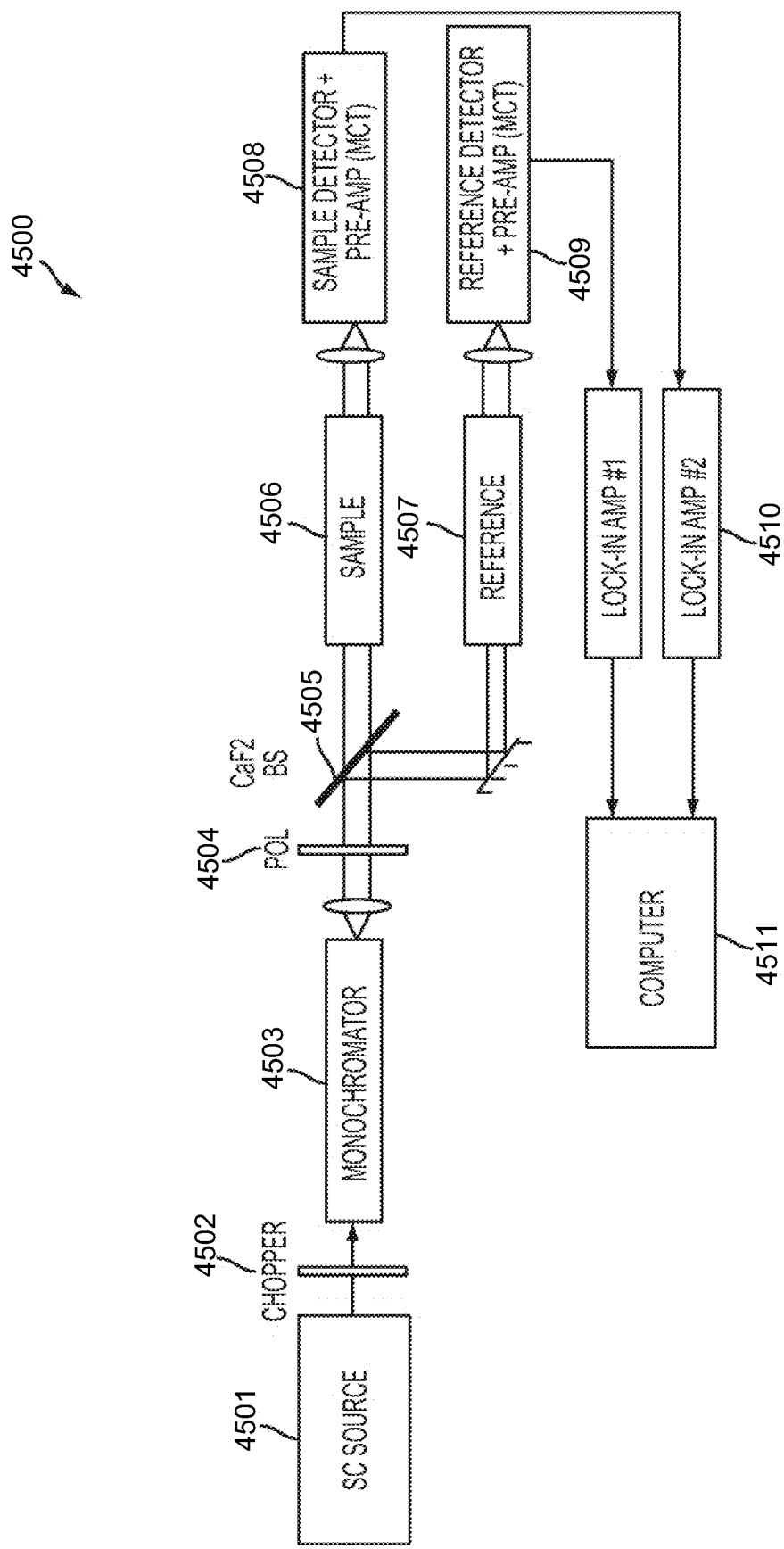
FIG. 45 exemplifies a dual-beam experimental set-up that may be used to subtract out (or at least minimize the adverse effects of) light source fluctuations.

In one example of multi-beam detection systems, a dual-beam set-up 4500 such as in FIG. 45 may be used to subtract out (or at least minimize the adverse effects of) light source fluctuations. In one embodiment, the output from an SC source 4501 may be collimated using a calcium fluoride (CaF2) lens 4502 and then focused into the entrance slit of the monochromator 4503. At the exit slit, light at the selected wavelength is collimated again and may be passed through a polarizer 4504 before being incident on a calcium fluoride beam splitter 4505. After passing through the beam splitter 4505, the light is split into a sample 4506 and reference 4507 arm to enable ratiometric detection that may cancel out effects of intensity fluctuations in the SC source 4501. The light in the sample arm 4506 passes through the sample of interest and is then focused onto a HgCdTe detector 4508 connected to a pre-amp. A chopper 4502 and lock-in amplifier 4510 setup enable low noise detection of the sample arm signal. The light in the reference arm 4507 passes through an empty container (cuvette, gas cell etc.) of the same kind as used in the sample arm. A substantially identical detector 4509, pre-amp and lock-in amplifier 4510 is used for detection of the reference arm signal. The signal may then be analyzed using a computer system 4511. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as illustrated in the representative embodiment of FIG. 45 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Although the present disclosure has been described in several embodiments, a myriad of changes, variations, alterations, transformations, and modifications may be suggested to one skilled in the art, and it is intended that the present disclosure encompass such changes, variations, alterations, transformations, and modifications as falling within the spirit and scope of the appended claims.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

What is claimed is:

1. An optical tomography system, comprising:
an array of laser diodes to generate light having one or more optical wavelengths that includes at least one near-infrared wavelength between 600 nanometers and 1000 nanometers, at least one laser diode of the array comprises one or more Bragg reflectors;
at least one of the laser diodes to pulse at a modulation frequency between 10 Megahertz and 1 Gigahertz and to have a phase associated with the modulation frequency;
wherein at least a portion of the light generated by the array is configured to penetrate tissue comprising skin; and
a detection system comprising at least one photo-detector, a lens at an input to the at least one photo-detector, and a processor to process digitized signals received from the at least one photo-detector, the detection system configured to (i) measure a phase shift of at least a portion of the light from the array of laser diodes reflected from the tissue relative to the portion of the light generated by the array to penetrate the tissue, (ii) measure time-of-flight of at least a portion of the light from the array of laser diodes reflected from the tissue relative to the portion of the light generated by the array to penetrate the tissue, (iii) generate one or more images of the tissue based at least in part on an amplitude of at least a portion of the light from the array of laser diodes reflected from the tissue, and (iv) detect oxy- or deoxy-hemoglobin in the tissue.

2. The optical tomography system of claim 1 wherein the detection system is configured to be synchronized to the pulsing of the array of laser diodes, and wherein at least some of the laser diodes in the array of laser diodes operate at a wavelength near 940 nanometers.

3. The optical tomography system of claim 1, wherein the detection system is configured to identify veins within the tissue.

4. The optical tomography system of claim 1, wherein the detection system is further configured to:
receive light while the array of laser diodes is off and covert the received light into a first signal;
receive light while at least a part of the array of laser diodes is on and convert the received light into a second signal, the received light including at least a part of the light from the array of laser diodes reflected from the tissue; and
wherein the detection system processor is configured to difference the first signal and the second signal.

5. The optical tomography system of claim 1 further comprising:
a second laser diode to be pulsed and to generate light having one or more optical wavelengths, and wherein the second laser diode comprises one or more Bragg reflectors;
a beam splitter to:
receive at least part of the light from the second laser diode, split the received light into a sample arm and a reference arm, and direct at least a portion of the sample arm light to tissue comprising skin;
at least one first detector to receive at least a portion of the reference arm light and to generate a reference detector output;
at least one second detector to receive from the tissue at least a portion of reflected sample arm light and to generate a sample detector output; and wherein the detection system processor is configured to measure another time-of-flight based at least in part on the sample detector output.

6. The optical tomography system of claim 1, wherein the detection system processor is configured to implement pattern matching and a threshold function to correlate detected blood concentrations with a library of known concentrations to determine overlap between the detected concentrations and known concentrations in the library.

7. The optical tomography system of claim 6, wherein the detection system processor is further configured to identify differences in detected concentrations using one or more of linear regression, partial least squares, and principal component regression.

8. The optical tomography system of claim 1, wherein the detection system comprises an infrared camera, wherein one or more optical filters and one or more adjustable lenses are configured to be coupled to the camera, and wherein the detection system processor is configured to identify differences in detected concentrations using one or more of linear regression, partial least squares, and principal component regression.

* * * * *

UNITED STATES PATENT AND TRADEMARK OFFICE
CERTIFICATE OF CORRECTION

PATENT NO. : 10,820,807 B2
APPLICATION NO. : 16/722188
DATED : November 3, 2020
INVENTOR(S) : Islam It is certified that error appears in the above-identified patent and that said Letters Patent is hereby corrected as shown below:

On the Title Page

Item (60), Delete:
"Related U.S. Application Data
(60) Continuation of application No. 16/506,385, filed on Jul. 9, 2019, now Pat. No. 10,517,484, which is a continuation of application No. 16/284,514, filed on Feb. 25, 2019, now abandoned, and a continuation of application No. 16/272,069, filed on Feb. 11, 2019, now abandoned, and a continuation of application No. 16/241,628, filed on Jan. 7, 2019, now Pat. No. 10,441,176, and a continuation of application No. 16/188,194, filed on Nov. 12, 2018, now Pat. No. 10,386,230, said application No. 16/272,069 is a continuation of application No. 16/029,611, filed on Jul. 8, 2018, now Pat. No. 10,201,283, said application No. 16/284,514 is a continuation of application No. 16/016,649, filed on Jun. 24, 2018, now Pat. No. 10,213,113, said application No 16/241,628 is a continuation of application No. 16/015,737, filed on Jun. 22, 2018, now Pat. No. 10,172,523, said application No. 16/506,885 is a continuation of application No. 16/004,359, filed on Jun. 9, 2018, said application No. 16/188,194 is a continuation of application No. 16/004,154, filed on Jun. 8, 2018, now Pat. No. 10,126,233, said application No. 16/029,611 is a continuation of application No. 15/888,052, filed on Feb. 4, 2018, now Pat. No. 10,136,819, said application No. 16/016,649 is a continuation of application No. 15/860,065, filed on Jan. 2, 2018, now Pat. No.

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

10,098,546, said application No. 16/004,154 is a continuation of application No. 15/855,201, filed on Dec. 27, 2017, now Pat. No. 9,995,722, which is a continuation of application No. 15/711,907, filed on Sep. 21, 2017, now Pat. No. 9,897,584, said application No. 15/860,065 is a continuation of application No. 15/686,198, filed on Aug. 25, 2017, now Pat. No. 9,861,286, said application No. 16/015,737 is a continuation of application No. 15/594,053, filed on May 12, 2017, now Pat. No. 10,188,299, said application No. 15/711,907 is a division of application No. 15/357,225, filed on Nov. 21, 2015, now Pat. No. 9,797,876, said application No. 15/686,198 is a continuation of application No. 15/357,136, filed on Nov. 21, 2016, now Pat. No. 9,757,040, said application No. 15/888,052 is a continuation of application No. 15/212,549, filed on Jul. 18, 2016, now Pat. No. 9,885,698, said application No. 15/594,053 is a continuation of application No. 14/875,709, filed on Oct. 6, 2015, now Pat. No. 9,651,533, said application No. 15/357,136 is a continuation of application No. 14/651,367, filed as application No. PCT/US2013/075736 on Dec. 17, 2013, now Pat. No. 9,500,635, said application No. 15/357,225 is a continuation of application No. 14/650,981, filed as application No. PCT/US2013/075767 on Dec. 17, 2013, now Pat. No. 9,500,634, said application No. 15/212,549 is a continuation of application No. 14/650,897, filed as application No. PCT/US2013/075700 on Dec. 17, 2013, now Pat. No. 9,494,567, said application No. 16/004,359 is a continuation of application No. 14/109,007, filed on Dec. 17, 2013, now Pat. No. 9,993,159, said application No. 14/875,709 is a continuation of application No. 14/108,986, filed on Dec. 17, 2013, now Pat. No. 9,164,032.

(60) Provisional application No. 61/754,698, filed on Jan. 21, 2013, provisional application No. 61/747,477, filed on Dec. 31, 2012, provisional application No. 61/747,472, filed on Dec. 31, 2012, provisional application No. 61/747,485, filed on Dec. 31, 2012, provisional application No. 61/747,487, filed on Dec. 31, 2012, provisional application No. 61/747,553, filed on Dec. 31, 2012."

CERTIFICATE OF CORRECTION (continued)
U.S. Pat. No. 10,820,807 B2

And Insert:
--Related U.S. Application Data
(60) Continuation of application No. 16/506,885, filed on Jul. 9, 2019, now Pat. No. 10,517,484, which is a continuation of application No. 16/272,069, filed on Feb. 11, 2019, now abandoned, which is a continuation of application No. 16/029,611, filed on Jul. 8, 2018, now Pat. No. 10,201,283, which is a continuation of application No. 15/888,052, filed on Feb. 4, 2018, now Pat. No. 10.136,819, which is a continuation of application No. 15/212,549, filed on Jul. 18, 2016, now Pat. No. 9,885,698, which is a continuation of application No. 14/650,897, filed on Jun. 10, 2015, now Pat. No. 9,494,567, filed as application No. PCT/US2013/075700 on Dec. 17, 2013, said application No. 16/506,885 is a continuation of application No. 16/004,359, filed on Jun. 9, 2018, which is a continuation of application No. 14/109,007, filed on Dec. 17, 2013, now Pat. No. 9,993,159, said application No. 16/506,885 is a continuation of application No. 16/188,194, filed on Nov. 12, 2018, now Pat. No. 10,386,230, which is a continuation of application No. 16/004,154, filed on Jun. 8, 2018, now Pat. No. 10,126,283, which is a continuation of application No. 15/855,201, filed on Dec. 27, 2017, now Pat. No. 9,995,722, which is a continuation of application No. 15/711,907, filed on Sep. 21, 2017, now Pat. No. 9,897,584, which is a division of application No. 15/357,225, filed on Nov. 21, 2016, now Pat. No. 9,797,876, which is a continuation of application No. 14/650,981, filed on Jun. 10, 2015, now Pat. No. 9,500,634, filed as application No. PCT/US2013/075767 on Dec. 17, 2013, said application No. 16/506,885 is a continuation of application No. 16/241,628, filed on Jan. 7, 2019, now Pat. No. 10,441,176, which is a continuation of application No. 16/015,737, filed on Jun. 22, 2018, now Pat. No. 10,172,523, which is a continuation of application No. 15/594,053, filed on May 12, 2017, now Pat. No. 10,188,299, which is a continuation of application No. 14/875,709, filed on Oct. 6, 2015, now Pat. No. 9,651,533, which is a continuation of application No. 14/108,986, filed on Dec. 17, 2013, now Pat. No. 9,164,032, said application No. 16/506,885 is a continuation of application No. 16/284,514, filed on Feb. 25, 2019, now abandoned, which is a continuation of

CERTIFICATE OF CORRECTION (continued)
U.S. Pat. No. 10,820,807 B2 application No. 16/016,649, filed on Jun. 24, 2018, now Pat. No. 10,213,113, which is a continuation of application No. 15/860,065, filed on Jan. 2, 2018, now Pat. No. 10,098,546, which is a continuation of application No. 15/686,198, filed on Aug. 25, 2017, now Pat. No. 9,861,286, which is a continuation of application No. 15/357,136, filed on Nov. 21, 2016, now Pat. No. 9,757,040, which is a continuation of application No. 14/651,367, filed on Jun. 11, 2015, now Pat. No. 9,500,635, filed as application No. PCT/US2013/075736 on Dec. 17, 2013.

(60) Provisional application No. 61/747,472, filed on Dec. 31, 2012, provisional application No. 61/747,553, filed on Dec. 31, 2012, provisional application No. 61/747,485, filed on Dec. 31, 2012, provisional application No. 61/747,487, filed on Dec. 31, 2012, provisional application No. 61/747,477, filed on Dec. 31, 2012, provisional application No. 61/754,698, filed on Jan. 21, 2013.--